US012558398B2

(12) United States Patent
Duda et al.

(10) Patent No.: US 12,558,398 B2
(45) Date of Patent: Feb. 24, 2026

(54) INFLAMMATORY DISEASE TREATMENT WITH COMPLEMENT INHIBITORS

(71) Applicant: UCB Holdings, Inc., Smyrna, GA (US)

(72) Inventors: Petra Duda, Charlestown, MA (US); Ramin Farzaneh-Far, Brookline, MA (US); Alonso Ricardo, Winchester, MA (US); Camil Sayegh, Belmont, MA (US); Nanqun Zhu, Lexington, MA (US); Douangsone D. Vadysirisack, Boston, MA (US); Olivier Boyer, Rouen (FR); Laurent Drouot, Blainville-Crevon (FR)

(73) Assignee: UCB Holdings, Inc., Smyrna, GA (US)

( * ) Notice: Subject to any disclaimer, the term of this patent is extended or adjusted under 35 U.S.C. 154(b) by 1096 days.

(21) Appl. No.: 17/615,494

(22) PCT Filed: Jun. 4, 2020

(86) PCT No.: PCT/US2020/036091
§ 371 (c)(1),
(2) Date: Nov. 30, 2021

(87) PCT Pub. No.: WO2020/247607
PCT Pub. Date: Dec. 10, 2020

(65) Prior Publication Data

US 2022/0257697 A1 Aug. 18, 2022

Related U.S. Application Data

(60) Provisional application No. 62/984,827, filed on Mar. 4, 2020, provisional application No. 62/926,874, filed on Oct. 28, 2019, provisional application No. 62/899,872, filed on Sep. 13, 2019, provisional application No. 62/856,906, filed on Jun. 4, 2019.

(30) Foreign Application Priority Data

Mar. 4, 2020 (FR) ...................................... 2002201

(51) Int. Cl.

| | |
|---|---|
| ***A61K 35/16*** | (2015.01) |
| ***A61K 38/12*** | (2006.01) |
| ***A61P 21/00*** | (2006.01) |
| ***C07K 16/28*** | (2006.01) |
| ***G01N 33/564*** | (2006.01) |
| *A61M 5/32* | (2006.01) |

(52) U.S. Cl.
CPC .............. *A61K 38/12* (2013.01); *A61K 35/16* (2013.01); *A61P 21/00* (2018.01); *C07K 16/2887* (2013.01); *G01N 33/564* (2013.01); *A61M 5/329* (2013.01); *C07K 2317/24* (2013.01)

(58) Field of Classification Search
None
See application file for complete search history.

(56) References Cited

U.S. PATENT DOCUMENTS

| | | | |
|---|---|---|---|
| 4,033,940 | A | 7/1977 | Hughes et al. |
| 4,179,337 | A | 12/1979 | Davis et al. |
| 4,216,141 | A | 8/1980 | Rivier et al. |
| 4,271,068 | A | 6/1981 | Kamber et al. |
| 4,301,144 | A | 11/1981 | Iwashita et al. |
| 4,496,689 | A | 1/1985 | Mitra |
| 4,640,835 | A | 2/1987 | Shimizu et al. |
| 4,670,417 | A | 6/1987 | Iwasaki et al. |
| 4,791,192 | A | 12/1988 | Nakagawa et al. |
| 5,270,170 | A | 12/1993 | Schatz et al. |
| 5,338,665 | A | 8/1994 | Schatz et al. |
| 5,371,109 | A | 12/1994 | Engstrom et al. |
| 5,427,908 | A | 6/1995 | Dower et al. |
| 5,580,717 | A | 12/1996 | Dower et al. |
| 5,585,353 | A | 12/1996 | Merrifield et al. |
| 5,591,828 | A | 1/1997 | Bosslet et al. |
| 5,596,078 | A | 1/1997 | Andersson et al. |
| 5,618,676 | A | 4/1997 | Hitzeman et al. |
| 5,643,768 | A | 7/1997 | Kawasaki |
| 5,658,754 | A | 8/1997 | Kawasaki |
| 5,726,287 | A | 3/1998 | Andersson et al. |
| 5,750,344 | A | 5/1998 | Doyle |
| 5,766,897 | A | 6/1998 | Braxton |
| 5,824,784 | A | 10/1998 | Kinstler et al. |
| 5,834,318 | A | 11/1998 | Buettner |
| 5,837,500 | A | 11/1998 | Ladner et al. |
| 5,843,701 | A | 12/1998 | Gold et al. |

(Continued)

FOREIGN PATENT DOCUMENTS

| | | | |
|---|---|---|---|
| EP | 3154561 | A2 | 4/2017 |
| JP | 2010-502708 | A | 1/2010 |

(Continued)

OTHER PUBLICATIONS

Konishi et al., Myasthenia gravis: relations between jitter in single-fiber EMG and antibody to acetylcholine receptor; 1981, Neurology, (Ny)31: 386-392. (Year: 1981).*
Ernste and Reed, Idiopathic inflammatory myopathies: current trends in pathogenesis, clinical features, and up-to-date treatment recommendations; 2013, Mayo Clin. Proc.; 88(1): 83-105. (Year: 2013).*
Beecher et al., Therapies directed against B-cells and downstream effectors in generalized autoimmune myasthenia gravis: current status; Feb. 14, 2019, Drugs, 79: 353-364. (Year: 2019).*
Allenbach, Y. et al., "Necrosis in anti-SRP+ and anti-HMGCR+ myopathies: Role of autoantibodies and complement," Neurology 90(6), Feb. 6, 2018, pp. e507-e517.

(Continued)

*Primary Examiner* — Daniel E Kolker
*Assistant Examiner* — James Ryland Melchior
(74) *Attorney, Agent, or Firm* — Fenwick & West LLP

(57) ABSTRACT

The present disclosure provides methods of treating inflammatory indications with complement inhibitor compounds and compositions. Included are compounds and methods of treating neuromuscular inflammatory indications, such as Immune-Mediated Necrotizing Myopathy.

21 Claims, 4 Drawing Sheets

Specification includes a Sequence Listing.

(56) References Cited

U.S. PATENT DOCUMENTS

| | | | |
|---|---|---|---|
| 5,854,018 | A | 12/1998 | Hitzeman et al. |
| 5,856,123 | A | 1/1999 | Hitzeman et al. |
| 5,919,651 | A | 7/1999 | Hitzeman et al. |
| 5,922,680 | A | 7/1999 | Paulsen et al. |
| 5,990,237 | A | 11/1999 | Bentley et al. |
| 5,990,273 | A | 11/1999 | Andersson et al. |
| 6,086,918 | A | 7/2000 | Stern et al. |
| 6,194,550 | B1 | 2/2001 | Gold et al. |
| 6,242,565 | B1 | 6/2001 | Kishida et al. |
| 6,258,558 | B1 | 7/2001 | Szostak et al. |
| 6,261,804 | B1 | 7/2001 | Szostak et al. |
| 6,268,343 | B1 | 7/2001 | Knudsen et al. |
| 6,309,669 | B1 | 10/2001 | Setterstrom et al. |
| 6,348,584 | B1 | 2/2002 | Hodgson et al. |
| 6,355,245 | B1 | 3/2002 | Evans et al. |
| 6,361,943 | B1 | 3/2002 | Yanagawa et al. |
| 6,673,901 | B2 | 1/2004 | Koide |
| 6,716,973 | B2 | 4/2004 | Baskerville et al. |
| 6,720,472 | B2 | 4/2004 | Chada et al. |
| 6,844,010 | B1 | 1/2005 | Setterstrom et al. |
| 6,962,781 | B1 | 11/2005 | Williams |
| 7,348,401 | B2 | 3/2008 | Johnson et al. |
| 7,744,910 | B2 | 6/2010 | Gschneidner et al. |
| 8,101,586 | B2 | 1/2012 | Rock et al. |
| 8,329,169 | B2 | 12/2012 | Fung et al. |
| 8,377,437 | B2 | 2/2013 | Van Lookeren Campagne |
| 8,652,477 | B2 | 2/2014 | Schwaeble et al. |
| 8,703,136 | B2 | 4/2014 | Baas et al. |
| 8,753,625 | B2 | 6/2014 | Fung et al. |
| 8,778,618 | B2 * | 7/2014 | Casciola-Rosen ... G01N 33/573 435/7.1 |
| 8,911,733 | B2 | 12/2014 | Holers et al. |
| 9,079,949 | B1 * | 7/2015 | Andrien, Jr. ............ A61P 25/28 |
| 9,388,235 | B2 | 7/2016 | Halstead et al. |
| 9,937,222 | B2 | 4/2018 | Hoarty et al. |
| 10,106,579 | B2 | 10/2018 | Hoarty et al. |
| 10,208,089 | B2 | 2/2019 | Hoarty et al. |
| 10,328,115 | B2 | 6/2019 | Hoarty et al. |
| 10,435,438 | B2 | 10/2019 | Hoarty et al. |
| 10,588,936 | B2 | 3/2020 | Hoarty et al. |
| 10,835,574 | B2 | 11/2020 | DeMarco et al. |
| 11,014,965 | B2 | 5/2021 | Hoarty et al. |
| 11,752,190 | B2 * | 9/2023 | DeMarco ............. A61K 9/0019 514/13.5 |
| 2003/0040472 | A1 | 2/2003 | Larsen et al. |
| 2005/0191343 | A1 | 9/2005 | Liang |
| 2006/0270590 | A1 | 11/2006 | Lockwood et al. |
| 2008/0146490 | A1 | 6/2008 | Joabsson et al. |
| 2008/0269318 | A1 | 10/2008 | Romano |
| 2008/0313749 | A1 | 12/2008 | Timmerman et al. |
| 2009/0054623 | A1 | 2/2009 | DeFrees |
| 2010/0015139 | A1 | 1/2010 | Bansal |
| 2010/0093624 | A1 | 4/2010 | Low et al. |
| 2010/0099113 | A1 | 4/2010 | Knör et al. |
| 2010/0143344 | A1 | 6/2010 | Baas et al. |
| 2010/0166748 | A1 | 7/2010 | Guild et al. |
| 2011/0172126 | A1 | 7/2011 | Brust |
| 2011/0190221 | A1 | 8/2011 | Francois et al. |
| 2011/0269807 | A1 | 11/2011 | Baciu |
| 2012/0225056 | A1 | 9/2012 | Rother et al. |
| 2013/0029912 | A1 | 1/2013 | Holers et al. |
| 2013/0053302 | A1 | 2/2013 | Lambris et al. |
| 2013/0053311 | A1 | 2/2013 | Kalthoff et al. |
| 2013/0246083 | A1 | 9/2013 | Bell |
| 2013/0273052 | A1 | 10/2013 | Gies et al. |
| 2013/0344082 | A1 | 12/2013 | Lambris et al. |
| 2013/0345257 | A1 | 12/2013 | Hahn et al. |
| 2014/0234275 | A1 | 8/2014 | Williams |
| 2015/0011474 | A1 | 1/2015 | Berghard et al. |
| 2015/0057342 | A1 | 2/2015 | Koren et al. |
| 2015/0166606 | A1 | 6/2015 | Wang et al. |
| 2015/0359900 | A1 | 12/2015 | Wang et al. |
| 2016/0206580 | A1 | 7/2016 | Los et al. |
| 2016/0376355 | A1 | 12/2016 | Bell et al. |
| 2017/0137468 | A1 | 5/2017 | Arata et al. |
| 2018/0280530 | A1 | 10/2018 | Guo et al. |
| 2024/0254177 | A1 * | 8/2024 | Johnson ............. C07K 14/4703 |

FOREIGN PATENT DOCUMENTS

| | | | |
|---|---|---|---|
| JP | 2013543380 | A | 12/2013 |
| RU | 2406507 | C2 | 12/2010 |
| RU | 2505311 | C2 | 1/2014 |
| RU | 2014137303 | A | 4/2016 |
| TW | 201733609 | A | 10/2017 |
| WO | WO 1993/011161 | A1 | 6/1993 |
| WO | WO 1998/032427 | A1 | 7/1998 |
| WO | WO 2000/021559 | A2 | 4/2000 |
| WO | WO 2005/023866 | A2 | 3/2005 |
| WO | WO 2006/088888 | A2 | 8/2006 |
| WO | WO 2008/113834 | A2 | 9/2008 |
| WO | WO 2009/014633 | A1 | 1/2009 |
| WO | WO 2009/046198 | A2 | 4/2009 |
| WO | WO 2009/067191 | A2 | 5/2009 |
| WO | WO 2011/057158 | A1 | 5/2011 |
| WO | WO 2012/044893 | A1 | 4/2012 |
| WO | WO 2012/088247 | A2 | 6/2012 |
| WO | WO 2012/139081 | A3 | 11/2012 |
| WO | WO 2012/162215 | A1 | 11/2012 |
| WO | WO 2012/174055 | A1 | 12/2012 |
| WO | WO 2013/037267 | A1 | 3/2013 |
| WO | WO 2013/052736 | A2 | 4/2013 |
| WO | WO 2013/126006 | A1 | 8/2013 |
| WO | WO 2013/172954 | A1 | 11/2013 |
| WO | WO 2014/078622 | A1 | 5/2014 |
| WO | WO 2015/140304 | A1 | 9/2015 |
| WO | WO 2015/191951 | A2 | 12/2015 |
| WO | WO 2016/094834 | A2 | 6/2016 |
| WO | WO 2016/123371 | A1 | 8/2016 |
| WO | WO 2017/035362 | A1 | 3/2017 |
| WO | WO 2017/105939 | A1 | 6/2017 |
| WO | WO 2018/106859 | A1 | 6/2018 |
| WO | WO 2019/051436 | A1 | 3/2019 |
| WO | WO 2019/112984 | A1 | 6/2019 |
| WO | WO 2020/086506 | A1 | 4/2020 |
| WO | WO 2020/185541 | A2 | 9/2020 |
| WO | WO 2020/219822 | A1 | 10/2020 |
| WO | WO 2020/247607 | A1 | 12/2020 |

OTHER PUBLICATIONS

Anquetil, C. et al., "Myositis-specific autoantibodies, a cornerstone in immune-mediated necrotizing myopathy," Autoimmunity Reviews 18(3), Mar. 2019, pp. 223-230.

Bergua, C. et al., "In vivo pathogenicity of IgG from patients with anti-SRP or anti-HMGCR autoantibodies in immune-mediated necrotizing myopathy," Annals of the Rheumatic Diseases 78, Oct. 11, 2018, pp. 131-139.

Cong, L. et al., "Complement membrane attack complex is related with immune-mediated necrotizing myopathy," Int J Clin Exp Pathol 7(7), Jun. 2014, pp. 4143-4149.

Julien, S. et al., "Prevention of Anti-HMGCR Immune-Mediated Necrotising Myopathy by C5 Complement Inhibition in a Humanised Mouse Model," Biomedicines 10 2036, Aug. 20, 2022, pp. 1-11.

Mammen, A. L. et al., "Zilucoplan in immune-mediated necrotizing myopathy: a phase 2, randomised, double-blind, placebo-controlled, multicentre trial," Lancet Rheumatol. 5(2), Feb. 2023, pp. e67-e76.

Rojana-Udomsart, A. et al., "Complement-mediated muscle cell lysis: A possible mechanism of myonecrosis in anti-SRP associated necrotizing myopathy (ASANM)," Journal of Neuroimmunology 264(1-2), Nov. 2013, pp. 65-70.

Zhou, Y. et al., "Anti-C5 antibody treatment ameliorates weakness in experimentally acquired myasthenia gravis," The Journal of Immunology 179, Dec. 2007, pp. 8562-8567.

PCT International Search Report and Written Opinion, International Application No. PCT/US2020/036091, dated Sep. 25, 2020, 11 Pages.

Bergua C et al., "Immune-mediated necrotizing myopathy", Jan. 18, 2016 (Jan. 18, 2016), vol. 75, No. 2, p. 151-156, XP035878054; [retrieved on Jan. 18, 2016] the whole document.

(56) References Cited

OTHER PUBLICATIONS

Howard James F et al., "Safety and efficacy of eculizumab in anti-acetylcholine receptor antibody-positive refractory generalised myasthenia gravis (REGAIN): a phase 3, randomised, double-blind, placebo-controlled, multicentre study", *Lancet Neurology*, vol. 16, No. 12, Oct. 20, 2017 (Oct. 20, 2017), p. 976-986, XP085267220, Methods; p. 984, right-hand column paragraph 2—p. 985, left-hand column, paragraph 1.
Pinal-Fernandez Iago et al., "Immune-Mediated Necrotizing Myopathy", Mar. 26, 2018 (Mar. 26, 2018), vol. 20, No. 4, p. 1-10, XP036478491.
Ra Pharma, "Zilucoplan in*Generalized*Myasthenia*Gravis", Dec. 10, 2018 (Dec. 10, 2018), Retrieved from the Internet: URL:https://rapharma.com/wp-content/uploads/2018/12/Zilucoplan-in-Generalized-Myasthenia-Gravis-1.pdf XP055725510; p. 5-21.
Altschul et al., (1997) Gapped BLAST and PSI-BLAST: a new generation of protein database search programs, Nucleic Acids Res. 25(17):3389-3402.
Amara, et al., (2008) "Interaction Between the Coagulation and Complement System" in Current Topics in Complement II, J.D. Lambris (ed.), pp. 71-79 {Adv Exp Med Biol. 2008;632:71-9).
Amara, et al., (2010) Molecular intercommunication between the complement and coagulation systems. J. Immunol. 185:5628-5636.
Anonymous: "History of Changes for Study: NCT04382755" May 8, 2020, XP055809235, Retrieved from the Internet: URL:https://www.clinicaltrials.gov/cl2/history/NCT04382755?V_I=View#StudyPageTop [retrieved on May 31, 2021] the whole document.
Anonymous: "NCT04436497: Healey ALS Platform Trial—Regimen A Zilucoplan" Jun. 17, 2020.
ARIPO Form 18 Office Action for corresponding ARIPO Application No. AP/P/2016/009612 entitled "Modulation of Complement Activity" dated Feb. 19, 2019.
Aubuchowski, A. et al., (1977) Effect of covalent attachment of polyethylene glycol on immunogenicity and circulating life of bovine liver catalase, J. Biol. Chem., 252, 3582.
Australian First Examination Report for corresponding Australian Application No. 2015274482, dated Nov. 24, 2017.
Baggio, R. et al. (2002) Identification of epitope-like consensus motifs using mRNA display, J_ Mol. Recog. 15:126-13'.
Ballanti et al., (2013) Complement and autoimmunity. Immunol Res 56:477-491.
Banks, P. et al., (2000) Impact of a red-shifted dye label for high throughput fluorescence polarization assays of G protein-coupled receptors. J Biomol Screen. 5(5):329-34.
Baskerville, S. and Bartel, D.P. (2002) A ribozyme that ligates RNA to protein, Proc. Nall. Acad. Sci. USA 99:9154-9159.
Beauchamp C. O. et al., (1983) A new procedure for the synthesis of polyethylene glycol-protein adducts; effects on function, receptor recognition, and clearance of superoxide dismutase, lactoferrin, and alpha 2-macroglobulin, Anal. Biochem., 131, 25.
Bergseth, G. et al., (2013) An international serum standard for application in assays to detect human complement activation products. Mol Immunol. 56:232-9.
Berman, H.M. et al., (2000) The Protein Data Bank, Nucleic Acids Research, 28: 235-242.
Blackwell, H. E. and Grubbs, R.H. (1998) Highly Efficient Synthesis of Covalently Cross-Linked Peptide Helices by Ring-Closing Metathesis, Angew. Chem., Int. Ed. 37, 3281-3284.
Bracken, et al. (1994) Synthesis and Nuclear Magnetic Resonance Structure Determination of an .alpha.-Helical, Bicyclic, Lactam-Bridged Hexapeptide, J. Am. Chem. Soc., 116, 6431-6432.
Brodsky (2014) Paroxysmal nocturnal hemoglobinuria. Blood 2014;124:2804-2811.
Canadian Examination Report for corresponding Canadian Application No. 2949985, dated Oct. 26, 2017.
Cantel et al. (2008) Synthesis and conformational analysis of a cyclic peptide obtained via i to i+4 intramolecular side-chain to side-chain azide-alkyne 1,3-dipolar cycloaddition, J_ Org. Chem., 73 (15), 5663-5674.
Cazander G., et al., (2012) Complement activation and inhibition in wound healing. Clin Dev Immunol, 2012:534291.
Chang, Kyeong-Ok Characterization and inhibition of norovirus proteases of genogroups I and II using a fluorescence resonance energy transfer assay. Virology, 2012, 423(2), 125-133.
Cheng et al. Chromatographic separtion and Tandem MS identification of active peptides in potato protein hydrolysate that inhibit autoxidation of soybean oil-in-water emulsions. Journal of Agricultural and Food Chemistry 2010, 58 (15):8825-8832; Abstract.
Chinese Office Action for corresponding Chinese Application No. 2015800313418 dated Dec. 21, 2018.
Cichewicz et al. Cutaneous delivery of alpha-tocopherol and lipoic acid using microemulsions: influence of composition and charge J Pharm Pharmacol. Jun. 2013, vol. 65, No. 6, pp. 817-826.
Coin, I et al. (2007) Solid-phase peptide synthesis: from standard procedures to the synthesis of difficult sequences, Nature Protcols 2(12):3247-56.
Cwirla, S.E. et al. (1990) Peptides on phage: a vast library of peptides for identifying ligands, Proc. Nall. Acad. Sci. U. S.A. 87:6378-6382.
De Boer J.P., et al., (1993) Activation patterns of coagulation and fibrinolysis in baboons following infusion with lethal or sublethal dose of *Escherichia coli*. Circulatory shock. 39, 59-67.
DeAngelis RA., et al., (2012) Targeted complement inhibition as a promising strategy for preventing inflammatory complications in hemodialysis., Immunobiology, 217(11): 1097-1105.
Declercq et al: "Zilucoplan in patients with acute hypoxic respiratory failure due to COVID-19 {Zilucov): A structured summary of a study protocol for a randomised controlled trial", Trials, vol. 21, No. 1, Dec. 1, 2020.
Dedkova, L. et al. (2003) Enhanced D-amino acid incorporation into protein by modified ribosomes, J_ Am. Chem. Soc. 125: 6616-6617.
Dennis et al. (2002) Albumin binding as a general strategy for improving the pharmokinetics of proteins. J Biol Chem. 277{38): 35035-43.
Devlin, J. J., el. al., (1990). Random peptide libraries: a source of specific protein binding molecules, Science 249, 404-406.
Diurno et al: "Eculizumab treatment in patients with COVID-19: preliminary results from real life ASL Napoli 2 Nord Experience", Apr. 1, 2020 {Apr. 1, 2020).
Engelhardt, et al., (2002) Severe cold hemagglutinin disease {CHO) successfully treated with rituximab., Blood, 100 (5):1922-23.
Examination Report for corresponding New Zealand Application No. 727420 dated May 25, 2018.
Extended European Search Report for corresponding European Application No. 20157916.6 entitled "Modulators of Complement Activity" dated May 13, 2020.
Extended European Search Report for corresponding European Application No. 18788604.9 dated Apr. 15, 2021.
Extended European Search Report for corresponding European Application No. 16744125.2 dated Dec. 21, 2018.
Extended European Search Report for corresponding European Application No. 19194070.9 dated Mar. 2, 2020.
Extended European Search Report for corresponding European Application No. 15807069.8 dated Mar. 19, 2018.
First Examination Report dated May 22, 2017 in New Zealand Application No. 727420 entitled "Modulation of Complement Activity".
First Examination Report for corresponding India Application No. 201617040921 entitled "Modulation of Complement Activity" dated Dec. 9, 2019.
Forster, A.G. et al. (2003) Programming peptidomimetic syntheses by translating genetic codes designed de novo, Proc. Nall. Acad. Sci. USA 100: 6353-6357.
Fourth Examination Report for corresponding Australian Application No. 2015274482 dated Sep. 13, 2018.
Frankel, A. et al., (2003) Encodamers: unnatural peptide oligomers encoded in RNA, Chem. Biol. 10:1043-1050.
Fredslund, F. et al. (2008). Structure of and influence of a tick complement inhibitor on human complement component 5, Nature. 9:753-760.

(56) References Cited

OTHER PUBLICATIONS

Freskgard, Per-Ola et al. "Antibody therapies in CNS diseases", Neuropharmacology, Pergamon Press, Oxford, GB, vol. 120, Mar. 10, 2016.
Garbuzova-Davis and Sanberg "Blood-CNS Barrier Impairment in ALS patients versus an animal model" Frontiers N Cellular Neuroscience, vol. 8, Jan. 1, 2014.
Garland Donita L. et al: "Abstract", Scientific Reports, vol. 11, No. 1, Jan. 1, 2021, Retrieved from the Internet: URL:https://www.nature.com/articles/s41598-021-89978-8.
GENBANK Accession No. EKQ53330.1, hypothetical protein B655 1297 [*Methanobacterium* sp. Maddingley MBC34] Sep. 26, 2013 [online]. Retrieved from the Internet <URL: http:www.ncbi.nlm.nih.gov/protein/EKQ53330.1>.
Goto, Y. et al. (2008) Reprogramming the translation initiation for the synthesis of physiologically stable cyclic peptides, ACS Chem. Biol. 3:120-129.
Hadders, M.A. et al. (2012). Assembly and regulation of the membrane attack complex based on structures of C5b6 and sC5b9, Cell Reports. 1:200-207.
Haeger M., et al., (1992) Complement, neutrophil, and macrophage activation in women with severe preeclampsia and the syndrome of hemolysis, elevated liver enzymes, and low platelet count in Obstetrics & Gynecology, 79(1):19-26.
Hajishengallis G. (2010) Complement and periodontitis. Biochem Pharmacol. 15; 80(12): 1.
Hammer, R.P., "Harnessing mRNS-display for the Discovery of Macrocyclic Peptide Drugs" BPS Peptide Showcase East, Mar. 14, 2016.
Hartman et al., (2006) Enzymatic aminoacylation of tRNA with unnatural amino acids, Proc. Nall. Acad. Sci. USA 103:4356-4361.
Hartman, M.C.T. et al. (2007) An expanded set of amino acid analogs for the ribosomal translation of unnatural peptides, PLoS One 2:e972.
He, Mand Taussig, M (2002). Briefs in Functional Genomics and Proteomics. 1(2): 204-212.
Heinis, C. et al., (2009) Phage-encoded combinatorial chemical libraries based on bicyclic peptides. Nat Chem Biol. 5 (7):502-7.
Hill et al., (2006) The incidence and prevalence of paroxysmal nocturnal hemoglobinuria {PNH) and survival of patient in Yorkshire. Blood 2006; 108:Abstract 985.
Hillmen et al., (2013) Long-term safety and efficacy of sustained eculizumab treatment in patients with paroxysmal noctumal haemoglobinuria. Br J Haematol 2013; 162:62-73.
Hillmen, P. et al. (2006) "The Complement Inhibitor Eculizumab in Paroxysmal Nocturnal Hemoglobinuria" The New England Journal of Medicine, 355(12):1233-1243.
Holliger, P. et al., "Diabodies":Small bivalent and bispecific antibody fragments. PNAS. 1993. 90:6444-8.
Howard et al: "Clinical Effects of the Self-administered Subcutaneous Complement Inhibitor Zilucoplan in Patients with Moderate to Severe Generalized Myasthenia Gravis : Results of a Phase 2 Randomized, Double-Blind, Placebo-Controlled, Multicenter Clinical Trial", Jama Neurology, vol. 77. No. 5. Feb. 17, 2020.
Howard, J. F. et al. "Safety and Efficacy of Eculizumab in Anti-Acetylcholine Receptor Antibody-Positive Refractory Generalised Myasthenia Gravis (REGAIN): A Phase 3, Randomised, Double-Blind, Placebo- Controlled, Multicentre Study." The Lancet Neurology, vol. 16, No. 12, Dec. 2017, pp. 976-986.
Huber-Lang, et al., (2006) Generation of C5a in the absence of C3: a new complement activation pathway. Nature Med. 12(6):682-687.
Israel Office Action for corresponding Israel application No. 259762 entitled "Modulators of Complement Activity" dated Jun. 30, 2019.
Jackson, R.J., et al., (2001) Development of a tRNA-dependent in vitro translation system, RNA 7:765-773.
Janke et al. The arginine mimicking [beta]-amino acid [beta]3hPhe{3-H2N-CH) as S1 ligand in cyclotheonamide-based [beta]-tryptase inhibitors. Bioorg Med Chem. 2011, 19{23):7236-43;p. 7237, col. 1, Scheme 2.
Japanese Office Action for corresponding Japanese Application No. 2017-517219, dated Nov. 21, 2017.
Japanese Office Action for corresponding Japanese Application No. 2017-517219 dated Jun. 5, 2018.
Jennette et al., (2013) Complement in ANCA-associated vasculitis., Semin Nephrol. 33(6): 557-64.
Jha P., et al., (2007) The role of complement system in ocular diseases including uveitis and macular degeneration., Mol Immunol. 44(16): 3901-3908.
Jiang et al: "Blockade of the C5a-C5aR axis alleviates lung damage in hDPP4 -transgenic mice infected with MERS-CoV", Emerging Microbes & Infections, vol. 7, No. 1, Apr. 24, 2018.
Johnston, J. et al. "A Phase 1 Multiple-Dose Clinical Study of RA101495, A Subcutaneously Administered Synthetic Macrocyclic Peptide Inhibitor of Complement C5 for Treatment of Paroxysmal Nocturnal Hemoglobinuria." Library of the European Hematology Association, Jun. 9, 2016, 2 pages, [Online] [Retrieved May 11, 2022], Retrieved from the Internet <URL:https://library.ehaweb.org/eha/2016/21st/135360/jeffrey.johnston.a.phase.1.multiple-dose.clinical.study.of.ra101495.a.html>.
Johnston, Jeffrey et al. "A Phase 1 Single-Ascending-Dose Clinical Study of RA101495, a Subcutaneously Administered Synthetic Macrocyclic Peptide Inhibitor of Complement C5 for Treatment of Paroxysmal Nocturnal Hemoglobinuria" 2016, XP055697141, Retrieved from the Internet: URL:https://rapharma.com/wp-content/upload s/2018/12/9-RaPharma-EHA-2016-A 101495-SAD-Poster.odf.
Josephson, K. et al., (2005) Ribosomal synthesis of unnatural peptides, J. Am. Chem. Soc. 127: 11727-11735.
Josephson, K. et al., (2013) "mRNA display: from basic principles to macrocycle drug discovery" Drug Discovery Today, vol. 00, No. 00.
Kairemo E et al., (2010) A nationwide survey of paroxysmal nocturnal haemoglobinuria in Finland. Haematologica 2010;95[suppl. 2]:303:Abstract 0727.
Kay, B.K. et al. (2001) Screening phage-displayed combinatorial peptide libraries, Methods. 24:240-246.
Keefe, A.O. and Szostak, J.W. (2001) Functional proteins from a random-sequence library, Nature 15:715-718.
Keshari et al 2014 (Dec. 2014 ASH abstract) A Novel C5 Complement Inhibitor Protects Against Sepsis-Induced Activation of Complement, Coagulation and Inflammation and Provides Survival Benefit in *E. coli* Sepsis.
Keshari et al 2015 (ASH abstract—Blood 2015 126(765)) Complement C5 Inhibition Blocks the Cytokine Storm and Consumptive Coagulopathy By Decreasing Lipopolysaccharide (LPS) Release in *E. coli* Sepsis.
Korean Office Action for corresponding Korean Application No. 10-2019-7014115 dated Aug. 14, 2020.
Korean Office Action for corresponding Korean Application No. 10-2016-7034788 dated Jun. 5, 2018.
Kourtzelis I., et al., (2010) Complement anaphylatoxin C5a contributes to hemodialysis-associated thrombosis., Blood, 116(4):631-639.
Krisinger, et al., (2014) Thrombin generates previously unidentified C5 products that support the terminal complement Activation pathway. Blood. 120(8):1717-1725.
Langenheim, J.F. et al., (2009) Improving the pharmacokinetics/pharmacodynamics of prolactin, GH, and their antagonists by fusion to a synthetic albumin-binding peptide. J Endocrinol. 203(3):375-87.
Law, S.K., et al. (1997). The internal thioester and the covalent binding properties of the complement proteins C3 and C4. Protein Science. 6:263-274.
Lea, W.A. et al., (2011) Fluorescence polarization assays in small molecule screening. Expert Opin Drug Discov. Jan;6 (1):17-32.
Lee et al. "Pharmacological inhibition of complement C5a-C5a1 receptor signalling ameliorates disease pathology in the hSOD1G93A mouse model of amyotrophic lateral sclerosis" British Journal of Pharmacology, vol. 174, No. 8, Mar. 3, 2017.
Legendre, C.M. et al. (2013) "Terminal Complement Inhibitor Eculizumab in Atypical Hemolytic-Uremic Syndrome" The New England Journal of Medicine, 368(23):2169-2181.

(56) References Cited

OTHER PUBLICATIONS

Levengood, M.R. and Van der Donk, W.A., (2008) Use of lantibiotic synthetases for the preparation of bioactive constrained peptides, Bioorg. and Med. Chem. Lett. 18:3025-3028.
Levi, M. et al., (2013) Sepsis and thrombosis. Seminars in thrombosis and hemostasis 39, 559-66.
Liu, R. et al. (2000). Optimized synthesis of RNA-protein fusions for in vitro protein selection, Methods Enzymol. 318:268-293.
Mackworth-Young, (2004) Antiphospholipid syndrome: multiple mechanisms., Clin Exp Immunol 136:393-401.
Markiewski, et al., (2007) The role of complement in inflammatory diseases from behind the scenes into the spotlight. Am J Pathol. 171: 715-27.
Meri S., (2013) Complement activation in diseases presenting with thrombotic microangiopathy., European Journal of Internal Medicine, 24: 496-502.
Mexican Office Action for corresponding Mexican Application No. MX/a/2016/016449 dated Jul. 20, 2020.
Milletti, F., 2012 Cell-penetrating peptides: classes, origin, and current landscape. Drug Discov Today. Aug;17 (15-16):850-60.
Millward, S.W. et al., (2005) A general route for post-translational cyclization of mRNA display libraries, J. Am. Chem. Soc. 127:14142-14143.
Mollnes, T. E. et al., (2002) Essential role of the C5a receptor in *E coli*-induced oxidative burst and phagocytosis revealed by a novel lepirudin-based human whole blood model of inflammation. Blood 100, 1869-1877.
Morgan, Paul et al. “Complement, a target for therapy in inflammatory and degenerative diseases” Nature Reviews Drug Discovery 14:857-877. {Year: 2015).
Murakami, H. et al. (2006) A highly flexible tRNA acylation method for non-natural polypeptide synthesis, Nat. Methods 3:357-359.
Nakayama H et al., (2016) Eculizumab dosing intervals longer than 17 days may be associated with greater risk of breakthrough hemolysis in patients with paroxysmal nocturnal hemoglobinuria. Biol Pharm Bull.
Nemoto, H. et al., (1997) In vitro virus: bonding of mRNA bearing puromycin at the 3'-terminal end to the C-terminal end of its encoded protein on the ribosome in vitro, FEBS Lett. 414:405-408.
Nguyen A. et al., (2006) The pharmacokinetics of an albumin-binding Fab (AB.Fab) can be modulated as a function of affinity for albumin. Protein Eng Des Sel. 19:291-7.
Nishimura et al (2012) A rare genetic polymorphism in C5 confers poor response to the anti-C5 monoclonal antibody eculizumab by nine japanese patients with PNH. Blood (ASH Annual Meeting Abstracts). 120: Abstract 3197.
Nishimura J-I et al., (2004) Clinical course and flow cytometric analysis of paroxysmal nocturnal hemoglobinuria in the United States and Japan. Medicine 2004;83:193-207.
Nishimura, J. et al., (2014) Genetic variants in C5 and poor response to eculizumab. N Engl J Med. 370: 632-9.
Oliva, B; et al., (1997) An automated classification of the structure of protein loops, J Mol Biol. Mar. 7;266(4):814-30.
Park, Brian “Zilucoplan for Myasthenia Gravis Gets Orphan Drug Designation” Neurology Advisor, Sep. 9, 2019.
Parker, C. et al., (2005) Diagnosis and management of paroxysmal nocturnal hemoglobinuria. Blood. 106: 3699-709.
Parker, C.J., (2007) The pathophysiology of paroxysmal nocturnal hemoglobinuria. Exp Hematol. 35: 523-33.
Parker, C.J., (2012) Paroxysmal nocturnal hemoglobinuria. Curr Opin Hematol. 19: 141-8.
Parker, G.J. et al., (2000) Development of high throughput screening assays using fluorescence polarization: nuclear receptor-ligand-binding and kinase/phosphatase assays. J Biomol Screen. Apr. 2000;5(2):77-88.
PCT Inernational Search Report and Written Opinion, PCT Application No. PCT/US2016/015412, Apr. 22, 2016, nine pages.
PCT International Search Report and Written Opinion, PCT Application No. PCT/US2019/057316, Apr. 2, 2020, 20 pages.
PCT International Search Report and Written Opinion, PCT Application No. PCT/US2020/021330, Sep. 3, 2020, 22 pages.
PCT International Search Report and Written Opinion, PCT Application No. PCT/US2016/065228, Mar. 17, 2017, 18 pages.
PCT International Search Report and Written Opinion, PCT Application No. PCT/US2015/035473, Dec. 4, 2015, 12 pages.
PCT International Search Report and Written Opinion, PCT Application No. PCT/US2018/063719, Mar. 1, 2019, 13 pages.
PCT International Search Report and Written Opinion, PCT Application No. PCT/US2018/050317, Nov. 15, 2018, 10 pages.
PCT International Search Report and Written Opinion, PCT Application No. PCT/US2017/065005, Apr. 24, 2018, 18 pages.
Prystay, L. et al., (2001) Determination of equilibrium dissociation constants in fluorescence polarization. J Biomol Screen. Jun;6(3):141-50.
Pu, J. J. et al., (2011) Paroxysmal nocturnal hemoglobinuria from bench to bedside. Clin Transl Sci. Jun;4{3):219-24.
Quigg RJ., (2003) Complement and the kidney., J Immunol 171:3319-24.
RA Pharmaceuticals, Inc., Protocol, RA101495-01.201: A Phase 2 Multicenter, Open-Label, Uncontrolled Study to Evaluate the Safety, Tolerability, Efficacy, Pharmacokinetics, and Pharmacodynamics of RA101495 in Subjects With Paroxysmal Nocturnal Hemoglobinuria.
RA Pharmaceuticals, Inc., Statistical Analysis Plan, RA101495-01. 201: A Phase 2 Multicenter, Open-Label, Uncontrolled Study to Evaluate the Safety, Tolerability, Efficacy, Pharmacokinetics, and Pharmacodynamics of RA101495 in Subjects With Paroxysmal Nocturnal Hemoglobinuria.
RA Pharmaceuticals. “Phase 2 Safety and Efficacy Study of Zilucoplan (RA101495) to Treat PNH Patients.” ClinicalTrials.gov, Mar. 8, 2017, eight pages, [Online] [Retrieved Apr. 15, 2020], Retrieved from the Internet <URL:https://clinicaltrials.gov/ct2/show/study/NCT03078582>.
Rapharma: “Zilucoplan in Generalized Myasthenia Gravis”, dated Dec. 10, 2018 URL:https://rapharma.com/wp-content/uploads/2018/12/Zilucoplan-in-Generalized-Myasthenia-Gravis-1.pdf.
Ricardo A. et al. 939 Preclinical evaluation of RA101495, a potent cyclic peptide inhibitor of C5 for the treatment of paroxysmal nocturnal hemoglobinuria. 57th Annual Meeting and Exposition. Orlando, FL. Dec. 5-8, 2015.
Ricardo et al 2014 {Dec. 2014 ASH abstract) Development of RA101348, a Potent Cyclic Peptide Inhibitor of C5 for Complement-Mediated Diseases.
Ricardo et al 2015 (Dec. 2015 ASH abstract) Preclinical Evaluation of RA101495, a Potent Cyclic Peptide Inhibitor of C5 for the Treatment of Paroxysmal Nocturnal Hemoglobinuria.
Ricardo et al. “Preclinical evaluation of RA 101495, a potent cyclic peptide inhibitor of C5 for the treatment of paroxysmal nocturnal hemoglobinuria” ASH Meeting 2015, Poster #939. (Year: 2015).
Ricardo et al., “Development of RA101348, a Potent Cyclic Peptide Inhibitor of C5 for Complement-Mediated Diseases”, Dec. 17, 2014 56th ASH Annual Meeting and Exposition. {last updated Dec. 17, 2014) Abstract retrieved from website <URL https://ash.confex.com/ash/2014/webprogram/Paper74528.html>.
Ricklin, Daniel et al. “Complement in Immune and Inflammatory Disorders: Pathophysiological Mechanisms” J. Immunol. 190: 3831-3838. (Year: 2013).
Ripka, A.S. et al., (1998) Synthesis of novel cyclic protease inhibitors using grubbs olefin metathesis. Bioorg Med Chem Lett. 8(4):357-60.
Risitano et al., (2012) The complement receptor 2/factor H fusion protein TT30 protects paroxysmal nocturnal hemoglobinuria ery1hrocytes from complement-mediated hemolysis and C3 fragment. Blood 119(6): 6307-16.
Risseeuw, M.D.P., (2009) Alkylated and bicyclic sugar amino acids: synthesis and applications. Doctoral Thesis, Leiden University. Chapter 1, p. 9-26.
Rittirsch D., et al., (2008) Harmful molecular mechanisms in sepsis. Nature Reviews Immunology 8, 776-87.
Rittirsch, et al., (2012) Role of complement in multiorgan failure. Clin Dev Immunol, 2012:962927.

(56) References Cited

OTHER PUBLICATIONS

Roberts, R.W., and Szostak, J.W. (1997) RNA-peptide fusions for the in vitro selection of peptides and proteins, Proc. Natl. Acad. Sci. USA 94, 12297-12302.
Rock, et al., (2010) The sterile inflammatory response. Annu Rev Immunol. 28:321-342.
Roth et al., (2009) Long-term efficacy of the complement inhibitor eculizumab in cold agglutinin disease., Blood, 113:3885-86.
Rothe, A. et al. (2006) In vitro display technologies reveal novel biopharmaceutics, The FASEB Journal. 20(10):1599-1610.
Rubartelli, et al., (2013) Mechanisms of sterile inflammation. Frontiers in Immunology 4:398-99.
Russian Office Action for corresponding Russian Application No. 2018121615 entitled "Modulators of Complement Activity" dated Mar. 16, 2020.
Russian Office Action for corresponding Russian Application No. 2016147080, dated Dec. 20, 2017.
Russian Office Action for corresponding Russian Application No. 2016147080 dated May 30, 2018.
Salmon, et al., (2002) Complement activation as a mediator of antiphospholipid antibody induced pregnancy loss and thrombosis. Ann Rheum Dis 2002;61{Suppl II):ii46-ii50.
Sando, S. et al., (2007) Unexpected preference of the *E. coli* translation system for the ester bond during incorporation of backbone-elongated substrates, J. Am. Chem. Soc. 129:6180-6186.
Schafmeister and Verdine (2000) An All-Hydrocarbon Cross-Linking System for Enhancing the Helicity and Metabolic Stability of Peptides, J. Am. Chem. Soc., 122 (24), 5891-5892.
Schlippe, et al. (2012) In vitro selection of highly modified cyclic peptides that act as tight binding inhibitors. J Am Chem. 134:10469-77.
Schrezenmeier, H. et al., (2014) Baseline characteristics and disease burden in patients in the International Paroxysmal Nocturnal Hemoglobinuria Registry. Haematologica. 99: 922-9.
Scott et al. (1999) Production of cyclic peptides and proteins in vivo, PNAS. vol. 96 No. 24 p. 13638-13643.
Second Examination Report for corresponding Australian Application No. 2015274482 dated May 10, 2018.
Seebeck, F.P. and Szostak, J.W. (2006) Ribosomal synthesis of dehydroalanine-containing peptides J. Am. Chem. Soc. Jun 7;128(22):7150-1.
Sergeeva, A. et al. (2006). Display technologies: application for the discovery of drug and gene delivery agents, Adv. Drug Deliv. Rev. 58:1622-1654.
Shimizu, Y. et al. (2001) Cell-free translation reconstituted with purified components, Nat. Biotech. 19:751-755.
Singapore Written Opinion for corresponding Singapore Application No. 11201610222U, dated Dec. 28, 2017.
Sjoberg A.T., et al., (2009) Complement activation and inhibition: a delicate balance. Trends in Immunology. 30(2): 83-90.
Smith, A. B. 3rd, et al. (1994) De Novo Design, Synthesis, and X-ray Crystal Structures of Pyrrolinone-Based .beta.-Strand Peplidomimetics, J. Am. Chem. Soc. 116:9947-9962.
Smith, G.P. and Petrenko, V.A., (1997) Phage Display, Chem. Rev. 97:391-410.
Socie' G et al., (1996) Paroxysmal nocturnal haemoglobinura: long-term follow-up and prognostic factors. Lancet 1996;348:573-577.
Sorbera et al: "Taking aim at a fast-moving target: targets to watch for SARS-CoV-2 and COVID-19", Drugs of the Future, vol. 45, No. 4, Jan. 1, 2020.
Stahel et al., (1998) The role of the complement system in traumatic brain injury. Brain Research Reviews, 27: 243-56.
Subtelny et al., (2008) Ribosomal synthesis of N-methyl peptides, J_ Am. Chem. Soc. 130: 6131-6136.
Sun et al: "Treatment With Anti-C5a Antibody Improves the Outcome of H7N9 Virus Infection in African Green Monkeys", Clinical Infectious Diseases, vol. 60, No. 4, Nov. 27, 2014.
Takahashi, T.T et al. (2003) mRNA display: ligand discovery, interaction analysis and beyond, Trends in Biochem. Sci. 28(3):159-165.
Third Examination Report for corresponding Australian Application No. 2015274482 dated Aug. 28, 2018.
Thomas et al., (1996) Inhibition of complement activity by humanized anti-C5 antibody and single-chain Fv. Molecular Immunology. 33(17-18):1389-401.
Tian, W. et al., (2012) Development of novel fluorescence polarization-based assay for studying the B-cateniniTcf4 interaction. J Biomol Screen. Apr;17(4):530-4.
Timmerman, P. et al., (2005) Rapid and quantitative cyclization of multiple peptide loops onto synthetic scaffolds for structural mimicry of protein surfaces, ChemBioChem 6:821-824.
Van de Goot, F., et al., (2009) Acute inflammation is persistent locally in burn wounds: a pivotal role for complement and C-reactive protein. J Burn Care Res 2009, 30:274-280.
Van De Walle Inge et al: "ARGX-117, a therapeutic complement inhibiting antibody targeting C2", Journal of I\llergy and Clinical Immunology, Elsevier, Amsterdam, NL, vol. 147, No. 4, Sep. 11, 2020, p. 1420.
Van den Elsen, J.M.H., (2002) X-ray crystal structure of the C4d fragment of human complement component C4, J. Mol. Biol. 322:1103-1115.
Vogt, (1999) Cleavage of the fifth component of complement and generation of a functionally active C5b6-like complex by human leukocyte elastase. Immunobiology. 201:470-477.
Yamagishi, Y. et al., (2011) Natural product-like macrocyclic N-methyl peptide inhibitors against a ubiquitin ligase uncovered from a ribosome-expressed de novo library. Chemistry & Biology 18:1562-70.
Duda, P. et al., "A phase 1 multiple-dose clinical study of RA101495, a subcutaneously administered synthetic macrocyclic peptide inhibitor of complement C5 for the treatment of myasthenia gravis (MG)," Muscle and Nerve, Sep. 2017, vol. 56, Supp. Supplement 1, pp. S10-S11. Abstract No. 31.
Business Wire, "Ra Pharma Announces Positive Results from Phase 1b Pharmacokinetic Study of Zilucoplan (RA101495 SC) in Patients with Renal Impairment," Sep. 26, 2018, pp. 1-6, [Online] [Retrieved on May 2, 2023] Retrieved from the Internet <URL: https://www.businesswire.com/news/home/20180926005245/en/>.
clinicaltrials.gov, "NCT03030183: Phase 2 Safety and Efficacy Study of Zilucoplan (RA101495) to Treat PNH Patients Who Have an Inadequate Response to Eculizumab," Jan. 24, 2017, pp. 1-7, [Online] [Retrieved on Jun. 20, 2023] Retrieved from the Internet <URL: https://clinicaltrials.gov/ct2/show/NCT03030183?term=RA101495&draw=2&rank=2>.
clinicaltrials.gov, "NCT03078582: Phase 2 Safety and Efficacy Study of Zilucoplan (RA101495) to Treat PNH Patients," Mar. 13, 2017, pp. 1-8, [Online] [Retrieved on Jun. 20, 2023] Retrieved from the Internet <URL: https://clinicaltrials.gov/ct2/show/NCT03078582?term=RA101495&draw=2&rank=3>.
clinicaltrials.gov, "NCT03315130: Safety and Efficacy Study of RA101495 in Subjects With Generalized Myasthenia Gravis," Oct. 18, 2017, pp. 1-9, [Online] [Retrieved on Jun. 20, 2023] Retrieved from the Internet <URL: https://clinicaltrials.gov/ct2/show/NCT03315130>.
clinicaltrials.gov, "NCT04025632: Safety and Efficacy Study of Zilucoplan in Subjects With Immune-Mediated Necrotizing Myopathy," Jul. 19, 2019, pp. 1-9, [Online] [Retrieved on Jun. 20, 2023] Retrieved from the Internet <URL: https://clinicaltrials.gov/ct2/show/NCT04025632?term=RA101495&draw=2&rank=8>.
clinicaltrials.gov, "NCT04115293: Safety, Tolerability, and Efficacy of Zilucoplan in Subjects With Generalized Myasthenia Gravis (RAISE)," Oct. 4, 2019, pp. 1-9, [Online] [Retrieved on Jun. 20, 2023] Retrieved from the Internet <URL: https://clinicaltrials.gov/ct2/show/NCT04115293?term=RA101495&draw=2&rank=6>.
clinicaltrials.gov, "History of Changes for Study: NCT03315130 Safety and Efficacy Study of RA101495 in Subjects With Generalized Myasthenia Gravis," Oct. 18, 2017, pp. 1-4, [Online] [Retrieved on Jun. 20, 2023] Retrieved from the Internet <URL: https://clinicaltrials.gov/ct2/history/NCT03315130?V_1=View#StudyPageTop>.

(56) References Cited

OTHER PUBLICATIONS

Dhillon, S., "Eculizumab: A Review in Generalized Myasthenia Gravis," Drugs, vol. 78, Feb. 12, 2018, pp. 367-376.
Risitano, A.M. et al., "Toward complement inhibition 2.0: Next generation anticomplement agents for paroxysmal nocturnal hemoglobinuria," American Journal of Hematology, vol. 93, Jan. 4, 2018, pp. 564-577.
Wang, S. et al., "Advances in autoimmune myasthenia gravis management," Expert Rev Neurother. 18(7), Jul. 2018, pp. 573-588.
Zorzi, A. et al., "Cyclic peptide therapeutics: past, present and future," Current Opinion in Chemical Biology, vol. 38, Feb. 27, 2017, pp. 24-29.
clinicaltrials.gov, "NCT03315130: Safety and Efficacy Study of RA101495 in Subjects With Generalized Myasthenia Gravis," Aug. 9, 2018, six pages, [Online] Retrieved from the Internet <URL: https://clinicaltrials.gov/ct2/history/NCT03315130?A=27&B=27&C=Side-by-Side#StudyPageTop>.
Howard J. F. et al., "RA101495, A Subcutaneously Administered Peptide Inhibitor of Complement Component 5 (C5) for the Treatment of Generalized Myasthenia Gravis (gMG): Phase 1 Results and Phase 2 Design (S31.006)," Neurology, Apr. 9, 2018, vol. 90, No. 15 Supplement, pp. 1-3.

* cited by examiner

* Sample supplemented with 2% C5-depleted sera to increase signal

INFLAMMATORY DISEASE TREATMENT WITH COMPLEMENT INHIBITORS

CROSS REFERENCE TO RELATED APPLICATIONS

This application claims priority to U.S. Provisional Application No. 62/856,906 filed on Jun. 4, 2019 entitled INFLAMMATORY DISEASE TREATMENT WITH COMPLEMENT INHIBITORS, U.S. Provisional Application No. 62/899,872 filed on Sep. 13, 2019 entitled INFLAMMATORY DISEASE TREATMENT WITH COMPLEMENT INHIBITORS, U.S. Provisional Application No. 62/926,874 filed on Oct. 28, 2019 entitled INFLAMMATORY DISEASE TREATMENT WITH COMPLEMENT INHIBITORS, U.S. Provisional Application No. 62/984,827 filed on Mar. 4, 2020 entitled INFLAMMATORY DISEASE TREATMENT WITH COMPLEMENT INHIBITORS, and French National Patent Application Number FR2002201 filed on Mar. 4, 2020 entitled INFLAMMATORY DISEASE TREATMENT WITH COMPLEMENT INHIBITORS, the contents of each of which are herein incorporated by reference in their entirety.

SEQUENCE LISTING

The present application is being filed along with a Sequence Listing in electronic format. The Sequence Listing file, entitled 2011_1051PCT_SL.txt, was created on Jun. 3, 2020 and is 1,278 bytes in size. The information in electronic format of the Sequence Listing is incorporated herein by reference in its entirety.

BACKGROUND

The vertebrate immune response is comprised of adaptive and innate immune components. While the adaptive immune response is selective for particular pathogens and is slow to respond, components of the innate immune response recognize a broad range of pathogens and respond rapidly upon infection. One such component of the innate immune response is the complement system.

The complement system includes about 20 circulating complement component proteins, synthesized primarily by the liver. Components of this particular immune response were first termed "complement" due to the observation that they complemented the antibody response in the destruction of bacteria. These proteins remain in an inactive form prior to activation in response to infection. Activation occurs by way of a pathway of proteolytic cleavage initiated by pathogen recognition and leading to pathogen destruction. Three such pathways are known in the complement system and are referred to as the classical pathway, the lectin pathway, and the alternative pathway. The classical pathway is activated when an IgG or IgM molecule binds to the surface of a pathogen. The lectin pathway is initiated by the mannan-binding lectin protein recognizing the sugar residues of a bacterial cell wall. The alternative pathway remains active at low levels in the absence of any specific stimuli. While all three pathways differ with regard to initiating events, all three pathways converge with the cleavage of complement component C3. C3 is cleaved into two products termed C3a and C3b. Of these, C3b becomes covalently linked to the pathogen surface while C3a acts as a diffusible signal to promote inflammation and recruit circulating immune cells. Surface-associated C3b forms a complex with other components to initiate a cascade of reactions among the later components of the complement system. Due to the requirement for surface attachment, complement activity remains localized and minimizes destruction to non-target cells.

Pathogen-associated C3b facilitates pathogen destruction in two ways. In one pathway, C3b is recognized directly by phagocytic cells and leads to engulfment of the pathogen. In the second pathway, pathogen associated C3b initiates the formation of the membrane attack complex (MAC). In the first step, C3b complexes with other complement components to form the C5-convertase complex. Depending on the initial complement activation pathway, the components of this complex may differ. C5-convertase formed as the result of the classical complement pathway comprises C4b and C2a in addition to C3b. When formed by the alternative pathway, C5-convertase comprises two subunits of C3b as well as one Bb component.

Complement component C5 is cleaved by either C5-convertase complex into C5a and C5b. C5a, much like C3a, diffuses into the circulation and promotes inflammation, acting as a chemoattractant for inflammatory cells. C5b remains attached to the cell surface where it triggers the formation of the MAC through interactions with C6, C7, C8 and C9. The MAC is a hydrophilic pore that spans the membrane and promotes the free flow of fluid into and out of the cell, thereby destroying it.

An important component of all immune activity is the ability of the immune system to distinguish between self and non-self cells. Pathology arises when the immune system is unable to make this distinction. In the case of the complement system, vertebrate cells express proteins that protect them from the effects of the complement cascade. This ensures that targets of the complement system are limited to pathogenic cells. Many complement-related disorders and diseases are associated with inflammation that leads to or arises from abnormal destruction of self cells by the complement cascade.

There remains a need in the field for compounds and therapeutic methods for addressing complement-related inflammation and associated pathologies. The present disclosure meets this need by providing related compounds and methods of treatment.

SUMMARY

In some embodiments, the present disclosure provides a method of treating a neuromuscular inflammatory indication by administering a complement inhibitor to a subject. The neuromuscular inflammatory indication may include an inflammatory myopathy. The inflammatory myopathy may include Immune-Mediated Necrotizing Myopathy (IMNM). The IMNM may include an IMNM subtype. The IMNM subtype may include one or more of anti-signal recognition particle (Anti-SRP) subtype, Anti-HMG-CoA reductase (Anti-HMGCR) subtype, and antibody negative subtype. One or more indication-related symptoms may be reduced or eliminated in the subject. The one or more indication-related symptoms may include one or more of muscle weakness, chronic muscle inflammation, muscle atrophy and fatty replacement, elevated serum creatine kinase (CK), dysphagia, neck weakness, myalgia, muscle fiber necrosis, and interstitial lung disease. The elevated serum CK may include serum creatine kinase levels greater than 1000 International Units/Liter (IU/L). The inflammatory myopathy may be diagnosed through serological testing, magnetic resonance imaging (MM), and/or tissue biopsy. The serological testing may include detection of a biomarker. The biomarker may include one or more of alanine aminotransferase (ALT), albumin, alkaline phosphatase (ALP), amylase, aspartate aminotransferase (AST), blood urea nitrogen (BUN), calcium, chloride, creatinine, gamma-glutamyl transferase (GGT), glucose, lactate dehydrogenase (LDH), lipase, potassium, sodium, total bilirubin, total protein, hematocrit, hemoglobin, mean corpuscular hemoglobin (MCH), mean corpuscular hemoglobin concentration (MCHC), mean corpuscular volume (MCV), platelet count, red blood cell (RBC) count, white blood cell (WBC) count, basophils, eosinophils, lymphocytes, monocytes, neutrophils, aldolase, C-reactive protein (CRP), CK, coagulation, complement protein, C5 protein, therapeutic agent, zilucoplan, zilucoplan metabolite, and an autoantibody. The autoantibody may bind to SRP, HMG-CoA reductase, four-and-a-half LEVI domain 1 (FHL1), or survival of motor neuron (SMN). The complement inhibitor may be administered in combination with a therapeutic agent and/or therapeutic regimen. The therapeutic agent and/or therapeutic regimen may include one or more of rituximab, a steroid, an immunosuppressive therapy (IST), and an intravenous immunoglobulin therapy. The subject may be treated with a stable dose of a corticosteroid, an immunosuppressant, or an intravenous immunoglobulin (IVIg). The complement inhibitor may include a C5 inhibitor. The complement inhibitor may include a peptide. The peptide may include a synthetic peptide. The peptide may include a macrocyclic peptide. The complement inhibitor may be zilucoplan. A decrease in a primary endpoint may be observed after treatment with the complement inhibitor. The primary endpoint may include reduced CK levels. CK levels may be reduced after 8 weeks of complement inhibitor treatment. Improvement in a secondary endpoint may be observed after treatment with the complement inhibitor. The secondary endpoint may include an improved score from an assessment comprising one or more of Triple Timed Up and Go (3TUG) Testing, Abbreviated Manual Muscle Testing in 8 Groups (MMT8), Physician Global Activity Visual Analogue Scale (VAS) assessment, and Patent Global Activity VAS assessment. Zilucoplan may be administered at a dose of from about 0.1 mg/kg to about 0.3 mg/kg. Zilucoplan may be administered daily. Zilucoplan administration may include self-administration. Zilucoplan may be administered by subcutaneous injection. The subcutaneous injection may include use of a prefilled syringe. The subcutaneous injection may include use of a self-administration device. The subcutaneous injection may include use of a 29-gauge needle. The subcutaneous injection may include use of self-administration device, wherein the self-administration device comprises an auto injection device. The auto injection device may include a prefilled syringe. The prefilled syringe may be a glass syringe. The prefilled syringe may include a fill volume of from about 0.2 ml to about 2 ml. Zilucoplan may be administered as a pharmaceutical composition. The pharmaceutical composition may include an aqueous solution. The pharmaceutical composition may be preservative-free. The subject may be screened prior to zilucoplan administration. The screening may include assessment of CK level. The CK level may be greater than 1000 International Units/Liter (IU/L). The screening may include verification that subject age is between 18 and 75 years old. The screening may include assessment of anti-HMGCR or anti-SRP antibody levels. The screening may include manual muscle testing in at least one proximal limb muscle group. The screening may include assessment of previous IMNM diagnosis. The previous IMNM diagnosis is made according to American College of Rheumatology/European League Against Rheumatism (ACR/EULAR) Response criteria. The screening may include assessment of subject corticosteroid treatment history. The screening may include assessment of subject immunosuppressive therapy treatment history. The screening may include a serum pregnancy test and/or a urine pregnancy test. The subject may be evaluated or monitored for an IMNM characteristic, wherein the IMNM characteristic includes an assessment made by one or more of CK level analysis, Triple Timed Up and Go (3TUG) test, Proximal Manual Muscle Testing (MMT), Physician Global Activity Visual Analogue Scale (VAS) assessment, Patient Global Activity VAS assessment, Health Assessment Questionnaire (HAQ), Myositis Disease Activity Assessment Tool (MDAAT) score analysis, ACR/EULAR Response Criteria assessment, and Functional Assessment of Chronic Illness Therapy (FACIT)-Fatigue scale assessment. Subject evaluation or monitoring may include assessing change in the IMNM characteristic during or after zilucoplan treatment. Treated subject CK levels may be reduced. Treated subject CK levels may be reduced at or before 8 weeks of treatment. Treated subject CK levels may be monitored over the course of zilucoplan treatment. The treatment may be for a neuromuscular indication (e.g., IMNM) and the subject may be evaluated for improvement in one or more of muscle strength, muscle function, and muscle tissue necrosis in response to complement inhibitor (e.g., zilucoplan) administration. One or more of subject muscle strength, subject muscle function, and subject muscle tissue necrosis may be improved with complement inhibitor (e.g., zilucoplan) administration.

In some embodiments, the present disclosure provides a method of evaluating a treatment for IMNM (e.g., any of such treatments described herein) by screening an evaluation candidate for at least one evaluation participation criteria; selecting an evaluation participant; administering the treatment for IMNM to the evaluation participant; and assessing at least one efficacy endpoint. The at least one evaluation participation criteria may include IMNM diagnosis. The at least one evaluation participation criteria may include a specific CK level or threshold. The CK threshold may include a CK level of at least 1000 International Units/Liter (IU/L). Evaluation participant selection may include evaluation candidate manual muscle testing in at least one proximal limb muscle group. The at least one evaluation participation criteria may include evaluation candidate age. Evaluation participant selection may require evaluation candidate age of between 18 and 75 years old. The at least one evaluation participation criteria may include anti-HMGCR autoantibody level and/or anti-SRP autoantibody level. The at least one evaluation participation criteria may include no change in corticosteroid dose received by the evaluation candidate for at least 30 days prior to screening. The at least one evaluation participation criteria may include no change in evaluation candidate immunosuppressive therapy for at least 30 days prior to screening. The at least one evaluation participation criteria may include negative serum and/or pregnancy test results. The evaluation candidate may be screened for at least one serological biomarker. The treatment for IMNM may be administered over an evaluation period. The evaluation period may be from about 1 day to about 8 weeks. The evaluation period may be about 8 weeks or longer. The at least one efficacy endpoint may include treated subject CK level reduction. The at least one efficacy endpoint may include an improvement from baseline score for one or more of 3TUG test, Proximal MMT, Physician Global Activity VAS assessment, Patient Global Activity VAS assessment, HAQ assessment, MDAAT score, ACR/

EULAR Response Criteria assessment, and FACIT-Fatigue scale assessment. The assessment of at least one efficacy endpoint may include serological testing. The serological testing may include biomarker analysis. The biomarker analysis may include detection and/or measurement of one or more of ALT, albumin, ALP, amylase, AST, BUN, calcium, chloride, creatinine, GGT, glucose, LDH, lipase, potassium, sodium, total bilirubin, total protein, hematocrit, hemoglobin, MCH, MCHC, MCV, platelet count, RBC count, WBC count, basophils, eosinophils, lymphocytes, monocytes, neutrophils, aldolase, CRP, CK, coagulation, complement protein, C5 protein, therapeutic agent, zilucoplan, zilucoplan metabolite, and an autoantibody. The assessment of at least one efficacy endpoint may be carried out on one or more occasions after administering the treatment for IMNM. The one or more occasions after administering the treatment for IMNM may include 1 week, 2 weeks, 4 weeks, and/or 8 weeks after administering the treatment for IMNM.

In some embodiments, the present disclosure provides a method of treating IMNM in a subject by administering zilucoplan to the subject and evaluating subject muscle strength, wherein subject muscle strength is evaluated by measuring contraction of a subject muscle. Zilucoplan may be administered by subcutaneous injection. Zilucoplan may be administered daily. Zilucoplan may be administered at a dose of about 10 mg/kg subject body weight. A subject sample may be analyzed for complement activity. The subject sample may be analyzed for C5a level and/or C5b-9 level. The subject sample may be a serum sample. The subject may have or express an anti-HMGCR antibody. Measuring contraction of the subject muscle may be carried out after stimulating contraction of the subject muscle. Stimulating contraction of the subject muscle may be carried out by electrostimulation. Stimulating contraction of the subject muscle may be carried out by stimulating a nerve associated with the subject muscle. The subject muscle may be a gastrocnemius muscle. Measuring contraction of the gastrocnemius muscle may be carried out after electrostimulation of a sciatic nerve of the subject.

In some embodiments, the present disclosure provides a method of treating reduced muscle strength in a subject by administering zilucoplan to the subject and confirming increased subject muscle strength, wherein the increased subject muscle strength is confirmed by measuring contraction of a subject muscle. Zilucoplan may be administered by subcutaneous injection. Zilucoplan may be administered daily. Zilucoplan may be administered at a dose of about 10 mg/kg subject body weight. A subject sample may be analyzed for complement activity. The subject sample may be analyzed for C5a level and/or C5b-9 level. The subject sample may be a serum sample. The subject may have or express an anti-HMGCR antibody. The subject may have or may be suspected of having IMNM. Measuring contraction of the subject muscle may be carried out after stimulating contraction of the subject muscle. Stimulating contraction of the subject muscle may be carried out by electrostimulation. Stimulating contraction of the subject muscle may be carried out by stimulating a nerve associated with the subject muscle. The subject muscle may be a gastrocnemius muscle. Measuring contraction of the gastrocnemius muscle may be carried out after electrostimulation of a sciatic nerve of the subject.

In some embodiments, the present disclosure provides a composition for use in a method of treating IMNM in a subject, wherein the composition includes zilucoplan, the method including administering the composition to the subject and evaluating subject muscle strength, wherein subject muscle strength is evaluated by measuring contraction of a subject muscle. The composition may be administered by subcutaneous injection. The composition may be administered daily. The composition may be administered at a dose sufficient to provide about 10 mg zilucoplan per kg of subject body weight. A subject sample may be analyzed for complement activity. The subject sample may be analyzed for C5a level and/or C5b-9 level. The subject sample may be a serum sample. The subject may have or express an anti-HMGCR antibody. Measuring contraction of the subject muscle may be carried out after stimulating contraction of the subject muscle. Stimulating contraction of the subject muscle may be carried out by electrostimulation. Stimulating contraction of the subject muscle may be carried out by stimulating a nerve associated with the subject muscle. The subject muscle may be a gastrocnemius muscle. Measuring contraction of the gastrocnemius muscle may be carried out after electrostimulation of a sciatic nerve of the subject.

In some embodiments, the present disclosure provides a composition for use in a method of treating reduced muscle strength in a subject, wherein the composition includes zilucoplan, the method including administering the composition to the subject and confirming increased subject muscle strength, wherein the increased subject muscle strength is confirmed by measuring contraction of a subject muscle. The composition may be administered by subcutaneous injection. The composition may be administered daily. The composition may be administered at a dose sufficient to provide about 10 mg zilucoplan per kg of subject body weight. A subject sample may be analyzed for complement activity. The subject sample is analyzed for C5a level and/or C5b-9 level. The subject sample may be a serum sample. The subject may have or express an anti-HMGCR antibody. The subject may have or may be suspected of having IMNM. Measuring contraction of the subject muscle may be carried out after stimulating contraction of the subject muscle. Stimulating contraction of the subject muscle may be carried out by electrostimulation. Stimulating contraction of the subject muscle may be carried out by stimulating a nerve associated with the subject muscle. The subject muscle may be a gastrocnemius muscle. Measuring contraction of the gastrocnemius muscle may be carried out after electrostimulation of a sciatic nerve of the subject.

BRIEF DESCRIPTION OF THE FIGURES

The foregoing and other objects, features and advantages of particular embodiments of the disclosure will be apparent from the following description and illustrations in the accompanying figures.

DETAILED DESCRIPTION

Introduction

Figure 1:
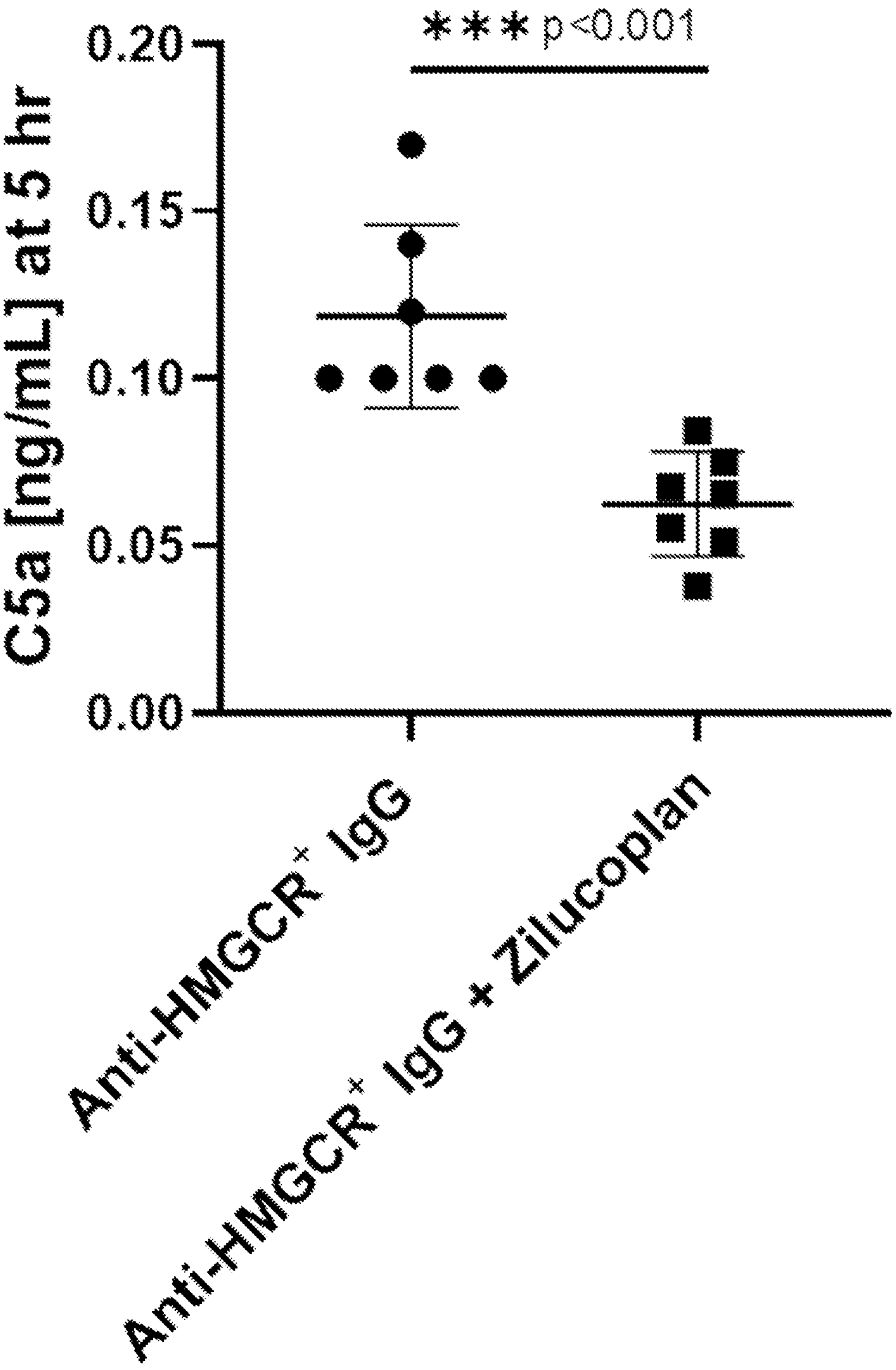
FIG. 1 is a graph showing concentration of human C5a in serum samples derived from C5-deficient mice that were administered human IgG antibodies specific for hydroxy-3-methylglutaryl-CoaA reductase (HMGCR) and normal human serum (NETS). Serum samples were obtained after five hours of treatment with or without zilucoplan.

Embodiments of the present disclosure relate to compounds and compositions for modulating complement activity and related methods of use. Complement activity protects the body from foreign pathogens but can lead to self-cell destruction with elevated activity or poor regulation. Complement modulators may be complement inhibitors, such as zilucoplan. Zilucoplan is a synthetic, macrocyclic peptide that binds complement component 5 (C5) with sub-nanomolar affinity and allosterically inhibits its cleavage into C5a and C5b upon activation of the classical, alternative, or lectin pathways (see, e.g., U.S. Pat. No. 10,106,579, the contents of which are herein incorporated by reference in their entirety).

Included herein are methods of treating complement-related indications by administering complement inhibitors (e.g., zilucoplan). Such complement-related indications include neuromuscular inflammatory indications, including inflammatory myopathies. In some embodiments, the neuromuscular inflammatory indication comprises Immune-Mediated Necrotizing Myopathy (IMNM). Complement inhibitors may be used to treat these conditions by reducing or eliminating the harmful effects of complement-mediated self-tissue destruction associated with overactive complement. Some embodiments of the present disclosure relate to methods of treating IMNM and related muscle weakness in subjects by inhibiting associated complement activity with zilucoplan or compositions thereof and evaluating treated subjects for improvement. These and other embodiments of the disclosure are described in detail below.

I. Compounds and Compositions

In some embodiments, the present disclosure provides compounds and compositions which function to modulate complement activity. Such compounds and compositions may include inhibitors that block complement activation. As used herein, "complement activity" includes the activation of the complement cascade, the formation of cleavage products from a complement component such as C3 or C5, the assembly of downstream complexes following a cleavage event, or any process or event attendant to, or resulting from, the cleavage of a complement component, e.g., C3 or C5. Complement inhibitors may include C5 inhibitors that block complement activation at the level of complement component C5. C5 inhibitors may bind C5 and prevent its cleavage, by C5 convertase, into the cleavage products C5a and C5b. As used herein, "Complement component C5" or "C5" is defined as a complex which is cleaved by C5 convertase into at least the cleavage products, C5a and C5b. "C5 inhibitors," as referred to herein, include any compound or composition that inhibits the processing or cleavage of the pre-cleaved complement component C5 complex or the cleavage products of the complement component C5.

It is understood that inhibition of C5 cleavage prevents the assembly and activity of the cytolytic membrane attack complex (MAC) on glycosylphosphatidylinositol (GPI) adherent protein-deficient erythrocytes. In some cases, C5 inhibitors presented herein may also bind C5b, preventing C6 binding and subsequent assembly of the C5b-9 MAC.

C5 inhibitor compounds may include, but are not limited to, any of those presented in Table 1. References listed and information supporting listed clinical study numbers are incorporated herein by reference in their entirety.

TABLE 1

| C5 inhibitors | | | | | |
|---|---|---|---|---|---|
| Compound | Company | Target | Compound type | Clinical study numbers | References |
| Eculizumab (SOLIRIS ®) | Alexion Pharmaceuticals, Inc. | C5 | Monoclonal antibody directed against C5 protein Inhibits C5 cleavage. | NCT01303952; NCT02093533; NCT01567085; NCT01919346; NCT01895127; NCT01399593; NCT02145182; NCT01106027; NCT02301624; NCT01997229; NCT01892345 | U.S. Pat. No. 6,355,245; 9,732,149; 9,718,880 |
| ALXN1210 | Alexion Pharmaceuticals, Inc. | C5 | Antibody | NCT02598583; NCT02605993; NCT02946463; NCT03056040; NCT02949128 | U.S. Pat. No. 2016/0168237 |
| Tesidolumab/ LFG316 | Novartis | C5 | Antibody | NCT02878616; NCT02763644; NCT01527500; NCT02515942; NCT02534909; NCT01526889 | U.S. Pat. No. 8,241,628; U.S. Pat. No. 8,883,158 |
| ALN-CCS | Alnylam | C5 | Nucleic acid | NCT02352493 | |
| Zimura | Ophthotech | C5 | Nucleic acid | NCT02397954; NCT02686658 | |
| Coversin | Akan | C5 | Protein | NCT02591862 | |
| ALXN1007 | Alexion | C5a | Antibody | NCT02245412; NCT02128269 | |
| IFX-1 | InflaRx | C5a | Antibody | NCT02246595; NCT02866825; NCT03001622 | |

TABLE 1-continued

| C5 inhibitors | | | | | |
|---|---|---|---|---|---|
| Compound | Company | Target | Compound type | Clinical study numbers | References |
| MUBODINA ® | Adienne Pharma | C5 | Antibody | | U.S. Pat. No. 7,999,081 |
| ALXN5500 | Alexion Pharmaceuticals, Inc. | C5 | Antibody | | |
| ISU305 | ISU ABXIS | C5 | Antibody | | |
| Long-acting coversin | Akari | C5 | Protein | | |
| SOBI005 | Swedish Orphan Biovitrum Ab | C5 | Protein | | |
| IFX-2, IFX-3 | InflaRx | C5a | Antibody | | |
| NOX-D21 | Noxxon | C5a | Spiegelmer | | |
| rEV576 | Volution Immunopharma-ceuticals | C5 | Antibody | | Penabad et al., Lupus, 2014 23(12):1324-6 |
| ARC1005 | Novo Nordisk | C5 | Antibody | | |
| SOMAmers | SomaLogic | C5 | Antibody | | |

Peptide-Based Compounds

In some embodiments, C5 inhibitors of the present disclosure are polypeptides. According to the present disclosure, any amino acid-based molecule (natural or non-natural) may be termed a "polypeptide" and this term embraces "peptides," "peptidomimetics," and "proteins." "Peptides" are traditionally considered to range in size from about 4 to about 50 amino acids. Polypeptides larger than about 50 amino acids are generally termed "proteins."

C5 inhibitor polypeptides may be linear or cyclic. Cyclic polypeptides include any polypeptides that have as part of their structure one or more cyclic features such as a loop and/or an internal linkage. In some embodiments, cyclic polypeptides are formed when a molecule acts as a bridging moiety to link two or more regions of the polypeptide. As used herein, the term "bridging moiety" refers to one or more components of a bridge formed between two adjacent or non-adjacent amino acids, non-natural amino acids or non-amino acids in a polypeptide. Bridging moieties may be of any size or composition. In some embodiments, bridging moieties may include one or more chemical bonds between two adjacent or non-adjacent amino acids, non-natural amino acids, non-amino acid residues or combinations thereof. In some embodiments, such chemical bonds may be between one or more functional groups on adjacent or non-adjacent amino acids, non-natural amino acids, non-amino acid residues or combinations thereof. Bridging moieties may include one or more of an amide bond (lactam), disulfide bond, thioether bond, aromatic ring, triazole ring, and hydrocarbon chain. In some embodiments, bridging moieties include an amide bond between an amine functionality and a carboxylate functionality, each present in an amino acid, non-natural amino acid or non-amino acid residue side chain. In some embodiments, the amine or carboxylate functionalities are part of a non-amino acid residue or non-natural amino acid residue.

C5 inhibitor polypeptides may be cyclized through the carboxy terminus, the amino terminus, or through any other convenient point of attachment, such as, for example, through the sulfur of a cysteine (e.g., through the formation of disulfide bonds between two cysteine residues in a sequence) or any side-chain of an amino acid residue. Further linkages forming cyclic loops may include, but are not limited to, maleimide linkages, amide linkages, ester linkages, ether linkages, thiol ether linkages, hydrazone linkages, or acetamide linkages.

In some embodiments, peptides may be synthesized on solid supports (e.g., rink amide resin) via solid phase peptide synthesis (SPPS). SPPS methods are known in the art and may be performed with orthogonal protecting groups. In some embodiments, peptides of the present disclosure may be synthesized via SPPS with Fmoc chemistry and/or Boc chemistry. Synthesized peptides may be cleaved from solid supports using standard techniques.

Peptides may be purified via chromatography [e.g., size exclusion chromatography (SEC) and/or high performance liquid chromatography (HPLC)]. HPLC may include reverse phase HPLC (RP-HPLC). Peptides may be freeze-dried after purification. Purified peptides may be obtained as pure peptide or as a peptide salt. Residual salts making up peptide salts may include, but are not limited to, trifluoroacetic acid (TFA), acetate, and/or hydrochloride. In some embodiments, peptides of the present disclosure are obtained as peptide salts. The peptide salts may be peptide salts with TFA. Residual salts may be removed from purified peptides according to known methods (e.g., through use of desalting columns).

In some embodiments, cyclic C5 inhibitor polypeptides of the present disclosure are formed using a lactam moiety. Such cyclic polypeptides may be formed, for example, by synthesis on a solid support Wang resin using standard Fmoc chemistry. In some cases, Fmoc-ASP(allyl)-OH and Fmoc-LYS(alloc)-OH are incorporated into polypeptides to serve as precursor monomers for lactam bridge formation.

C5 inhibitor polypeptides of the present disclosure may be peptidomimetics. A "peptidomimetic" or "polypeptide mimetic" is a polypeptide in which the molecule contains structural elements that are not found in natural polypeptides (i.e., polypeptides comprised of only the 20 proteinogenic amino acids). In some embodiments, peptidomimetics are capable of recapitulating or mimicking the biological action(s) of a natural peptide. A peptidomimetic may differ in many ways from natural polypeptides, for example through changes in backbone structure or through the presence of amino acids that do not occur in nature. In some cases, peptidomimetics may include amino acids with side chains that are not found among the known 20 proteinogenic amino acids; non-polypeptide-based bridging moieties used to effect cyclization between the ends or internal portions of the molecule; substitutions of the amide bond hydrogen moiety by methyl groups (N-methylation) or other alkyl groups; replacement of a peptide bond with a chemical group or bond that is resistant to chemical or enzymatic treatments; N- and C-terminal modifications; and/or conjugation with a non-peptidic extension (such as polyethylene glycol, lipids, carbohydrates, nucleosides, nucleotides, nucleoside bases, various small molecules, or phosphate or sulfate groups).

As used herein, the term "amino acid" includes the residues of the natural amino acids as well as non-natural amino acids. The 20 natural proteinogenic amino acids are identified and referred to herein by either the one-letter or three-letter designations as follows: aspartic acid (Asp:D), isoleucine threonine (Thr:T), leucine (Leu:L), serine (Ser:S), tyrosine (Tyr:Y), glutamic acid (Glu:E), phenylalanine (Phe:F), proline (Pro:P), histidine (His:H), glycine (Gly:G), lysine (Lys:K), alanine (Ala:A), arginine (Arg:R), cysteine (Cys:C), tryptophan (Trp:W), valine (Val:V), glutamine (Gln:Q) methionine (Met:M), asparagine (Asn:N). Naturally occurring amino acids exist in their levorotary (L) stereoisomeric forms. Amino acids referred to herein are L-stereoisomers except where otherwise indicated. The term "amino acid" also includes amino acids bearing a conventional amino protecting group (e.g. acetyl or benzyloxy carbonyl), as well as natural and non-natural amino acids protected at the carboxy terminus (e.g., as a ($C_1$-$C_6$) alkyl, phenyl or benzyl ester or amide; or as an alpha-methylbenzyl amide). Other suitable amino and carboxy protecting groups are known to those skilled in the art (See for example, Greene, T. W.; Wutz, P. G. M., Protecting Groups In Organic Synthesis; second edition, 1991, New York, John Wiley & sons, Inc., and documents cited therein, the contents of each of which are herein incorporated by reference in their entirety). Polypeptides and/or polypeptide compositions of the present disclosure may also include modified amino acids.

"Non-natural" amino acids have side chains or other features not present in the 20 naturally-occurring amino acids listed above and include, but are not limited to: N-methyl amino acids, N-alkyl amino acids, alpha, alpha substituted amino acids, beta-amino acids, alpha-hydroxy amino acids, D-amino acids, and other non-natural amino acids known in the art (See, e.g., Josephson et al., (2005) J. Am. Chem. Soc. 127: 11727-11735; Forster, A. C. et al. (2003) Proc. Natl. Acad. Sci. USA 100: 6353-6357; Subtelny et al., (2008) J. Am. Chem. Soc. 130: 6131-6136; Hartman, M. C. T. et al. (2007) PLoS ONE 2:e972; and Hartman et al., (2006) Proc. Natl. Acad. Sci. USA 103:4356-4361). Further non-natural amino acids useful for the optimization of polypeptides and/or polypeptide compositions of the present disclosure include, but are not limited to 1,2,3,4-tetrahydroisoquinoline-1-carboxylic acid, 1-amino-2,3-hydro-1H-indene-1-carboxylic acid, homolysine, homoarginine, homoserine, 2-aminoadipic acid, 3-aminoadipic acid, beta-alanine, aminopropionic acid, 2-aminobutyric acid, 4-aminobutyric acid, 5-aminopentanoic acid, 5-aminohexanoic acid, 6-aminocaproic acid, 2-aminoheptanoic acid, 2-aminoisobutyric acid, 3-aminoisobutyric acid, 2-aminopimelic acid, desmosine, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylpentylglycine, naphthylalanine, ornithine, pentylglycine, thioproline, norvaline, tert-butylglycine, phenylglycine, azatryptophan, 5-azatryptophan, 7-azatryptophan, 4-fluorophenylalanine, penicillamine, sarcosine, homocysteine, 1-aminocyclopropanecarboxylic acid, 1-aminocyclobutanecarboxylic acid, 1-aminocyclopentanecarboxylic acid, 1-aminocyclohexanecarboxylic acid, 4-aminotetrahydro-2H-pyran-4-carboxylic acid, (S)-2-amino-3-(1H-tetrazol-5-yl)propanoic acid, cyclopentylglycine, cyclohexylglycine, cyclopropylglycine, η-ω-methyl-arginine, 4-chlorophenylalanine, 3-chlorotyrosine, 3-fluorotyrosine, 5-fluorotryptophan, 5-chlorotryptophan, citrulline, 4-chloro-homophenylalanine, homophenylalanine, 4-aminomethyl-phenylalanine, 3-aminomethyl-phenylalanine, octylglycine, norleucine, tranexamic acid, 2-amino pentanoic acid, 2-amino hexanoic acid, 2-amino heptanoic acid, 2-amino octanoic acid, 2-amino nonanoic acid, 2-amino decanoic acid, 2-amino undecanoic acid, 2-amino dodecanoic acid, aminovaleric acid, and 2-(2-aminoethoxy)acetic acid, pipecolic acid, 2-carboxy azetidine, hexafluoroleucine, 3-Fluorovaline, 2-amino-4,4-difluoro-3-methylbutanoic acid, 3-fluoro-isoleucine, 4-fluoroisoleucine, 5-fluoroisoleucine, 4-ethyl-phenylglycine, 4-isopropyl-phenylglycine, (S)-2-amino-5-azidopentanoic acid (also referred to herein as "X02"), (S)-2-aminohept-6-enoic acid (also referred to herein as "X30"), (S)-2-aminopent-4-ynoic acid (also referred to herein as "X31"), (S)-2-aminopent-4-enoic acid (also referred to herein as "X12"), (S)-2-amino-5-(3-methylguanidino) pentanoic acid, (S)-2-amino-3-(4-(aminomethyl)phenyl)propanoic acid, (S)-2-amino-3-(3-(aminomethyl)phenyl)propanoic acid, (S)-2-amino-4-(2-aminobenzo[d]oxazol-5-yl) butanoic acid, (S)-leucinol, (S)-valinol, (S)-tert-leucinol, (R)-3-methylbutan-2-amine, (S)-2-methyl-1-phenylpropan-1-amine, and (S)—N,2-dimethyl-1-(pyridin-2-yl)propan-1-amine, (S)-2-amino-3-(oxazol-2-yl)propanoic acid, (S)-2-amino-3-(oxazol-5-yl)propanoic acid, (S)-2-amino-3-(1,3,4-oxadiazol-2-yl)propanoic acid, (S)-2-amino-3-(1,2,4-oxadiazol-3-yl)propanoic acid, (S)-2-amino-3-(5-fluoro-1H-indazol-3-yl)propanoic acid, and (S)-2-amino-3-(1H-indazol-3-yl)propanoic acid, (S)-2-amino-3-(oxazol-2-yl) butanoic acid, (S)-2-amino-3-(oxazol-5-yl) butanoic acid, (S)-2-amino-3-(1,3,4-oxadiazol-2-yl) butanoic acid, (S)-2-amino-3-(1,2,4-oxadiazol-3-yl) butanoic acid, (S)-2-amino-3-(5-fluoro-1H-indazol-3-yl) butanoic acid, and (S)-2-amino-3-(1H-indazol-3-yl) butanoic acid, 2-(2'MeOphenyl)-2-amino acetic acid, tetrahydro 3-isoquinolinecarboxylic acid and stereoisomers thereof (including, but not limited, to D and L isomers).

Additional non-natural amino acids that are useful in the optimization of polypeptides or polypeptide compositions of the present disclosure include but are not limited to fluorinated amino acids wherein one or more carbon bound hydrogen atoms are replaced by fluorine. The number of fluorine atoms included can range from 1 up to and including all of the hydrogen atoms. Examples of such amino acids include but are not limited to 3-fluoroproline, 3,3-difluoroproline, 4-fluoroproline, 4,4-difluoroproline, 3,4-difluroproline, 3,3,4,4-tetrafluoroproline, 4-fluorotryptophan, 5-flurotryptophan, 6-fluorotryptophan, 7-fluorotryptophan, and stereoisomers thereof.

Further non-natural amino acids that are useful in the optimization of polypeptides of the present disclosure include but are not limited to those that are disubstituted at the α-carbon. These include amino acids in which the two substituents on the α-carbon are the same, for example α-amino isobutyric acid, and 2-amino-2-ethyl butanoic acid, as well as those where the substituents are different, for example α-methylphenylglycine and α-methylproline. Further the substituents on the α-carbon may be taken together to form a ring, for example 1-aminocyclopentanecarboxylic acid, 1-aminocyclobutanecarboxylic acid, 1-aminocyclohexanecarboxylic acid, 3-aminotetrahydrofuran-3-carboxylic acid, 3-aminotetrahydropyran-3-carboxylic acid, 4-aminotetrahydropyran-4-carboxylic acid, 3-aminopyrrolidine-3-carboxylic acid, 3-aminopiperidine-3-carboxylic acid, 4-aminopiperidinnne-4-carboxylix acid, and stereoisomers thereof.

Additional non-natural amino acids that are useful in the optimization of polypeptides or polypeptide compositions of the present disclosure include but are not limited to analogs of tryptophan in which the indole ring system is replaced by another 9 or 10 membered bicyclic ring system with 0, 1, 2, 3 or 4 heteroatoms independently selected from N, O, or S. Each ring system may be saturated, partially unsaturated, or fully unsaturated. The ring system may be substituted by 0, 1, 2, 3, or 4 substituents at any substitutable atom. Each substituent may be independently selected from H, F, Cl, Br, CN, COOR, CONRR', oxo, OR, NRR'. Each R and R' may be independently selected from H, C1-C20 alkyl, or C1-C20 alkyl-O—C1-20 alkyl.

In some embodiments, analogs of tryptophan (also referred to herein as "tryptophan analogs") may be useful in the optimization of polypeptides or polypeptide compositions of the present disclosure. Tryptophan analogs may include, but are not limited to, 5-fluorotryptophan [(5-F)W], 5-methyl-O-tryptophan [(5-MeO)W], 1-methyltryptophan [(1-Me-W) or (1-Me)W], D-tryptophan (D-Trp), azatryptophan (including, but not limited to 4-azatryptophan, 7-azatryptophan and 5-azatryptophan,) 5-chlorotryptophan, 4-fluorotryptophan, 6-fluorotryptophan, 7-fluorotryptophan, and stereoisomers thereof. Except where indicated to the contrary, the term "azatryptophan" and its abbreviation, "azaTrp," as used herein, refer to 7-azatryptophan.

Modified amino acid residues useful for the optimization of polypeptides and/or polypeptide compositions of the present disclosure include, but are not limited to those which are chemically blocked (reversibly or irreversibly); chemically modified on their N-terminal amino group or their side chain groups; chemically modified in the amide backbone, as for example, N-methylated, D (non-natural amino acids) and L (natural amino acids) stereoisomers; or residues wherein the side chain functional groups are chemically modified to another functional group. In some embodiments, modified amino acids include without limitation, methionine sulfoxide; methionine sulfone; aspartic acid-(beta-methyl ester), a modified amino acid of aspartic acid; N-ethylglycine, a modified amino acid of glycine; alanine carboxamide; and/or a modified amino acid of alanine. Non-natural amino acids may be purchased from Sigma-Aldrich (St. Louis, Mo.), Bachem (Torrance, Calif.) or other suppliers. Non-natural amino acids may further include any of those listed in Table 2 of US patent publication US 2011/0172126, the contents of which are incorporated herein by reference in their entirety.

The present disclosure contemplates variants and derivatives of polypeptides presented herein. These include substitutional, insertional, deletional, and covalent variants and derivatives. As used herein, the term "derivative" is used synonymously with the term "variant" and refers to a molecule that has been modified or changed in any way relative to a reference molecule or starting molecule.

Polypeptides of the present disclosure may include any of the following components, features, or moieties, for which abbreviations used herein include: "Ac" and "NH2" indicate acetyl and amidated termini, respectively; "Nvl" stands for norvaline; "Phg" stands for phenylglycine; "Tbg" stands for tert-butylglycine; "Chg" stands for cyclohexylglycine; "(N-Me)X" stands for the N-methylated form of the amino acid indicated by the letter or three letter amino acid code in place of variable "X" written as N-methyl-X [e.g. (N-Me)D or (N-Me)Asp stand for the N-methylated form of aspartic acid or N-methyl-aspartic acid]; "azaTrp" stands for azatryptophan; "(4-F)Phe" stands for 4-fluorophenylalanine; "Tyr (OMe)" stands for O-methyl tyrosine, "Aib" stands for amino isobutyric acid; "(homo)F" or "(homo)Phe" stands for homophenylalanine; "(2-OMe)Phg" refers to 2-O-methylphenylglycine; "(5-F)W" refers to 5-fluorotryptophan; "D-X" refers to the D-stereoisomer of the given amino acid "X" [e.g. (D-Chg) stands for D-cyclohexylglycine]; "(5-MeO)W" refers to 5-methyl-O-tryptophan; "homoC" refers to homocysteine; "(1-Me-W)" or "(1-Me)W" refers to 1-methyltryptophan; "Nle" refers to norleucine; "Tiq" refers to a tetrahydroisoquinoline residue; "Asp(T)" refers to (S)-2-amino-3-(1H-tetrazol-5-yl)propanoic acid; "(3-Cl-Phe)" refers to 3-chlorophenylalanine; "[(N-Me-4-F)Phe]" or "(N-Me-4-F)Phe" refers to N-methyl-4-fluorophenylalanine; "(m-Cl-homo)Phe" refers to meta-chloro homophenylalanine; "(des-amino)C" refers to 3-thiopropionic acid; "(alpha-methyl)D" refers to alpha-methyl L-aspartic acid; "2Nal" refers to 2-naphthylalanine; "(3-aminomethyl)Phe" refers to 3-aminomethyl-L-phenyalanine; "Cle" refers to cycloleucine; "Ac-Pyran" refers to 4-amino-tetrahydro-pyran-4-carboxylic acid; "(Lys-C16)" refers to N-ε-palmitoyl lysine; "(Lys-C12)" refers to N-ε-lauryl lysine; "(Lys-C10)" refers to N-ε-capryl lysine; "(Lys-C8)" refers to N-ε-caprylic lysine; "[xXylyl(y, z)]" refers to the xylyl bridging moiety between two thiol containing amino acids where x may be m, p or o to indicate the use of meta-, para- or ortho-dibromoxylenes (respectively) to generate bridging moieties and the numerical identifiers, y and z, place the amino acid position within the polypeptide of the amino acids participating in the cyclization; "[cyclo(y,z)]" refers to the formation of a bond between two amino acid residues where the numerical identifiers, y and z, place the position of the residues participating in the bond; "[cyclo-olefinyl(y, z)]" refers to the formation of a bond between two amino acid residues by olefin metathesis where the numerical identifiers, y and z, place the position of the residues participating in the bond; "[cyclo-thioalkyl(y,z)]" refers to the formation of a thioether bond between two amino acid residues where the numerical identifiers, y and z, place the position of the residues participating in the bond; "[cyclo-triazolyl(y,z)]" refers to the formation of a triazole ring between two amino acid residues where the numerical identifiers, y and z, place the position of the residues participating in the bond. "B20" refers to N-ε-(PEG2-γ-glutamic acid-N-α-octadecanedioic acid) lysine [also known as (1S,28S)-1-amino-7,16,25,30-tetraoxo-9,12,18,21-tetraoxa-6,15,24,29-tetraazahexatetracontane-1,28,46-tricarboxylic acid.]

B20

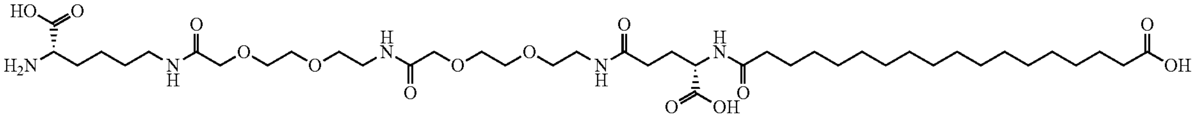

"B28" refers to N-ε-(PEG24-γ-glutamic acid-N-α-hexadecanoyl)lysine.

B28

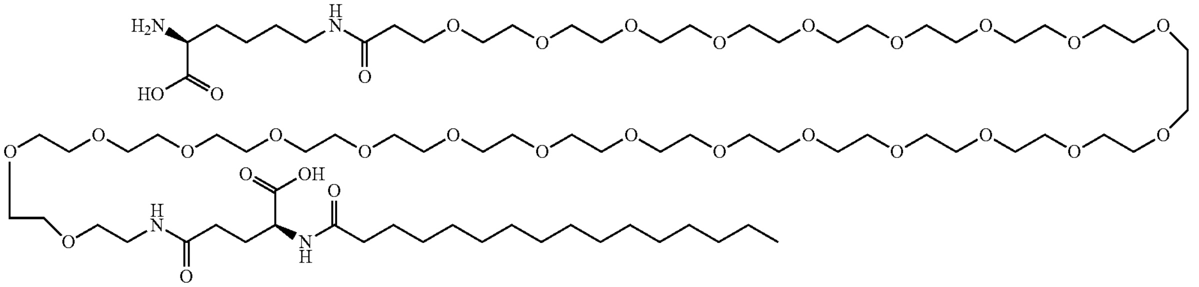

"K14" refers to N-ε-1-(4,4-dimethyl-2,6-dioxocyclohex-1-ylidene)-3-methylbutyl-L-lysine. All other symbols refer to the standard one-letter amino acid code.

Some C5 inhibitor polypeptides include from about 5 amino acids to about 10 amino acids, from about 6 amino acids to about 12 amino acids, from about 7 amino acids to about 14 amino acids, from about 8 amino acids to about 16 amino acids, from about 10 amino acids to about 18 amino acids, from about 12 amino acids to about 24 amino acids, or from about 15 amino acids to about 30 amino acids. In some cases, C5 inhibitor polypeptides include at least 30 amino acids.

Some C5 inhibitors of the present disclosure include a C-terminal lipid moiety. Such lipid moieties may include fatty acyl groups (e.g., saturated or unsaturated fatty acyl groups). In some cases, the fatty acyl group may be a palmitoyl group.

C5 inhibitors having fatty acyl groups may include one or more molecular linkers joining the fatty acids to the peptide. Such molecular linkers may include amino acid residues. In some cases, L-γ glutamic acid residues may be used as molecular linkers. In some cases, molecular linkers may include one or more polyethylene glycol (PEG) linkers. PEG linkers of the present disclosure may include from about 1 to about 5, from about 2 to about 10, from about 4 to about 20, from about 6 to about 24, from about 8 to about 32, or at least 32 PEG units.

C5 inhibitors disclosed herein may have molecular weights of from about 200 g/mol to about 600 g/mol, from about 500 g/mol to about 2000 g/mol, from about 1000 g/mol to about 5000 g/mol, from about 3000 g/mol to about 4000 g/mol, from about 2500 g/mol to about 7500 g/mol, from about 5000 g/mol to about 10000 g/mol, or at least 10000 g/mol.

In some embodiments, C5 inhibitor polypeptides of the present disclosure include zilucoplan (CAS Number: 1841136-73-9). The core amino acid sequence of zilucoplan ([cyclo(1,6)]Ac—K—V-E-R—F-D-(N-Me)D-Tbg-Y-aza-Trp-E-Y—P-Chg-K; SEQ ID NO: 1) includes 15 amino acids (all L-amino acids), including 4 non-natural amino acids [N-methyl-aspartic acid or "(N-Me)D", tert-butylglycine or "Tbg", 7-azatryptophan or "azaTrp", and cyclohexylglycine or "Chg"]; a lactam bridge between K1 and D6 of the polypeptide sequence; and a C-terminal lysine reside with a modified side chain, forming a N-ε-(PEG24-γ-glutamic acid-N-α-hexadecanoyl)lysine residue (also referred to herein as "B28"). The C-terminal lysine side chain modification includes a polyethylene glycol (PEG) spacer (PEG24), with the PEG24 being attached to an L-γ glutamic acid residue that is derivatized with a palmitoyl group.

The free acid form of zilucoplan has a molecular formula of $C_{172}H_{278}N_{24}O_{55}$, a molecular weight of 3562.23 Daltons (Da), and an exact mass of 3559.97 amu. The tetra sodium form of zilucoplan has a molecular formula of $C_{172}H_{278}N_{24}O_{55}Na_4$. The chemical structure of the sodium salt form of zilucoplan is shown in structure I:

Structure I

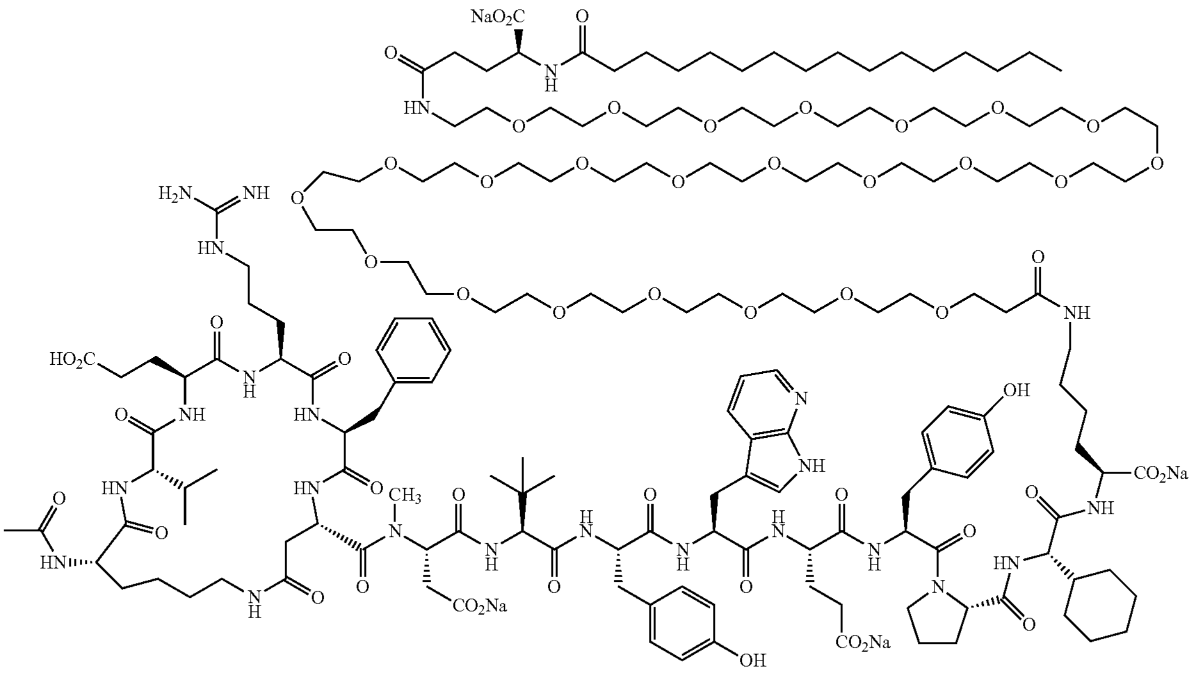

The four sodium ions in the structure are shown associated with designated carboxylates, but they may be associated with any of the acidic groups in the molecule. The zilucoplan drug substance is typically provided as the sodium salt form and is lyophilized.

In some embodiments, the present disclosure includes variants of zilucoplan. In some zilucoplan variants, the C-terminal lysine side chain moiety may be altered. In some cases, the PEG24 spacer (having 24 PEG subunits) of the C-terminal lysine side chain moiety may include fewer or additional PEG subunits. In other cases, the palmitoyl group of the C-terminal lysine side chain moiety may be substituted with another saturated or unsaturated fatty acid. In further cases, the L-γ glutamic acid linker of the C-terminal lysine side chain moiety (between PEG and acyl groups) may be substituted with an alternative amino acid or non-amino acid linker.

In some embodiments, C5 inhibitors may include active metabolites or variants of zilucoplan. Metabolites may include ω-hydroxylation of the palmitoyl tail. Such variants may be synthesized or may be formed by hydroxylation of a zilucoplan precursor.

In some embodiments, zilucoplan variants may include modifications to the core polypeptide sequence in zilucoplan that may be used in combination with one or more of the cyclic or C-terminal lysine side chain moiety features of zilucoplan. Such variants may have at least 50%, at least 55%, at least 65%, at least 70%, at least 80%, at least 85%, at least 90%, or at least 95% sequence identity to the core polypeptide sequence of (SEQ ID NO: 1).

In some cases, zilucoplan variants may be cyclized by forming lactam bridges between amino acids other than those used in zilucoplan.

In some embodiments, C5 inhibitors of the present disclosure may include any of those listed in Table 1 of United States Publication Number US 2017/0137468, the contents of which are herein incorporated by reference in their entirety.

C5 inhibitors of the present disclosure may be developed or modified to achieve specific binding characteristics. Inhibitor binding may be assessed by determining rates of association and/or dissociation with a particular target. In some cases, compounds demonstrate strong and rapid association with a target combined with a slow rate of dissociation. In some embodiments, C5 inhibitors of the present disclosure demonstrate strong and rapid association with C5. Such inhibitors may further demonstrate slow rates of dissociation with C5.

C5 protein-binding C5 inhibitors disclosed herein, may bind to C5 complement protein with an equilibrium dissociation constant ($K_D$) of from about 0.001 nM to about 0.01 nM, from about 0.005 nM to about 0.05 nM, from about 0.01 nM to about 0.1 nM, from about 0.05 nM to about 0.5 nM, from about 0.1 nM to about 1.0 nM, from about 0.5 nM to about 5.0 nM, from about 2 nM to about 10 nM, from about 8 nM to about 20 nM, from about 15 nM to about 45 nM, from about 30 nM to about 60 nM, from about 40 nM to about 80 nM, from about 50 nM to about 100 nM, from about 75 nM to about 150 nM, from about 100 nM to about 500 nM, from about 200 nM to about 800 nM, from about 400 nM to about 1,000 nM or at least 1,000 nM.

In some embodiments, C5 inhibitors of the present disclosure block the formation or generation of C5a from C5. In some case, formation or generation of C5a is blocked following activation of the alternative pathway of complement activation. In some cases, C5 inhibitors of the present disclosure block the formation of the membrane attack complex (MAC). Such MAC formation inhibition may be due to C5 inhibitor binding to C5b subunits. C5 inhibitor binding to C5b subunits may prevent C6 binding, resulting in blockage of MAC formation. In some embodiments, this MAC formation inhibition occurs after activation of the classical, alternative, or lectin pathways.

C5 inhibitors of the present disclosure may be synthesized using chemical processes. In some cases, such synthesis eliminates risks associated with the manufacture of biological products in mammalian cell lines. In some cases, chemical synthesis may be simpler and more cost-effective than biological production processes.

In some embodiments, C5 inhibitor (e.g., zilucoplan and/ or an active metabolite or variant thereof) compositions may be pharmaceutical compositions that include at least one pharmaceutically acceptable excipient. In some embodiments, the pharmaceutically acceptable excipient may include at least one of a salt and a buffering agent. The salt may be sodium chloride. The buffering agent may be sodium phosphate. Sodium chloride may be present at a concentration of from about 0.1 mM to about 1000 mM. In some cases, sodium chloride may be present at a concentration of from about 25 mM to about 100 mM. Sodium phosphate may be present at a concentration of from about 0.1 mM to about 1000 mM. In some cases, sodium phosphate is present at a concentration of from about 10 mM to about 100 mM.

In some embodiments, C5 inhibitor (e.g., zilucoplan and/ or an active metabolite or variant thereof) compositions may include from about 0.01 mg/mL to about 4000 mg/mL of a C5 inhibitor. In some cases, C5 inhibitors are present at a concentration of from about 1 mg/mL to about 400 mg/mL.

Zilucoplan binds to C5 and inhibits cleavage of C5 by canonical complement pathway convertases as described in International Publication Number WO2018106859, the contents of which are herein incorporated by reference in their entirety. Zilucoplan additionally binds C5b, preventing the formation of the membrane attack complex induced by non-canonical cleavage of C5. Zilucoplan binding and inhibitory activities are not affected by the presence of clinically-relevant human C5 polymorphisms (including p.R885>H/C). Unlike eculizumab, an anti-C5 monoclonal antibody inhibitor, zilucoplan does not bind to surface-bound C5b-9 or soluble membrane attack complex (sCSb-9).

Isotopic Variations

Compounds of the present disclosure may include one or more atoms that are isotopes. As used herein, the term "isotope" refers to a chemical element that has one or more additional neutrons. In some embodiments, compounds of the present disclosure may be deuterated. As used herein, the term "deuterated" refers to a substance that has had one or more hydrogen atoms replaced by deuterium isotopes. Deuterium isotopes are isotopes of hydrogen. The nucleus of hydrogen contains one proton while deuterium nuclei contain both a proton and a neutron. Compounds and compositions of the present disclosure may be deuterated in order to change a physical property, such as stability, or to allow for use in diagnostic and experimental applications.

II. Methods and Uses

In some embodiments, the present disclosure provides methods related to using and evaluating compounds and compositions for therapeutic treatment of various therapeutic indications. Some methods include modulating complement activity using compounds and/or compositions described herein. In some embodiments, the present disclosure provides methods of treating IMNM with zilucoplan and evaluating such treatments.

Therapeutic Indications

In some embodiments, methods of the present disclosure include methods of treating therapeutic indications using compounds and/or compositions disclosed herein. As used herein, the term "therapeutic indication" refers to any symptom, condition, disorder, or disease that may be alleviated, stabilized, improved, cured, or otherwise addressed by some form of treatment or other therapeutic intervention (e.g., through complement inhibitor administration). Therapeutic indications may include, but are not limited to, inflammatory indications, wounds, injuries, autoimmune indications, vascular indications, neurological indications, kidney-related indications, ocular indications, cardiovascular indications, pulmonary indications, and pregnancy-related indications. Therapeutic indications associated with complement activity and/or dysfunction are referred to herein as "complement-related indications." In some embodiments, methods of the present disclosure may include treating complement-related indications by administering compounds and/or compositions disclosed herein (e.g., complement inhibitor compounds).

In some embodiments, complement inhibitor compounds may be useful in the treatment of complement-related indications where complement activation leads to progression of a disease, disorder and/or condition. Such complement-related indications may include, but are not limited to inflammatory indications, wounds, injuries, autoimmune indications, vascular indications, neurological indications, kidney-related indications, ocular indications, cardiovascular indications, pulmonary indications, and pregnancy-related indications. Complement-related indications may include, but are not limited to, any of those listed in U.S. Pat. No. 10,106,579, the contents of which are herein incorporated by reference in their entirety.

Complement inhibitor compounds and compositions may be useful in the treatment of infectious diseases, disorders and/or conditions, for example, in a subject having an infection. In some embodiments, subjects having an infection or that are at risk of developing sepsis or a septic syndrome may be treated with complement inhibitors described herein. In some cases, complement inhibitor compounds may be used in the treatment of sepsis.

Complement inhibitor compounds and compositions may also be administered to improve the outcome of clinical procedures wherein complement inhibition is desired. Such procedures may include, but are not limited to grafting, transplantation, implantation, catheterization, intubation and the like. In some embodiments, complement inhibitor compounds and compositions are used to coat devices, materials and/or biomaterials used in such procedures. In some embodiments, the inner surface of a tube may be coated with compounds and compositions to prevent complement activation within a bodily fluid that passes through the tube, either in vivo or ex vivo, e.g., extracorporeal shunting, e.g., dialysis and cardiac bypass.

As used herein the terms "treat," "treatment," and the like, refer to relief from or alleviation of pathological processes. In the context of the present disclosure insofar as it relates to any of the other conditions recited herein below, the terms "treat," "treatment," and the like mean to relieve or alleviate at least one symptom associated with such condition, or to slow or reverse the progression or anticipated progression of such condition.

By "lower" or "reduce" in the context of a disease marker or symptom is meant a significant decrease in such a level, often statistically significant. The decrease may be, for example, at least 10%, at least 20%, at least 30%, at least 40% or more, and is preferably down to a level accepted as within the range of normal for an individual without such a disorder.

By "increase" or "raise" in the context of a disease marker or symptom is meant a significant rise in such level, often statistically significant. The increase may be, for example, at least 10%, at least 20%, at least 30%, at least 40% or more, and is preferably up to a level accepted as within the range of normal for an individual without such disorder.

Efficacy of treatment or amelioration of disease can be assessed, for example by measuring disease progression, disease remission, symptom severity, reduction in pain, quality of life, dose of a medication required to sustain a treatment effect, level of a disease marker or any other measurable parameter appropriate for a given disease being treated or targeted for prevention. It is well within the ability of one skilled in the art to monitor efficacy of treatment or prevention by measuring any one of such parameters, or any combination of parameters. In connection with the administration of a polypeptide or pharmaceutical composition thereof, "effective against" a disease or disorder indicates that administration in a clinically appropriate manner results in a beneficial effect for at least a fraction of patients, such as an improvement of symptoms, a cure, a reduction in disease load, reduction in tumor mass or cell numbers, extension of life, improvement in quality of life, a reduction in the need for blood transfusions or other effect generally recognized as positive by medical doctors familiar with treating the particular type of disease or disorder.

A treatment or preventive effect is evident when there is a significant improvement, often statistically significant, in one or more parameters of disease status, or by a failure to worsen or to develop symptoms where they would otherwise be anticipated. As an example, a favorable change of at least 10% in a measurable parameter of disease, and preferably at least 20%, 30%, 40%, 50% or more may be indicative of effective treatment. Efficacy for a given compound or composition may also be judged using an experimental animal model for the given disease as known in the art. When using an experimental animal model, efficacy of treatment is evidenced when a statistically significant modulation in a marker or symptom is observed.

Compounds of the present disclosure and additional therapeutic agents can be administered in combination. Such combinations may be in the same composition, or the additional therapeutic agents can be administered as part of a separate composition or by another method described herein.

In some embodiments, the present disclosure provides methods of inhibiting C5 activity in a tissue by contacting the tissue with a tissue-penetrating C5 inhibitor. As used herein, the term "tissue-penetrating" refers to a property characterized by tissue permeability. Agents with enhanced tissue-penetration may demonstrate better distribution in tissues when compared to agents with less or no tissue-penetration. Tissue penetration may be assessed by ability to cross basement membranes. As used herein, the term "basement membrane" refers to an extracellular matrix (ECM) protein layer separating endothelial cells from underlying tissues. Tissue penetration assessments may be done in vivo or in vitro and may include the use of basement membrane models. Such models may include measuring compound diffusion across artificial basement membranes. Such models may include the use of upper and lower reservoirs separated by an artificial basement membrane. Artificial basement membranes may include any of the ECM gel membranes described in Arends, F. et al. 2016. IntechOpen, DOI: 10.5772/62519, the contents of which are herein incorporated by reference in their entirety. ECM gel membranes may be prepared to include matrix components mimicking those found in the basal lamina of neuromuscular junctions. In some models, compounds being tested are introduced to upper reservoirs and compound diffusion is detected in lower reservoirs.

Tissue penetration assessment may include visual assessments e.g., through use of fluorescent labels to visualize analyte movement across basement membranes. Some assessments may include biochemical analysis of samples obtained from the penetrated side of a basement membrane.

In some embodiments, compound permeability may be determined using quantitative whole body analysis (QWBA). QWBA is a form of analysis that uses radiography to assess distribution of radiolabeled analytes. In some embodiments, radiolabeled compounds are administered to subjects and tissue distribution of the compounds is analyzed over time.

Tissue-penetrating C5 inhibitors may be polypeptides. Tissue-penetrating C5 inhibitors may include zilucoplan. Contacting tissues with the tissue-penetrating C5 inhibitors may include administering tissue-penetrating C5 inhibitors to tissues as part of a formulation. Such formulations may be administered by subcutaneous injection. Tissue-penetrating C5 inhibitors may be able to penetrate basement membranes. Basement membrane permeability of polypeptide tissue-penetrating C5 inhibitors may be greater than basement membrane permeability of larger proteins, such as antibodies. Such advantages may be due to restrictively large size of proteins and antibodies. Zilucoplan basement membrane permeability may be from about 3-fold to about 5-fold greater than basement membrane permeability of eculizumab, offering advantages over eculizumab for inhibiting C5 activity in tissues and treating related complement-related indications. In some embodiments, zilucoplan permeability enhances distribution in one or more of lung, heart, muscle, small intestine, large intestine, spleen, liver, bone, stomach, lymph node, fat, brain, pancreas, testes, and thymus, in comparison to eculizumab.

Polypeptide-based C5 inhibitors (e.g., zilucoplan and/or active metabolites or variants thereof) may be used to treat complement-related indications (e.g., IMNM) benefiting from rapid and/or enhanced inhibitor tissue distribution. The tissue may include muscle and/or neuromuscular junction (NMJ). Polypeptide inhibitors (e.g., zilucoplan) may provide superior penetration into muscle and/or NMJ compared to antibodies based on smaller size and/or favorable charge profile. Such penetration may lead to faster relief from overactive complement. Further, polypeptide inhibitor (e.g., zilucoplan) penetration may stabilize and/or improve NMJ membrane potential by preventing MAC pore formation. Accordingly, safety factor at the NMJ may be improved. The term "safety factor" refers to excess transmitter levels released after nerve impulse that ensure neuromuscular transmission effectiveness under physiological stress. The excess is the amount beyond that required to trigger muscle fiber action potential and contributes to membrane potential restoration.

In some embodiments, the present disclosure provides methods of treating complement-related indications in subjects by administering zilucoplan in combination with other therapeutic agents. Cyclosporine A is a known immunosuppressive agent, inhibitor of organic anion transporting polypeptide (OATP) 1B1 and OATP1B3 and is a potential comedication in PNH and other complement-related indications. In some embodiments, cyclosporine A and zilucoplan may be administered in combination to subjects with complement-related indications. Cyclosporine A and zilucoplan may be administered in overlapping dosage regimens. Other immunosuppressive agents that may be administered in combination with or in overlapping dosage regiments with zilucoplan may include, but are not limited to, azathioprine, cyclosporine, mycophenolate mofetil, methotrexate, tacrolimus, cyclophosphamide, and rituximab.

In some embodiments, the present disclosure provides methods of treating complement-related indications in subjects by administering zilucoplan in combination with neonatal Fc receptor (FcRN) inhibitor treatments. FcRN inhibitor treatments may be used to treat autoimmune diseases that include autoantibody-mediated tissue destruction. FcRN inhibitor treatments may include intravenous immunoglobulin (IVIg) treatment, which reduces the half-life of IgG antibodies by overwhelming the Fc recycling mechanism with large doses of immunoglobulin. Some FcRN inhibitor treatments may include administration of DX-2504 or funtionally equivalent variants thereof, e.g., DX-2507, which includes modifications to reduce aggregation and improve manufacturability (described in Nixon, A. E. et al. 2015. Front Immunol. 6:176). DX-2504 is an inhibitor of FcRN recycling. By inhibiting FcRN, DX-2504 inhibits Fc-mediated recycling, thereby reducing the half-life of IgG antibodies. Administration of DX-2504 may also be used in models of IVIg treatment. In some embodiments, zilucoplan may be administered to treat complement-related indications (e.g., IMNM) in overlapping dosage regimens with FcRN inhibitor treatments. The FcRN inhibitor treatments may include DX-2504 (or DX-2507) administration and/or IVIg treatment.

Inflammatory Indications

Therapeutic indications that may be addressed with compounds and/or compositions of the present disclosure may include inflammatory indications. As used herein, the term "inflammatory indication" refers to therapeutic indications that involve immune system activation. Inflammatory indications may include complement-related indications. Inflammation may be upregulated during the proteolytic cascade of the complement system. Although inflammation may have beneficial effects, excess inflammation may lead to a variety of pathologies (Markiewski et al. 2007. Am J Pathol. 17: 715-27). In some embodiments, complement inhibitor compounds and compositions of the present disclosure may be used to treat, prevent, or delay development of inflammatory indications.

Inflammatory indications may include, but are not limited to, Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Acute antibody-mediated rejection following organ transplantation, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune pancreatitis, Autoimmune retinopathy, Autoimmune thrombocytopenic purpura (ATP), Autoimmune thyroid disease, Autoimmune urticaria, Axonal & neuronal neuropathies, Bacterial sepsis and septic shock, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal osteomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Diabetes Type I, Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Glomerulonephritis, Goodpasture's syndrome, Granulomatosis with Polyangiitis (GPA) see Wegener's, Graves' disease, Guillain-Barre syndrome, Hashimoto's encephalitis, Hashimoto's thyroiditis, Hemolytic anemia (including atypical hemolytic uremic syndrome and plasma therapy-resistant atypical hemolytic-uremic syndrome), Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Insulin-dependent diabetes (type1), Interstitial cystitis, Juvenile arthritis, Juvenile diabetes, Kawasaki syndrome, Lambert-Eaton syndrome, Large vessel vasculopathy, Leukocytoclastic vasculitis, Lichen planus, Lichen sclerosus, Ligneous conjunctivitis, Linear IgA disease (LAD), Lupus (SLE), Lyme disease, Meniere's disease, Microscopic polyangiitis, Mixed connective tissue disease (MCTD), Mooren's ulcer, Mucha-Habermann disease, Multiple endocrine neoplasia syndromes, Multiple sclerosis, Multifocal motor neuropathy, Myositis, Myasthenia gravis, Narcolepsy, Neuromyelitis optica (Devic's), Neutropenia, Ocular cicatricial pemphigoid, Optic neuritis, Osteoarthritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polyendocrinopathies, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic Pulmonary fibrosis, Pyoderma gangrenosum, Pure red cell aplasia, Raynauds phenomenon, Reactive arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Shiga-Toxin producing *Escherichia Coli* Hemolytic-Uremic Syndrome (STEC-HUS), Sjogren's syndrome, Small vessel vasculopathy, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Tubular autoimmune disorder, Ulcerative colitis, Undifferentiated connective tissue disease (UCTD), Uveitis, Vesiculobullous dermatosis, Vasculitis, Vitiligo, and Wegener's granulomatosis (also known as Granulomatosis with Polyangiitis (GPA)).

Neuromuscular Inflammatory Indications

Therapeutic indications that may be addressed with compounds and/or compositions of the present disclosure may include neuromuscular inflammatory indications. As used herein, the term "neuromuscular inflammatory indication" refers to inflammatory indications that involve components of the nervous system, muscular system, and areas where these two systems overlap or integrate. Neuromuscular inflammatory indications may include complement-related indications. Neuromuscular inflammation may be upregulated during the proteolytic cascade of the complement system. Although inflammation may have beneficial effects, excess inflammation may lead to a variety of pathologies (Markiewski et al. 2007. Am J Pathol. 17: 715-27). In some embodiments, complement inhibitor compounds and compositions of the present disclosure may be used to treat, prevent, or delay development of neuromuscular inflammatory indications.

In some embodiments, the present disclosure provides a method of treating a neuromuscular inflammatory indication by administering a complement inhibitor to a subject. The neuromuscular inflammatory indication may include an inflammatory myopathy. As used herein, the term "inflammatory myopathy" refers to any disease or disorder involving chronic muscle inflammation and corresponding weakness. The inflammatory myopathy may include Immune-Mediated Necrotizing Myopathy (IMNM).

IMNM is a rare, severe, inflammatory myopathy characterized by proximal limb weakness; markedly elevated serum creatine kinase (CK) levels; the presence of anti-SRP or anti-HMGCR auto-antibodies in serum; and paucicellular necrosis with prominent terminal complement deposition on muscle biopsy. IMNM is a relatively newly defined inflammatory myopathy, a group of diseases that also includes polymyositis, dermatomyositis, inclusion body myositis, and other, less well-defined myopathies. Previously, all patients who presented with proximal limb weakness and elevated CK, in the absence of skin involvement were classified as having polymyositis. However, many patients with the diagnostic label of 'polymyositis' were subsequently found to have distinctive findings on muscle biopsy as described above (Amato and Griggs. 2003. Neurology. 288-9), leading to their separate classification as 'necrotizing myopathy'. Subsequently, autoantibodies against HMGCR, a key enzyme in cholesterol biosynthesis, and SRP, a ubiquitous ribonucleoprotein involved in delivery of newly synthesized proteins to the endoplasmic reticulum, were found to be associated with this new entity which led to its designation as IMNM (see Pinal Fernandez, I. et al., 2018. Current Rheumatology Reports. 20: 21, the contents of which are herein incorporated by reference in their entirety).

The prevalence of IMNM is estimated at approximately 16,000 patients in the US, Europe and Japan (Pinal-Fernandez 2018, Smoyer-Tomic 2012, Anquetil 2019). The disease is more common in women than in men. It does not show any clear racial predominance amongst Caucasians, Black or Asian populations, except for the association of anti-HMGCR positive IMNM with statin use, which is higher in non-Asian populations. The mean age at presentation is approximately 40 to 55 years old (Pinal-Fernandez 2018).

Clinically, IMNM presents with prominent proximal limb weakness due to the myopathy and can progress rapidly to disabling muscle atrophy. Although the clinicopathological presentation is generally similar among patients with anti-SRP and anti-HMGCR antibodies, there are subtle differences that have emerged since reliable and validated assays for these pathogenic autoantibodies have become more widely available. Patients with anti-SRP antibodies usually experience more severe weakness; more frequent neck weakness, dysphagia and respiratory insufficiency; and more prominent muscle atrophy. Moreover, clinically manifest cardiac involvement occurs in approximately 15% of patients with anti-SRP autoantibodies. In contrast, extra-muscular manifestations are rare in patients with anti-HMGCR autoantibodies (Pinal-Fernandez 2018).

Muscle biopsy, muscle Mill and EMG are often used for narrowing of the differential diagnosis and further characterization of patients with IMNM. However, based on criteria set forth by the 224$^{th}$ European Neuromuscular Center (ENMC) International Workshop which included experts from Europe, the US, and Japan, these additional investigations are not required to confirm the diagnosis of IMNM in patients with the characteristic clinical picture of high CK levels and positive anti-SRP or anti-HMGCR autoantibodies (Allenbach, Y. et al. 2018. Neuromuscul Disord. 28(1): 87-99). If a muscle biopsy is performed, findings typically include myofiber necrosis and, in contrast to other inflammatory myopathies, only small numbers of infiltrating inflammatory cells. Moreover, with specific staining, prominent complement activation and diffuse deposition of the C5b-9 membrane attack complex (MAC) are observed, the pattern of which is distinct from other inflammatory myopathies (Cong 2014). Mill may demonstrate fatty replacement of muscle tissue which begins early after onset of IMNM (Pinal-Fernandez 2018), and EMG may confirm the presence of a myopathic pattern, and rules out other causes of muscle weakness.

IMNM patients invariably exhibit the greatest elevation of serum CK levels seen among all forms of myositis, and serum CK levels correlate well with disease activity. Unlike in myopathies with less prominent tissue destruction, plasma CK levels in IMNM directly reflect the degree of myocyte necrosis due to ongoing release of this enzyme from injured skeletal muscle cells. Therefore, CK can be used for routine clinical follow-up and to evaluate treatment response in patients with IMNM, in addition to clinical measures such as standardized muscle strength testing. Specifically, CK levels may increase prior to manifestation or deterioration of clinical weakness, and a decline in CK levels is often the first sign of treatment response after treatment initiation while muscle regeneration and recovery of muscle strength may follow weeks to months later (Pinal-Fernandez 2018).

Given the rapidly progressing symptoms and muscle pathology in IMNM, timely diagnosis and initiation of treatment are critical to help reduce long-term disability and improve prognosis. While most immune mediated myopathies, to varying degrees, are responsive to non-specific immunosuppressive therapy, there are currently no FDA approved treatments for IMNM, and no randomized trials have been performed. The ENMC treatment recommendations identify corticosteroids as first line therapy in combination with, or rapidly followed by, an immunosuppressive agent such as methotrexate depending on disease severity. Intravenous immunoglobulin (IVIg) and rituximab are also increasingly used as first line therapy (Allenbach and Benveniste 2018).

Despite the treatments outlined above, disabling relapses and progressive muscle damage often continue, with particularly poor prognosis and permanent disability observed in younger patients and those with anti-SRP autoantibodies (Allenbach and Benveniste 2018). Therefore, a high unmet medical need exists for additional treatment options for patients with IMNM.

There is substantial pre-clinical and clinical evidence supporting a role for the terminal complement cascade in the pathogenesis of IMNM (Allenbach, Y et al. Curr. Opin. Rheumatol. 2018, 30(6), 655-663). 80% of anti-SRP and 100% of anti-HMGCR autoantibodies are of the IgG1 immunoglobulin subclass which efficiently activates the classical pathway of complement (Anquetil, C et al. Autoimmun. Rev. 2019, 18(3), 223-230). These autoantibodies bind to skeletal muscle and the immune complex formed by the autoantibody-antigen interaction is recognized by the initiating component of the classical complement pathway, the C1 complex. Binding of the C1 complex leads to a series of enzymatic cleavage steps culminating in the cleavage of C5 into C5a and C5b and deposition of MAC onto the sarcolemma, a characteristic finding in IMNM muscle biopsies.

This uncontrolled and inappropriate activation of the classical complement cascade in muscle tissue is thought to lead to the characteristic histopathological findings and ultimately clinical weakness in patients with IMNM.

In some embodiments, the present disclosure provides methods of treating IMNM that include administering zilucoplan. Zilucoplan may be used according to such methods to inhibit terminal complement pathway activation and MAC deposition associated with IMNM. Zilucoplan treatment may attenuate cell injury, reduce muscle cell derived creatine kinase in plasma, and/or attenuate or reverse clinical manifestations of IMNM.

Methods of the present disclosure for treating IMNM may include treating IMNM subtypes. IMNM subtypes may include one or more of Anti-SRP subtype, Anti-HMGCR subtype, and antibody negative subtype. One or more indication-related symptoms may be reduced or eliminated in treated subjects. Symptoms may include one or more of muscle weakness, chronic muscle inflammation, muscle atrophy and fatty replacement, elevated serum CK, dysphagia, neck weakness, myalgia, muscle fiber necrosis, and interstitial lung disease. Elevated serum CK may include serum creatine kinase levels greater than 1000 International Units/Liter (IU/L). Inflammatory myopathies may be diagnosed through serological testing, magnetic resonance imaging (MRI), and/or tissue biopsy.

Serological testing may include biomarker analysis. As used herein, the term "biomarker" refers to any agent or group of agents which may be detected and/or evaluated in a subject or a sample from a subject to yield information about the state of disease in the subject. Biomarkers for inflammatory myopathies may include hematology, chemistry, and/or coagulation analytes. In some embodiments, biomarkers include, but are not limited to, alanine aminotransferase (ALT), albumin, alkaline phosphatase (ALP), amylase, aspartate aminotransferase (AST), blood urea nitrogen (BUN), calcium, chloride, creatinine, gamma-glutamyl transferase (GGT), glucose, lactate dehydrogenase (LDH), lipase, potassium, sodium, total bilirubin, total protein, hematocrit, hemoglobin, mean corpuscular hemoglobin (MCH), mean corpuscular hemoglobin concentration (MCHC), mean corpuscular volume (MCV), platelet count, red blood cell (RBC) count, white blood cell (WBC) count and differential [basophils (% and absolute), eosinophils (% and absolute), lymphocytes (% and absolute), monocytes (% and absolute), and neutrophils (% and absolute)], aldolase, C-reactive protein (CRP), and creatine kinase (CK). Serological testing may include assessment of coagulation. Coagulation assessment may include assessment of prothrombin time (PT), partial thromboplastin time (PTT), activated partial thromboplastin time (aPTT), or ratios thereof [e.g., International normalized ratio (INR)]. Biomarkers may include complement proteins, such as C5 protein. In some embodiments, biomarkers include therapeutic agents (e.g., zilucoplan) or their metabolites being used for treatment, which may be detected in subjects or subject samples. In some embodiments, biomarkers include autoantibodies.

Autoantibody biomarkers may include autoantibodies binding to SRP, HMGCR, four-and-a-half LEVI domain 1 (FHL1), or survival of motor neuron (SMN). Autoantibody detection may be carried out according to any of the methods described or any of the antibodies analyzed in Albrecht, I, et al. 2015. J Clin Invest. 125(12) 4612-24; Amlani, A. et al., 2017. Rheumatology. 57: 199-200; Barranco, C. 2015. Nature Reviews Rheumatology. 12(1):2; or Satoh, M. et al., 2011. Arthritis and Rheumatism. 63(7): 1972-8, the contents of each of which are herein incorporated by reference in their entirety.

Methods of treating neuromuscular inflammatory indications (e.g., IMNM) may include administering complement inhibitor compounds (e.g., complement inhibitor compounds, e.g., zilucoplan) or compositions disclosed herein in combination with other therapeutic agents and/or therapeutic regimen. Therapeutic agents and/or regimen may include one or more of rituximab, steroids, immunosuppressive therapies (ISTs), and intravenous immunoglobulin therapies. Subjects may be treated with stable doses of corticosteroids, immunosuppressants, and/or IVIg.

Improvement in primary endpoints and/or secondary endpoints may be observed after neuromuscular inflammatory indication (e.g., IMNM) treatment with complement inhibitors. Primary endpoints may include reduced CK levels. CK levels may be reduced after complement inhibitor treatment of from about 1 day to about 10 days, from about 1 week to about 10 weeks, from about 8 weeks to about 24 weeks, or after shorter or longer periods of any of the foregoing. In some embodiments, CK levels may be reduced after 8 weeks of treatment. Secondary endpoints may include one or more of Triple Timed Up and Go (3TUG) test, Proximal Manual Muscle Testing (MMT), Physician Global Activity Visual Analogue Scale (VAS), Patient Global Activity VAS, Health Assessment Questionnaire (HAQ), Myositis Disease Activity Assessment Tool (MDAAT) Score, ACR/EULAR Response Criteria, and Functional Assessment of Chronic Illness Therapy (FACIT)-Fatigue scale.

MMT may be used to assess changes in muscle strength and assessment of clinical weakness. In some embodiments, MMT may be carried out according to methods described by Naqvi and Sherman, 2019 (Naqvi U, Sherman Al. Muscle Strength Grading. [Updated 2019 Jul. 1]. In: StatPearls [Internet]. Treasure Island (FL): StatPearls Publishing; 2019 January). Such MMT assessments may include grading patient strength on a scale of 0 to 5 according to the following criteria: (0) no muscle activation; (1) trace muscle activation, such as a twitch, without achieving full range of motion; (2) muscle activation with gravity eliminated, achieving full range of motion; (3) muscle activation against gravity, full range of motion; (4) muscle activation against some resistance, full range of motion; and (5) muscle activation against examiner's full resistance, full range of motion. MMT assessments yielding scores less than or equal to grade 4 may be used to categorize a subject as having clinical weakness.

Complement inhibitors used to treat neuroinflammatory indications (e.g., IMNM) may include zilucoplan. Zilucoplan may be administered at a dose of from about 0.1 mg/kg to about 0.3 mg/kg. Zilucoplan may be administered daily. Zilucoplan may be administered by subcutaneous injection. The subcutaneous injection may include the use of an auto injection device. Auto injection (synonymous with "self-injection") devices may include BD ULTRASAFE PLUS™ auto administration devices (BD, Franklin Lakes, NJ). Auto injection devices may include needles of any gauge (e.g., from about 20-gauge to about 34-gauge). In some embodiments, auto injection devices include needles with from about 29-gauge to about 31-gauge.

Screening

Subjects treated with zilucoplan may be screened prior to zilucoplan administration. As used herein, the term "screen" refers to a review or evaluation carried out for the purpose of selection or filtration. Subjects may be screened to select individuals in need of treatment. In some embodiments, subjects are screened to select individuals most likely to respond favorably to treatment. In some embodiments, screening is carried out to exclude individuals with greater risks associated with treatment. Screening may include assessment of biomarkers (e.g., any of the biomarkers described herein). Such biomarkers may include CK.

CK is a compact enzyme of around 82 kDa that is found in both the cytosol and mitochondria of tissues where energy demands are high. In the cytosol, CK is composed of two polypeptide subunits of around 42 kDa, and two types of subunit are found: M (muscle type) and B (brain type). These subunits allow the formation of three tissue-specific isoenzymes: CK-MB (cardiac muscle), CK-MM (skeletal muscle), and CK—BB (brain). Typically, the ratio of subunits varies with muscle type: skeletal muscle: 98% MM and 2% MB and cardiac muscle: 70-80% MM and 20-30% MB, while brain has predominantly BB. In mitochondria there are two specific forms of mitochondrial CK (Mt-CK): a nonsarcomeric type called ubiquitous Mt-CK expressed in various tissues such as brain, smooth muscle, and sperm, and a sarcomeric Mt-CK expressed in cardiac and skeletal muscle.

Creatine kinase is assayed in blood tests as a marker of damage of CK-rich tissue such as in rhabdomyolysis (severe muscle breakdown), muscular dystrophy, autoimmune myositides, myocardial infarction (heart attack), and acute kidney injury. In some embodiments, subjects are screened for CK levels. In some embodiments, subjects with CK levels greater than 1000 International Units/Liter (IU/L) are selected from treatment.

Subjects receiving IMNM therapies prior to or during screening may be maintained on such therapies during the screening process or may be required to withhold one or more treatments before or during the screening process. In some embodiments, a period of time between prior IMNM therapy and a screening assessment is required. The period of time may be required to obtain reliable results from a particular screening assessment.

Screening may include selecting subjects based on age. In some embodiments, screening may be carried out to select subjects with ages between 18 and 75 years old.

Screening may include selecting subjects previously diagnosed with IMNM. The IMNM diagnosis may be made according to criteria set forth by the 224$^{th}$ European Neuromuscular Center (ENMC) International Workshop or American College of Rheumatology/European League Against Rheumatism (ACR/EULAR).

Screening may include assessment of biomarker levels (e.g., levels of any of the biomarkers described herein). In some embodiments, biomarkers include anti-HMGCR or anti-SRP antibody levels. Screening may include review of subject prior and current treatments. In some embodiments, subjects are screened based on recent changes in treatments. In some embodiments, subjects are screened for corticosteroid and/or immunosuppressive treatment history. Screening may be used to confirm no change in corticosteroid dose or immunosuppressive therapy prior to screening. Screening may exclude subjects from treatment where subject corticosteroid treatment dose or immunosuppressive therapy regimen changes within the 30 days prior to screening.

Subjects may be screened for pregnancy status. In some embodiments, pregnant subjects may be excluded from treatment. Pregnancy status screening may be carried out by serum pregnancy test. In some embodiments, pregnancy screening may include urine pregnancy testing.

Zilucoplan Treatment

Zilucoplan inhibits C5a formation in a dose-dependent manner upon activation of the classical pathway and inhibits C5b formation (as measured by C5b-9 or MAC deposition on a complement activating surface) upon activation of the classical and alternative complement pathways. (U.S. Pat. No. 9,937,222).

In some embodiments, methods of the present disclosure include methods of treating IMNM by zilucoplan administration to a subject. Zilucoplan administration may be subcutaneous (SC) administration. Zilucoplan may be administered at a dose of from about 0.01 mg/kg (mg zilucoplan/kg subject body weight) to about 1.0 mg/kg, from about 0.02 mg/kg to about 2.0 mg/kg, from about 0.05 mg/kg to about 3.0 mg/kg, from about 0.10 mg/kg to about 4.0 mg/kg, from about 0.15 mg/kg to about 4.5 mg/kg, from about 0.20 mg/kg to about 5.0 mg/kg, from about 0.30 mg/kg to about 7.5 mg/kg, from about 0.40 mg/kg to about 10 mg/kg, from about 0.50 mg/kg to about 12.5 mg/kg, from about 0.1 mg/kg to about 0.6 mg/kg, from about 1.0 mg/kg to about 15 mg/kg, from about 2.0 mg/kg to about 20 mg/kg, from about 5.0 mg/kg to about 25 mg/kg, from about 10 mg/kg to about 45 mg/kg, from about 20 mg/kg to about 55 mg/kg, from about 30 mg/kg to about 65 mg/kg, from about 40 mg/kg to about 75 mg/kg, from about 50 mg/kg to about 150 mg/kg, from about 100 mg/kg to about 250 mg/kg, from about 200 mg/kg to about 350 mg/kg, from about 300 mg/kg to about 450 mg/kg, from about 400 mg/kg to about 550 mg/kg, or from about 500 mg/kg to about 1000 mg/kg.

In some embodiments, zilucoplan may be administered at a dose of from about 0.10 mg/kg to about 0.42 mg/kg.

Methods of the present disclosure may include administering zilucoplan at a daily dose of from about 0.1 mg/kg to about 0.3 mg/kg. In some embodiments, zilucoplan is administered at a daily dose of 0.3 mg/kg. CK levels may be reduced as a result of administration.

Zilucoplan administration may be by self-administration. Zilucoplan administration may include the use of self-administration devices. Self-administration devices may include prefilled syringes.

Zilucoplan may be provided as part of a pharmaceutical composition. Zilucoplan pharmaceutical compositions may include aqueous solutions. Zilucoplan pharmaceutical compositions may include phosphate-buffered saline (PBS). Zilucoplan pharmaceutical compositions may be preservative-free. Zilucoplan may be present in solutions at a concentration of from about 0.01 mg/mL to about 1 mg/mL, from about 0.05 mg/mL to about 2 mg/mL, from about 1 mg/mL to about 5 mg/mL, from about 2 mg/mL to about 10 mg/mL, from about 4 mg/mL to about 16 mg/mL, from about 5 mg/mL to about 20 mg/mL, from about 8 mg/mL to about 24 mg/mL, from about 10 mg/mL to about 30 mg/mL, from about 12 mg/mL to about 32 mg/mL, from about 14 mg/mL to about 34 mg/mL, from about 16 mg/mL to about 36 mg/mL, from about 18 mg/mL to about 38 mg/mL, from about 20 mg/mL to about 40 mg/mL, from about 22 mg/mL to about 42 mg/mL, from about 24 mg/mL to about 44 mg/mL, from about 26 mg/mL to about 46 mg/mL, from about 28 mg/mL to about 48 mg/mL, from about 30 mg/mL to about 50 mg/mL, from about 35 mg/mL to about 55 mg/mL, from about 40 mg/mL to about 60 mg/mL, from about 45 mg/mL to about 75 mg/mL, from about 50 mg/mL to about 100 mg/mL, from about 60 mg/mL to about 200 mg/mL, from about 70 mg/mL to about 300 mg/mL, from about 80 mg/mL to about 400 mg/mL, from about 90 mg/mL to about 500 mg/mL, or from about 100 mg/mL to about 1000 mg/mL.

In some embodiments, self-administration devices include zilucoplan pharmaceutical compositions. Self-administration devices may include zilucoplan pharmaceutical composition volumes of from about 0.010 mL to about 0.500 mL, from about 0.050 mL to about 0.600 mL, from about 0.100 mL to about 0.700 mL, from about 0.150 mL to about 0.810 mL, from about 0.200 mL to about 0.900 mL, from about 0.250 mL to about 1.00 mL, from about 0.300 mL to about 3.00 mL, from about 0.350 mL to about 3.50 mL, from about 0.400 mL to about 4.00 mL, from about 0.450 mL to about 4.50 mL, from about 0.500 mL to about 5.00 mL, from about 0.550 mL to about 10.0 mL, from about 0.600 mL to about 25.0 mL, from about 0.650 mL to about 50.0 mL, from about 0.700 mL to about 60.0 mL, from about 0.750 mL to about 75.0 mL, from about 0.800 mL to about 80.0 mL, from about 0.850 mL to about 85.0 mL, from about 0.900 mL to about 90.0 mL, from about 0.950 mL to about 95.0 mL, from about 1.00 mL to about 100 mL, from about 2.00 mL to about 200 mL, from about 5.00 mL to about 500 mL, from about 10.0 mL to about 750 mL, from about 25.0 mL to about 800 mL, from about 50.0 mL to about 900 mL, or from about 100 mL to about 1000 mL.

Zilucoplan treatment may be continuous or in one or more doses. In some embodiments, treatment is in doses that occur hourly, daily, bi-daily, weekly, bi-weekly, monthly, or combinations thereof. Zilucoplan treatment may include daily administration. Subject zilucoplan plasma levels may reach maximum concentration ($C_{max}$) on a first day of treatment. Serum hemolysis may be inhibited by zilucoplan treatment. In some embodiments, at least 90% hemolysis inhibition may be achieved in subject serum with zilucoplan treatment.

Zilucoplan treatment for IMNM may be carried out with a variety of subjects from different demographic backgrounds and stages of disease. In some embodiments, subjects with a stage of IMNM that occurs prior to reaching a critical or crisis stage are treated with zilucoplan. Such treatment may be carried out to treat subjects prior to developing IMNM or early in the disease process to provide benefits of proactive or preventative treatment.

In some embodiments, the present invention provides zilucoplan for use in a method of treating IMNM comprising administering 0.1 to 0.3 mg/kg zilucoplan subcutaneously or intravenously to a subject. In some embodiments, the present invention provides zilucoplan for use in a method of treating IMNM comprising administering 0.1 mg/kg or 0.3 mg/kg zilucoplan subcutaneously or intravenously to the subject. In some embodiments, the present invention provides zilucoplan for use in a method of treating IMNM comprising administering 0.1 mg/kg or 0.3 mg/kg zilucoplan subcutaneously to the subject. In some embodiments, the present invention provides zilucoplan for use in a method of treating IMNM comprising administering 0.3 mg/kg zilucoplan subcutaneously to the subject. In some embodiments, the subject is anti-HMGCR autoantibody-positive. In some embodiments, the subject is anti-HMGCR autoantibody-positive. In some embodiments, the subject is anti-SRP autoantibody-positive.

Evaluation

Subjects receiving zilucoplan treatment for IMNM may be evaluated for efficacy during or after treatment. As used herein, the term "treated subject" refers to an individual that has received at least one treatment. Zilucoplan treated subject evaluation may include evaluation of one or more metrics of efficacy. In some embodiments, evaluations may require subject treatments to be withheld for a period prior to evaluation. Some evaluations may require subjects to maintain consistent treatments before, during, and/or after evaluations. Withheld or maintained treatments may be zilucoplan treatments. In some embodiments, withheld or maintained treatments include other treatments for IMNM.

Evaluations may be carried out to assess primary efficacy endpoints. As used herein, the term "primary endpoint" refers to a result that answers the most important inquiry addressed by a particular study. The term "secondary endpoint," refers to a result that answers other relevant inquiries subordinate to a main inquiry. A primary efficacy endpoint is a result that addresses whether or not a treatment is effective, while a secondary efficacy endpoint addresses one or more peripheral inquiries (e.g., quality of life impact, side effect severity, etc.).

Evaluations may be carried out to assess subject IMNM characteristics. As used herein, the term "IMNM characteristic" refers to a physical or mental trait or set of traits associated with the presence of or severity of IMNM in a subject. IMNM characteristics may include scores obtained using different disease evaluation methods. IMNM characteristic may include, but are not limited to, one or more of CK levels, Triple Timed Up and Go (3TUG) test, Proximal Manual Muscle Testing (MMT), Physician Global Activity Visual Analogue Scale (VAS), Patient Global Activity VAS, Health Assessment Questionnaire (HAQ), Myositis Disease Activity Assessment Tool (MDAAT) Score, ACR/EULAR Response Criteria, and FACIT-Fatigue scale. In some embodiments, subjects may be monitored for IMNM characteristics over time. Such monitoring may be carried out over the course of IMNM disease. Monitoring may be carried out over the course of disease treatment. In some embodiments, subject evaluation or monitoring is carried out to assess changes in IMNM characteristics during or after subject treatment with zilucoplan.

In some embodiments, zilucoplan treated subjects are evaluated or monitored for CK levels. In a healthy adult, the serum CK level varies with a number of factors (gender, race and activity), but normal range includes 22 to 198 International Units/Liter IU/L. In some embodiments, the elevated serum CK comprises serum creatine kinase levels greater than 1000 International Units/Liter.

In some embodiments, change in CK levels may be a primary efficacy endpoint. Treated subject CK levels may be reduced. The CK levels may be reduced at or before 8 weeks of zilucoplan treatment. Treated subject CK levels may be monitored over the course of zilucoplan treatment.

In some embodiments, zilucoplan treated subject evaluations may include one or more of Triple Timed Up and Go (3TUG) test, Proximal Manual Muscle Testing (MMT), Physician Global Activity Visual Analogue Scale (VAS), Patient Global Activity VAS, Health Assessment Questionnaire (HAQ), Myositis Disease Activity Assessment Tool (MDAAT) Score, ACR/EULAR Response Criteria, and Functional Assessment of Chronic Illness Therapy (FACIT)-Fatigue scale. Such scores may be evaluated as secondary efficacy endpoints.

Monitoring for CK levels, Triple Timed Up and Go (3TUG) test, Proximal Manual Muscle Testing (MMT), Physician Global Activity Visual Analogue Scale (VAS), Patient Global Activity VAS, Health Assessment Questionnaire (HAQ), Myositis Disease Activity Assessment Tool (MDAAT) Score, ACR/EULAR Response Criteria, and Functional Assessment of Chronic Illness Therapy (FACIT)-Fatigue may be used to identify changes from baseline score. As used herein, the term "baseline score" refers to a score obtained before initial treatment. Baseline scores may be scores obtained between a switch from one treatment to another. The switch may be from a placebo to an active pharmaceutical compound. In some embodiments, zilucoplan treatment may be evaluated for reduction in CK levels. The reduction may occur at or before 8 weeks of zilucoplan treatment.

In some embodiments, zilucoplan treatment leads to reduced subject symptom expression. The reduced subject symptom expression may exceed reduced subject symptom expression associated with eculizumab administration.

Evaluation Methods

In some embodiments, the present disclosure provides methods of evaluating treatments for IMNM. Such methods may include screening evaluation candidates for at least one evaluation participation criteria. As used herein, the term "evaluation candidate" refers to any individual being considered for participation in an evaluation (e.g., a clinical study). "Evaluation participation criteria" refers to a metric or factor used to select individuals to include in an evaluation. Evaluation candidates selected for participation in an evaluation are referred to herein as "evaluation participants." In some embodiments, methods of evaluating treatments for IMNM may include screening an evaluation candidate for at least one evaluation participation criteria; selecting an evaluation participant; administering the treatment for IMNM to the evaluation participant; and assessing at least one efficacy endpoint.

In some embodiments, evaluation participation criteria include IMNM diagnosis. Diagnosis of IMNM may be made according to criteria set forth by the 224$^{th}$ European Neuromuscular Center (ENMC) International Workshop or American College of Rheumatology/European League Against Rheumatism (ACR/EULAR) criteria.

In some embodiments, evaluation participation criteria include evaluation candidate age. In some embodiments, evaluation candidates must be between 18 and 75 years old.

Evaluation participation criteria may include specific candidate biomarker levels (e.g., any of the biomarkers described herein). In some embodiments, such biomarkers include anti-HMGCR or anti-SRP antibody levels.

Evaluation participation criteria may include candidate prior and current alternative IMNM treatment status. In some embodiments, evaluation participants are selected based consistency of current or former alternative IMNM treatments. In some embodiments, candidates with no recent change in corticosteroid dose or immunosuppressive therapy are selected. Candidates with corticosteroid treatment dose or immunosuppressive therapy regimen changes within the past 30 days may be excluded from evaluation participation.

Evaluation participation criteria may include pregnancy status. In some embodiments, pregnant subjects may be excluded from evaluation participation. Pregnancy status screening may be carried out by serum pregnancy test. In some embodiments, pregnancy screening may include urine pregnancy testing.

Methods of evaluating treatments for IMNM may include administering treatments for IMNM to evaluate participants over an evaluation period. As used herein, the term "evaluation period" refers to a time frame over which a particular study takes place. Treatments may be administered over evaluation periods of from about one day to about 24 weeks. Some evaluation periods are about 8 weeks or longer. Evaluation participants may continue to receive standard of care IMNM therapies over evaluation periods. Such therapies may include, but are not limited to administration of rituximab, a steroid, an immunosuppressive therapy (IST), and an intravenous immunoglobulin treatment.

Efficacy endpoints may include certain scores or changes in scores associated with assessments for individuals with IMNM. In some embodiments, efficacy endpoint comprises a change in baseline CK levels. In some embodiments, efficacy endpoint comprises a change in baseline score for one or more of CK levels, Triple Timed Up and Go (3TUG) test, Proximal Manual Muscle Testing (MMT), Physician Global Activity Visual Analogue Scale (VAS), Patient Global Activity VAS, Health Assessment Questionnaire (HAQ), Myositis Disease Activity Assessment Tool (MDAAT) Score, ACR/EULAR Response Criteria, and FACIT-Fatigue In some embodiments, assessing efficacy endpoints includes a set of assessments. The set of assessments may be carried out in a particular order.

Assessments for efficacy endpoints may be carried out on one or more occasions after administering treatments for IMNM. Such assessments may be carried out at specific times and/or dates or may be carried out on a recurring basis (e.g., hourly, daily, weekly, monthly, or combinations thereof). In some embodiments, assessments are carried out 1 week, 2 weeks, 4 weeks, and/or 8 weeks after starting administration of treatments for IMNM.

In some embodiments, methods of the present disclosure include evaluating treatment with complement inhibitor compounds and compositions described herein (e.g., zilucoplan) by evaluating subject muscle strength and/or function in response to treatment. Such evaluations may be carried out to assess complement inhibitor (e.g., zilucoplan) suitability for treating IMNM or efficacy in treating IMNM. Evaluations may be carried out in animal models. In some embodiments, such animal models may include mouse models. IMNM mouse models may include those described by Bergua, C., et al. in Ann. Rheum. Dis. 2019, 78(1), p131-139, the contents of which are herein incorporated by reference in their entirety. In Bergua, mice exhibited muscle deficiency, as seen in IMNM, upon passive transfer of autoimmune anti-SRP or anti-HMGCR antibodies from human IMNM patients or upon immunization with SRP or HMGCR. The observed muscle deficiency was complement-dependent as C3 −/− (complement-deficient) mice were resistant to these effects unless supplemented with human complement. In some embodiments, treatment with complement inhibitors of the present disclosure (e.g., zilucoplan) may be evaluated for efficacy in preventing or reversing muscle deficiency associated with that observed in IMNM mouse models (e.g., where muscle deficiency is caused by autoantibody passive transfer or immunization-induced expression). Such evaluations may include evaluating mouse muscle strength with or without complement inhibitor (e.g., zilucoplan) treatment according to methods described in Bergua, C., et al. in Ann. Rheum. Dis. 2019, 78(1). Such evaluations may be useful for designing, implementing, and/or determining dosage for complement inhibitor (e.g., zilucoplan) treatments for IMNM in humans.

In some embodiments, the present disclosure provides methods of treating IMNM in subjects by administering zilucoplan to such subjects and evaluating subject muscle strength by measuring contraction of subject muscles. As used herein, the term "subject" refers to any organism to which a compound or method in accordance with the disclosure may be administered or applied, e.g., for experimental, diagnostic, prophylactic, and/or therapeutic purposes. Typical subjects include animals (e.g., mammals such as mice, rats, rabbits, porcine subjects, non-human primates, and humans). Zilucoplan may be administered by subcutaneous injection. Zilucoplan may be administered daily. Zilucoplan may be administered at a dose of from about 0.01 to about 20 mg/kg of subject body weight. In some embodiments, zilucoplan may be administered at about 10 mg/kg of subject body weight. With some methods, subject samples (e.g., subject serum samples) may be obtained and analyzed for complement activity. Subject samples may be analyzed for C5a level and/or C5b-9 level. Such analysis may be carried out by standard enzyme-linked immunosorbent assay (ELISA). Some subjects may have or express anti-HMGCR antibodies. Such antibodies may be detected in subject samples (e.g., serum samples).

In some embodiments, the present disclosure provides methods of treating reduced muscle strength in subjects by administering zilucoplan and confirming increased subject muscle strength, wherein the increased subject muscle strength is confirmed by measuring contraction of a subject muscle. Zilucoplan may be administered by subcutaneous injection. Zilucoplan may be administered daily. Zilucoplan may be administered at a dose of from about 0.01 to about 20 mg/kg of subject body weight. In some embodiments, zilucoplan may be administered at about 10 mg/kg of subject body weight. With some methods, subject samples (e.g., subject serum samples) may be obtained and analyzed for complement activity. Subject samples may be analyzed for C5a level and/or C5b-9 level. Some subjects may have or express an anti-HMGCR antibody. Treated subjects may have or may be suspected of having IMNM.

Measuring contraction of subject muscles may be carried out after stimulating contraction of such muscles. Stimulating contraction may be carried out by electrostimulation. In some embodiments, a nerve associated subject muscles is stimulated to induce muscle contraction. Subject muscles evaluated may include gastrocnemius muscles. Measuring contraction of gastrocnemius muscles may be carried out after electrostimulation of an associated sciatic nerve.

In some embodiments, the present disclosure provides compositions for use according to methods of treating IMNM and/or reduced muscle strength presented herein, wherein such compositions include zilucoplan. Such compositions may be administered by subcutaneous injection. Zilucoplan compositions may be administered daily. Zilucoplan compositions may be administered at a dose sufficient to provide about 10 mg zilucoplan per kg of subject body weight.

In some embodiments, methods of the present disclosure include evaluating treatment with complement inhibitor compounds and compositions described herein (e.g., zilucoplan) by evaluating subject muscle tissues for evidence of muscle deficiency. Such subjects may be human subjects with IMNM. Subjects may be animal model subjects (e.g., mice from IMNM mouse models). Muscle tissues may be evaluated with or without prior complement inhibitor treatment (e.g., to assess such treatment). Evaluations may include reverse transcription PCR, immunostaining (e.g., for neonatal myosin heavy chain), or muscle fiber measurement (e.g., see Allenbach, Y., et al. Neurology 2018, 90(6), e507-e517; and Arouche-Delaperche, L. in Ann. Neurol. 2017, 81(4), 538-548 for related methods, the contents of each of which are herein incorporated by reference in their entirety).

In some embodiments, methods of the present disclosure include evaluating autoantibody serum levels. Such methods may include addressable laser bead immunoassay (ALBIA) as described in Benveniste, O. et al., Arthritis Rheum. 2011, 63(7), 1961-1971, the contents of which are herein incorporated by reference in their entirety. ALBIA may be used to determine anti-SRP and/or anti-HMGCR autoantibody levels in serum, which may be used, for example, to correlate with other factors (e.g., serum creatine kinase levels and/or muscle strength).

Assays

In some embodiments, methods of the present disclosure include assays for evaluating zilucoplan and compositions thereof. Such assays may include assays for evaluating zilucoplan suitability and/or efficacy in treating IMNM. Assays may include IMNM mouse models. IMNM mouse models may include those described by Bergua, C., et al. in Ann. Rheum. Dis. 2019, 78(1), p131-139, the contents of which are herein incorporated by reference in their entirety. In Bergua, mice exhibited muscle deficiency, as seen in IMNM, upon passive transfer of autoimmune anti-SRP or anti-HMGCR antibodies from human IMNM patients or upon immunization with SRP or HMGCR. The observed muscle deficiency was complement-dependent as C3 −/− (complement-deficient) mice were resistant to these effects unless supplemented with human complement. In some embodiments, zilucoplan may be evaluated for preventing or reversing muscle deficiency in IMNM mouse models (e.g., where muscle deficiency is caused by anti-SRP or anti-HMGCR autoantibody passive transfer of immunization-induced expression). Such evaluations may include evaluating mouse muscle strength with or without zilucoplan treatment. In some embodiments, the mouse muscle strength may be assessed by evaluating mouse muscle response to electrostimulation and/or by evaluating mouse grip strength (e.g., as described in Bergua, C., et al. in Ann. Rheum. Dis. 2019, 78(1)).

In some embodiments, methods of the present disclosure include assays for evaluating muscle tissues for muscle deficiency. Such muscle tissues may be from IMNM mouse models. Muscle tissues may be evaluated with or without prior complement inhibitor treatment (e.g., to assess such treatment). Assays for evaluating muscle tissue for muscle deficiency may include reverse transcription PCR, immunostaining (e.g., for neonatal myosin heavy chain), or muscle fiber measurement (e.g., see Allenbach, Y., et al. Neurology 2018, 90(6), e507-e517; and Arouche-Delaperche, L. in Ann. Neurol. 2017, 81(4), 538-548 for related methods, the contents of each of which are herein incorporated by reference in their entirety).

In some embodiments, methods of the present disclosure include evaluating autoantibody serum levels. Such methods may include addressable laser bead immunoassay (ALBIA) as described in Benveniste, O. et al., Arthritis Rheum. 2011, 63(7), 1961-1971, the contents of which are herein incorporated by reference in their entirety. ALBIA may be used to determine anti-SRP and/or anti-HMGCR autoantibody levels in serum, which may be used, for example, to correlate with other factors (e.g., serum creatine kinase levels and/or muscle strength).

In some embodiments, methods of the present disclosure include methods of evaluating zilucoplan treatment of IMNM by preparing mouse subjects to exhibit muscle weakness that mimics muscle weakness associated with human IMNM (e.g., as described in Bergua, C., et al. in Ann. Rheum. Dis. 2019, 78(1), p131-139). Such mouse subjects may be prepared by administration of anti-SRP and/or anti-HMGCR human IgG antibodies such as those found with human IMNM. C5-deficient mouse subjects may be used and supplemented with human C5 by administration of human serum. Human serum may be depleted of IgG prior to administration to limit the identity of human IgG in the mice to the anti-HMGCR antibodies. Mice prepared to exhibit muscle weakness mimicking that of human IMNM may be administered zilucoplan to evaluate the effect of zilucoplan treatment on the mice and ability to improve muscle strength.

Improvement in mouse muscle weakness may be evaluated by directly measuring mouse muscle (e.g., gastrocnemius muscle) contraction upon electrostimulation of the sciatic nerve. In some embodiments, improvements in exhibited muscle weakness may be evaluated by examining mouse subject muscle tissue sections for muscle fiber necrosis (e.g., as described in Allenbach, Y., et al. Neurology 2018, 90(6), e507-e517; and Arouche-Delaperche, L. in Ann. Neurol. 2017, 81(4), 538-548).

Administration of anti-HMGCR antibodies and human serum in mouse subjects may be by intraperitoneal injection. The IgG antibodies may be administered every other day for 8 days. The human serum may be administered daily. The zilucoplan may be administered to the mouse subjects by subcutaneous injection. The zilucoplan may be administered daily. The zilucoplan may be administered at a dose of about 10 mg/kg.

Formulations

In some embodiments, compounds or compositions, e.g., pharmaceutical compositions, of the present disclosure are formulated in aqueous solutions. In some cases, aqueous solutions further include one or more salt and/or one or more buffering agent. Salts may include sodium chloride which may be included at concentrations of from about 0.05 mM to about 50 mM, from about 1 mM to about 100 mM, from about 20 mM to about 200 mM, or from about 50 mM to about 500 mM. Further solutions may include at least 500 mM sodium chloride. In some cases, aqueous solutions include sodium phosphate. Sodium phosphate may be included in aqueous solutions at a concentration of from about 0.005 mM to about 5 mM, from about 0.01 mM to about 10 mM, from about 0.1 mM to about 50 mM, from about 1 mM to about 100 mM, from about 5 mM to about 150 mM, or from about 10 mM to about 250 mM. In some cases, at least 250 mM sodium phosphate concentrations are used.

Compositions of the present disclosure may include C5 inhibitors at a concentration of from about 0.001 mg/mL to about 0.2 mg/mL, from about 0.01 mg/mL to about 2 mg/mL, from about 0.1 mg/mL to about 10 mg/mL, from about 0.5 mg/mL to about 5 mg/mL, from about 1 mg/mL to about 20 mg/mL, from about 15 mg/mL to about 40 mg/mL, from about 25 mg/mL to about 75 mg/mL, from about 50 mg/mL to about 200 mg/mL, or from about 100 mg/mL to about 400 mg/mL. In some cases, compositions include C5 inhibitors at a concentration of at least 400 mg/mL.

Compositions of the present disclosure may include C5 inhibitors at a concentration of approximately, about or exactly any of the following values: 0.001 mg/mL, 0.2 mg/mL, 0.01 mg/mL, 2 mg/mL, 0.1 mg/mL, 10 mg/mL, 0.5 mg/mL, 5 mg/mL, 1 mg/mL, 20 mg/mL, 15 mg/mL, 40 mg/mL, 25 mg/mL, 75 mg/mL, 50 mg/mL, 200 mg/mL, 100 mg/mL, or 400 mg/mL. In some cases, compositions include C5 inhibitors at a concentration of at least 40 mg/mL.

In some embodiments, compositions of the present disclosure include aqueous compositions including at least water and a C5 inhibitor (e.g., a cyclic C5 inhibitor polypeptide). Aqueous C5 inhibitor compositions may further include one or more salt and/or one or more buffering agent. In some cases, aqueous compositions include water, a cyclic C5 inhibitor polypeptide, a salt, and a buffering agent.

Aqueous C5 inhibitor formulations may have pH levels of from about 2.0 to about 3.0, from about 2.5 to about 3.5, from about 3.0 to about 4.0, from about 3.5 to about 4.5, from about 4.0 to about 5.0, from about 4.5 to about 5.5, from about 5.0 to about 6.0, from about 5.5 to about 6.5, from about 6.0 to about 7.0, from about 6.5 to about 7.5, from about 7.0 to about 8.0, from about 7.5 to about 8.5, from about 8.0 to about 9.0, from about 8.5 to about 9.5, or from about 9.0 to about 10.0.

In some cases, compounds and compositions of the present disclosure are prepared according to good manufacturing practice (GMP) and/or current GMP (cGMP). Guidelines used for implementing GMP and/or cGMP may be obtained from one or more of the US Food and Drug Administration (FDA), the World Health Organization (WHO), and the International Conference on Harmonization (ICH).

Dosage and Administration

For treatment of human subjects, C5 inhibitors (e.g., zilucoplan and/or active metabolites or variants thereof) may be formulated as pharmaceutical compositions. Depending on the subject to be treated, the mode of administration, and the type of treatment desired (e.g., prevention, prophylaxis, or therapy) C5 inhibitors may be formulated in ways consonant with these parameters. A summary of such techniques is found in Remington: The Science and Practice of Pharmacy, 21st Edition, Lippincott Williams & Wilkins, (2005); and Encyclopedia of Pharmaceutical Technology, eds. J. Swarbrick and J. C. Boylan, 1988-1999, Marcel Dekker, New York, each of which is incorporated herein by reference.

C5 inhibitors (e.g., zilucoplan and/or active metabolites or variants thereof) may be provided in a therapeutically effective amount. In some cases, a therapeutically effective amount of a C5 inhibitor may be achieved by administration of a dose of from about 0.1 mg to about 1 mg, from about 0.5 mg to about 5 mg, from about 1 mg to about 20 mg, from about 5 mg to about 50 mg, from about 10 mg to about 100 mg, from about 20 mg to about 200 mg, or at least 200 mg of one or more C5 inhibitors.

In some embodiments, subjects may be administered a therapeutic amount of a C5 inhibitor (e.g., zilucoplan and/or active metabolites or variants thereof) based on the weight of such subjects. In some cases, C5 inhibitors are administered at a dose of from about 0.001 mg/kg to about 1.0 mg/kg, from about 0.01 mg/kg to about 2.0 mg/kg, from about 0.05 mg/kg to about 5.0 mg/kg, from about 0.03 mg/kg to about 3.0 mg/kg, from about 0.01 mg/kg to about 10 mg/kg, from about 0.1 mg/kg to about 2.0 mg/kg, from about 0.2 mg/kg to about 3.0 mg/kg, from about 0.4 mg/kg to about 4.0 mg/kg, from about 1.0 mg/kg to about 5.0 mg/kg, from about 2.0 mg/kg to about 4.0 mg/kg, from about 1.5 mg/kg to about 7.5 mg/kg, from about 5.0 mg/kg to about 15 mg/kg, from about 7.5 mg/kg to about 12.5 mg/kg, from about 10 mg/kg to about 20 mg/kg, from about 15 mg/kg to about 30 mg/kg, from about 20 mg/kg to about 40 mg/kg, from about 30 mg/kg to about 60 mg/kg, from about 40 mg/kg to about 80 mg/kg, from about 50 mg/kg to about 100 mg/kg, or at least 100 mg/kg. Such ranges may include ranges suitable for administration to human subjects. Dosage levels may be highly dependent on the nature of the condition; drug efficacy; the condition of the patient; the judgment of the practitioner; and the frequency and mode of administration. In some embodiments, zilucoplan and/or active metabolites or variants thereof may be administered at a dose of from about 0.01 mg/kg to about 10 mg/kg. In some cases, zilucoplan and/or active metabolites or variants thereof may be administered at a dose of from about 0.1 mg/kg to about 3 mg/kg.

In some cases, C5 inhibitors (e.g., zilucoplan and/or active metabolites or variants thereof) are provided at concentrations adjusted to achieve a desired level of the C5 inhibitor in a sample, biological system, or subject (e.g., plasma level in a subject). In some cases, desired concentrations of C5 inhibitors in a sample, biological system, or subject may include concentrations of from about 0.001 μM to about 0.01 from about 0.005 μM to about 0.05 μM, from about 0.02 μM to about 0.2 μM, from about 0.03 μM to about 0.3 from about 0.05 μM to about 0.5 from about 0.01 μM to about 2.0 from about 0.1 μM to about 50 μM, from about 0.1 μM to about 10 μM, from about 0.1 μM to about 5 μM, from about 0.2 μM to about 20 μM, from about 5 μM to about 100 μM, or from about 15 μM to about 200 μM. In some cases, desired concentrations of C5 inhibitors in subject plasma may be from about 0.1 μg/mL to about 1000 μg/mL. The desired concentration of C5 inhibitors in subject plasma may be from about 0.01 μg/mL to about 2 μg/mL, from about 0.02 μg/mL to about 4 μg/mL, from about 0.05 μg/mL to about 5 μg/mL, from about 0.1 μg/mL to about 1.0 μg/mL, from about 0.2 μg/mL to about 2.0 μg/mL, from about 0.5 μg/mL to about 5 μg/mL, from about 1 μg/mL to about 5 μg/mL, from about 2 μg/mL to about 10 μg/mL, from about 3 μg/mL to about 9 μg/mL, from about 5 μg/mL to about 20 μg/mL, from about 10 μg/mL to about 40 μg/mL, from about 30 μg/mL to about 60 μg/mL, from about 40 μg/mL to about 80 μg/mL, from about 50 μg/mL to about 100 μg/mL, from about 75 μg/mL to about 150 μg/mL, or at least 150 μg/mL. In other embodiments, C5 inhibitors are administered at a dose sufficient to achieve a maximum serum concentration ($C_{max}$) of at least 0.1 μg/mL, at least 0.5 μg/mL, at least 1 μg/mL, at least 5 μg/mL, at least 10 μg/mL, at least 50 μg/mL, at least 100 μg/mL, or at least 1000 μg/mL.

In some embodiments, C5 inhibitors (e.g., zilucoplan and/or active metabolites or variants thereof) are administered daily at a dose sufficient to deliver from about 0.1 mg/day to about 60 mg/day per kg weight of a subject. In some cases, the $C_{max}$ achieved with each dose is from about 0.1 μg/mL to about 1000 μg/mL. In such cases, the area under the curve (AUC) between doses may be from about 200 μg*hr/mL to about 10,000 μg*hr/mL.

According to some methods of the present disclosure, C5 inhibitors (e.g., zilucoplan and/or active metabolites or variants thereof) are provided at concentrations needed to achieve a desired effect. In some cases, compounds and compositions of the disclosure are provided at an amount necessary to reduce a given reaction or process by half. The concentration needed to achieve such a reduction is referred to herein as the half maximal inhibitory concentration, or "$IC_{50}$." Alternatively, compounds and compositions of the disclosure may be provided at an amount necessary to increase a given reaction, activity or process by half. The concentration needed for such an increase is referred to herein as the half maximal effective concentration or "$EC_{50}$."

C5 inhibitors (e.g., zilucoplan and/or active metabolites or variants thereof) may be present in amounts totaling 0.1-95% by weight of the total weight of the composition. In some cases, C5 inhibitors are provided by intravenous (IV) administration. In some cases, C5 inhibitors are provided by subcutaneous (SC) administration.

SC administration of C5 inhibitors (e.g., zilucoplan and/or active metabolites or variants thereof) may, in some cases, provide advantages over IV administration. SC administration may allow patients to provide self-treatment. Such treatment may be advantageous in that patients could provide treatment to themselves in their own home, avoiding the need to travel to a provider or medical facility. Further, SC treatment may allow patients to avoid long-term complications associated with IV administration, such as infections, loss of venous access, local thrombosis, and hematomas. In some embodiments, SC treatment may increase patient compliance, patient satisfaction, quality of life, reduce treatment costs and/or drug requirements.

In some cases, daily SC administration provides steady-state C5 inhibitor concentrations that are reached within 1-3 doses, 2-3 doses, 3-5 doses, or 5-10 doses. In some cases, daily SC doses of from about 0.1 mg/kg to about 0.3 mg/kg may achieve sustained C5 inhibitor levels greater than or equal to 2.5 μg/mL and/or inhibition of complement activity of greater than 90%.

C5 inhibitors (e.g., zilucoplan and/or active metabolites or variants thereof) may exhibit slow absorption kinetics (time to maximum observed concentration of greater than 4-8 hours) and high bioavailability (from about 75% to about 100%) after SC administration.

In some embodiments, dosage and/or administration are altered to modulate the half-life ($t_{1/2}$) of C5 inhibitor levels in a subject or in subject fluids (e.g., plasma). In some cases, $t_{1/2}$ is at least 1 hour, at least 2 hrs, at least 4 hrs, at least 6 hrs, at least 8 hrs, at least 10 hrs, at least 12 hrs, at least 16 hrs, at least 20 hrs, at least 24 hrs, at least 36 hrs, at least 48 hrs, at least 60 hrs, at least 72 hrs, at least 96 hrs, at least 5 days, at least 6 days, at least 7 days, at least 8 days, at least 9 days, at least 10 days, at least 11 days, at least 12 days, at least 2 weeks, at least 3 weeks, at least 4 weeks, at least 5 weeks, at least 6 weeks, at least 7 weeks, at least 8 weeks, at least 9 weeks, at least 10 weeks, at least 11 weeks, at least 12 weeks, or at least 16 weeks.

In some embodiments, C5 inhibitors (e.g., zilucoplan and/or active metabolites or variants thereof) may exhibit long terminal $t_{1/2}$. Extended terminal $t_{1/2}$ may be due to extensive target binding and/or additional plasma protein binding. In some cases, C5 inhibitors exhibit $t_{1/2}$ values greater than 24 hours in both plasma and whole blood. In some cases, C5 inhibitors do not lose functional activity after incubation in human whole blood at 37° C. for 16 hours.

In some embodiments, dosage and/or administration are altered to modulate the steady state volume of distribution of C5 inhibitors. In some cases, the steady state volume of distribution of C5 inhibitors is from about 0.1 mL/kg to about 1 mL/kg, from about 0.5 mL/kg to about 5 mL/kg, from about 1 mL/kg to about 10 mL/kg, from about 5 mL/kg to about 20 mL/kg, from about 15 mL/kg to about 30 mL/kg, from about 10 mL/kg to about 200 mL/kg, from about 20 mL/kg to about 60 mL/kg, from about 30 mL/kg to about 70 mL/kg, from about 50 mL/kg to about 200 mL/kg, from about 100 mL/kg to about 500 mL/kg, or at least 500 mL/kg. In some cases, the dosage and/or administration of C5 inhibitors is adjusted to ensure that the steady state volume of distribution is equal to at least 50% of total blood volume. In some embodiments, C5 inhibitor distribution may be restricted to the plasma compartment.

In some embodiments, C5 inhibitors (e.g., zilucoplan and/or active metabolites or variants thereof) exhibit a total clearance rate of from about 0.001 mL/hr/kg to about 0.01 mL/hr/kg, from about 0.005 mL/hr/kg to about 0.05 mL/hr/kg, from about 0.01 mL/hr/kg to about 0.1 mL/hr/kg, from about 0.05 mL/hr/kg to about 0.5 mL/hr/kg, from about 0.1 mL/hr/kg to about 1 mL/hr/kg, from about 0.5 mL/hr/kg to about 5 mL/hr/kg, from about 0.04 mL/hr/kg to about 4 mL/hr/kg, from about 1 mL/hr/kg to about 10 mL/hr/kg, from about 5 mL/hr/kg to about 20 mL/hr/kg, from about 15 mL/hr/kg to about 30 mL/hr/kg, or at least 30 mL/hr/kg.

Time periods for which maximum concentration of C5 inhibitors in subjects (e.g., in subject serum) are maintained ($T_{max}$ values) may be adjusted by altering dosage and/or administration (e.g., subcutaneous administration). In some cases, C5 inhibitors have $T_{max}$ values of from about 1 min to about 10 min, from about 5 min to about 20 min, from about 15 min to about 45 min, from about 30 min to about 60 min, from about 45 min to about 90 min, from about 1 hour to about 48 hrs, from about 2 hrs to about 10 hrs, from about 5 hrs to about 20 hrs, from about 10 hrs to about 60 hrs, from about 1 day to about 4 days, from about 2 days to about 10 days, or at least 10 days.

In some embodiments, C5 inhibitors (e.g., zilucoplan and/or active metabolites or variants thereof) may be administered without off-target effects. In some cases, C5 inhibitors do not inhibit hERG (human ether-a-go-go related gene), even with concentrations less than or equal to 300 μM. SC injection of C5 inhibitors with dose levels up to 10 mg/kg may be well tolerated and not result in any adverse effects of the cardiovascular system (e.g., elevated risk of prolonged ventricular repolarization) and/or respiratory system.

C5 inhibitor doses may be determined using the no observed adverse effect level (NOAEL) observed in another species. Such species may include, but are not limited to monkeys, rats, rabbits, and mice. In some cases, human equivalent doses (HEDs) may be determined by allometric scaling from NOAELs observed in other species. In some cases, HEDs result in therapeutic margins of from about 2 fold to about 5 fold, from about 4 fold to about 12 fold, from about 5 fold to about 15 fold, from about 10 fold to about 30 fold, or at least 30 fold. In some cases, therapeutic margins are determined by using exposure in primates and estimated human $C_{max}$ levels in humans.

In some embodiments, C5 inhibitors of the present disclosure allow for a rapid washout period in cases of infection where prolonged inhibition of the complement system is detrimental.

C5 inhibitor administration according to the present disclosure may be modified to reduce potential clinical risks to subjects. Infection with *Neisseria meningitidis* is a known risk of C5 inhibitors, including eculizumab. In some cases, risk of infection with *Neisseria meningitides* is minimized by instituting one or more prophylactic steps. Such steps may include the exclusion of subjects who may already be colonized by these bacteria. In some cases, prophylactic steps may include coadministration with one or more antibiotics. In some cases, ciprofloxacin may be co-administered. In some cases, ciprofloxacin may be co-administered orally at a dose of from about 100 mg to about 1000 mg (e.g., 500 mg).

In some embodiments, C5 inhibitors (e.g., zilucoplan and/or active metabolites or variants thereof) are administered at a frequency of every hour, every 2 hrs, every 4 hrs, every 6 hrs, every 12 hrs, every 18 hrs, every 24 hrs, every 36 hrs, every 72 hrs, every 84 hrs, every 96 hrs, every 5 days, every 7 days, every 10 days, every 14 days, every week, every two weeks, every 3 weeks, every 4 weeks, every month, every 2 months, every 3 months, every 4 months, every 5 months, every 6 months, every year, or at least every year. In some cases, C5 inhibitors are administered once daily or administered as two, three, or more sub-doses at appropriate intervals throughout the day.

In some embodiments, C5 inhibitors are administered in multiple daily doses. In some cases, C5 inhibitors are administered daily for 7 days. In some cases, C5 inhibitors are administered daily for 7 to 100 days. In some cases, C5 inhibitors are administered daily for at least 100 days. In some cases, C5 inhibitors are administered daily for an indefinite period.

Methods of the present disclosure may include administering a C5 inhibitor (e.g., zilucoplan and/or active metabolites or variants thereof) at a daily dose of from about 0.1 mg/kg to about 0.3 mg/kg. In some embodiments, a C5 inhibitor (e.g., zilucoplan and/or active metabolites or variants thereof) is administered at a daily dose of 0.3 mg/kg. Subject CK levels may be reduced as a result of administration.

C5 inhibitors delivered intravenously may be delivered by infusion over a period of time, such as over a 5 minute, 10 minute, 15 minute, 20 minute, or 25 minute period. The administration may be repeated, for example, on a regular basis, such as hourly, daily, weekly, biweekly (i.e., every two weeks), for one month, two months, three months, four months, or more than four months. After an initial treatment regimen, treatments may be administered on a less frequent basis. For example, after biweekly administration for three months, administration may be repeated once per month, for six months or a year or longer. C5 inhibitor administration may reduce, lower, increase or alter binding or any physiologically deleterious process (e.g., in a cell, tissue, blood, urine or other compartment of a patient) by at least 10%, at least 15%, at least 20%, at least 25%, at least 30%, at least 40%, at least 50%, at least 60%, at least 70%, at least 80% or at least 90% or more.

Before administration of a full dose of C5 inhibitor and/or C5 inhibitor composition, patients can be administered a smaller dose, such as 5% of a full dose, and monitored for adverse effects, such as an allergic reaction or infusion reaction, or for elevated lipid levels or blood pressure. In another example, patients can be monitored for unwanted immunostimulatory effects, such as increased cytokine (e.g., TNF-alpha, IL-1, IL-6, or IL-10) levels.

Genetic predisposition plays a role in the development of some diseases or disorders. Therefore, patients in need of C5 inhibitors may be identified by family history analysis, or, for example, screening for one or more genetic markers or variants. Healthcare providers (e.g., doctors or nurses) or family members may analyze family history information before prescribing or administering therapeutic compositions of the present disclosure.

III. Kits and Devices

In some embodiments, the present disclosure provides kits and devices. Such kits and devices may include any of the compounds or compositions described herein. In a non-limiting example, zilucoplan may be included.

Devices of the present disclosure may include administration devices. As used herein, the term "administration device" refers to any tool for providing a substance to a recipient. Administration devices may include self-administration devices. As used herein, the term "self-administration device" refers to any tool used for providing a substance to a recipient, wherein use of the tool is carried out wholly or in part by the recipient. Self-administration devices may include self-injection devices. "Self-injection devices" are self-administration devices that enable individuals to subcutaneously administer substances to their own body. Self-injection devices may include prefilled syringes. As used herein, the term "prefilled syringe" refers to a syringe that has been loaded with a substance or cargo prior to access or use by an operator of the syringe. For example, prefilled syringes (also referred to herein as "pre-loaded syringes") may be filled with a therapeutic composition prior to packaging in a kit; prior to syringe shipment to a distributor, administrator, or operator; or prior to access by a subject using the syringe for self-administration. Due to cyclic peptide stability, cyclic peptide inhibitors (e.g., zilucoplan) are especially well suited for manufacture, storage, and distribution in pre-loaded syringes. Further, pre-loaded syringes are especially well suited for self-administration (i.e., administration by a subject, without the aid of a medical professional). Self-administration represents a convenient way for subjects to obtain treatments without relying on medical professionals who may be located at a distance or are otherwise difficult to access. This makes self-administration options well suited for treatments requiring frequent injections (e.g., daily injections).

Prefilled syringes may be of any material (e.g., glass, plastic, or metal). In some embodiments, prefilled syringes are glass syringes. Prefilled syringes may include maximum fill volumes (meaning the largest amount of liquid that can be contained) of at least 0.1 ml, at least 0.2 ml, at least 0.3 ml, at least 0.4 ml, at least 0.5 ml, at least 0.75 ml, at least 1.0 ml, at least 1.5 ml, at least 2.0 ml, at least 5.0 ml, at least 10 ml, or more than 10 ml. Fill volumes may be from about 0.2 ml to about 2 ml. Syringes may include needles. The needles may be of any gauge (e.g., from about 20-gauge to about 34-gauge). In some embodiments, syringes include needles with a gauge of from about 29-gauge to about 31-gauge. The needles may be assembled with syringes or attached prior to syringe use. Self-injection devices may include BD ULTRASAFE PLUS™ self-administration devices (BD, Franklin Lakes, NJ).

Administration devices may include self-injection devices that include a syringe and needle and a predetermined volume of a zilucoplan composition. The zilucoplan composition may be a pharmaceutical composition. The composition may include a zilucoplan concentration of from about 1 mg/mL to about 200 mg/mL. In some embodiments, the zilucoplan concentration is about 40 mg/mL. Predetermined volumes may be predetermined based on subject body weight. In some embodiments, predetermined zilucoplan composition volumes are modified to facilitate zilucoplan administration to a subject at a dose of from about 0.1 mg/kg to about 0.6 mg/kg. Volumes may be modified to facilitate 0.3 mg/kg zilucoplan dosing. The self-injection device may include a BD ULTRASAFE PLUS™ self-administration device. In some embodiments, administration devices are prepared for storage at specific temperatures or temperature ranges. Some administration devices may be prepared for storage at room temperature. Some administration devices may be prepared for storage between from about 2° C. to about 8° C.

Pre-filled syringes may include ULTRASAFE PLUS™ passive needle guards (Becton Dickenson, Franklin Lakes, NJ). Other pre-filled syringes may include injection pens. Injection pens may be multi-dose pens. Some pre-filled syringes may include a needle. In some embodiments, the needle gauge is from about 20-gauge to about 34-gauge. The needle gauge may be from about 29-gauge to about 31-gauge.

In some embodiments, kits of the present disclosure include kits carrying out methods of treating IMNM described herein. Such kits may include one or more administration devices described herein and instructions for kit usage.

Kit components may be packaged in liquid (e.g., aqueous or organic) media or in dry (e.g., lyophilized) form. Kits may include containers that may include, but are not limited to vials, test tubes, flasks, bottles, syringes, or bags. Kit containers may be used to aliquot, store, preserve, insulate, and/or protect kit components. Kit components may be packaged together or separately. Some kits may include containers of sterile, pharmaceutically acceptable buffer and/or other diluent (e.g., phosphate buffered saline). In some embodiments, kits include containers of kit components in dry form with separate containers of solution for dissolving dried components. In some embodiments, kits include a syringe for administering one or more kit components.

When polypeptides are provided as a dried powder it is contemplated that between 10 micrograms and 1000 milligrams of polypeptide, or at least or at most those amounts are provided in kits.

Containers may include at least one vial, test tube, flask, bottle, syringe and/or other receptacle, into which polypeptide formulations may be placed, preferably, suitably allocated. Kits may also include containers for sterile, pharmaceutically acceptable buffer and/or another diluent.

Kits may include instructions for employing kit components as well the use of any other reagent not included in the kit. Instructions may include variations that can be implemented.

Kits may include one or more items for addressing syringe wounds. Such items may include, but are not limited to, alcohol wipes and wound dressings (e.g., cotton balls, mesh pads, bandages, tape, gauze, etc.). Kits may further include disposal containers for disposal of used kit components. Disposal containers may be designed for disposal of sharp objects, such as needles and syringes. Some kits may include instructions for sharp object disposal.

In some embodiments, kits of the present disclosure include zilucoplan in powdered form or in solution (e.g., as pharmaceutical compositions). Solutions may be aqueous solutions. Solutions may include PBS. Zilucoplan pharmaceutical compositions may include from about 4 mg/ml to about 200 mg/ml zilucoplan. In some embodiments, zilucoplan pharmaceutical compositions include about 40 mg/ml zilucoplan. Zilucoplan pharmaceutical compositions may include preservatives. In some embodiments, zilucoplan pharmaceutical compositions are preservative-free.

In some embodiments, kits are prepared for storage at specific temperatures or temperature ranges. Some kits may be prepared for storage at room temperature. Some kits may be prepared for storage between from about 2° C. to about 8° C.

IV. Definitions

Administered in combination: As used herein, the term "administered in combination" or "combined administration" means that a subject is simultaneously exposed to two or more agents administered at the same time or within an interval of time such that the subject is at some point in time simultaneously exposed to both and/or such that there may be an overlap in the effect of each agent on the patient. In some embodiments, at least one dose of one or more agents is administered within about 24 hours, 12 hours, 6 hours, 3 hours, 1 hour, 30 minutes, 15 minutes, 10 minutes, 5 minutes, or 1 minute of at least one dose of one or more other agents. In some embodiments, administration occurs in overlapping dosage regimens. As used herein, the term "dosage regimen" refers to a plurality of doses spaced apart in time. Such doses may occur at regular intervals or may include one or more hiatus in administration.

Bioavailability: As used herein, the term "bioavailability" refers to the systemic availability of a given amount of a compound (e.g., C5 inhibitor) administered to a subject. Bioavailability can be assessed by measuring the area under the curve (AUC) or the maximum serum or plasma concentration ($C_{max}$) of the unchanged form of a compound following administration of the compound to a subject. AUC is a determination of the area under the curve when plotting the serum or plasma concentration of a compound along the ordinate (Y-axis) against time along the abscissa (X-axis). Generally, the AUC for a particular compound can be calculated using methods known to those of ordinary skill in the art and/or as described in G. S. Banker, Modern Pharmaceutics, Drugs and the Pharmaceutical Sciences, v. 72, Marcel Dekker, New York, Inc., 1996, the contents of which are herein incorporated by reference in their entirety.

Biological system: As used herein, the term "biological system" refers to a cell, a group of cells, a tissue, an organ, a group of organs, an organelle, a biological fluid, a biological signaling pathway (e.g., a receptor-activated signaling pathway, a charge-activated signaling pathway, a metabolic pathway, a cellular signaling pathway, etc.), a group of proteins, a group of nucleic acids, or a group of molecules (including, but not limited to biomolecules) that carry out at least one biological function or biological task within cellular membranes, cellular compartments, cells, cell cultures, tissues, organs, organ systems, organisms, multicellular organisms, biological fluids, or any biological entities. In some embodiments, biological systems are cell signaling pathways that include intracellular and/or extracellular signaling biomolecules. In some embodiments, biological systems include proteolytic cascades (e.g., the complement cascade).

Buffering agent: As used herein, the term "buffering agent" refers to a compound used in a solution for the purposes of resisting changes in pH. Such compounds may include, but are not limited to acetic acid, adipic acid, sodium acetate, benzoic acid, citric acid, sodium benzoate, maleic acid, sodium phosphate, tartaric acid, lactic acid, potassium metaphosphate, glycine, sodium bicarbonate, potassium phosphate, sodium citrate, and sodium tartrate.

Clearance rate: As used herein, the term "clearance rate" refers to the velocity at which a particular compound is cleared from a biological system or fluid.

Compound: As used herein, the term "compound," refers to a distinct chemical entity. In some embodiments, a particular compound may exist in one or more isomeric or isotopic forms (including, but not limited to stereoisomers, geometric isomers and isotopes). In some embodiments, a compound is provided or utilized in only a single such form. In some embodiments, a compound is provided or utilized as a mixture of two or more such forms (including, but not limited to a racemic mixture of stereoisomers). Those of skill in the art will appreciate that some compounds exist in different forms, show different properties and/or activities (including, but not limited to biological activities). In such cases it is within the ordinary skill of those in the art to select or avoid particular forms of a compound for use in accordance with the present disclosure. For example, compounds that contain asymmetrically substituted carbon atoms can be isolated in optically active or racemic forms.

Cyclic or Cyclized: As used herein, the term "cyclic" refers to the presence of a continuous loop. The continuous loop may be formed by a chemical bond between different regions of a compound (also referred to herein as a "cyclic bond.") Cyclic molecules need not be circular, only joined to form an unbroken chain of subunits. Cyclic polypeptides may include a "cyclic loop," formed when two amino acids are connected by a bridging moiety. The cyclic loop comprises the amino acids along the polypeptide present between the bridged amino acids. Cyclic loops may include 2, 3, 4, 5, 6, 7, 8, 9, 10 or more amino acids.

Downstream event: As used herein, the term "downstream" or "downstream event," refers to any event occurring after and/or as a result of another event. In some cases, downstream events are events occurring after and as a result of C5 cleavage and/or complement activation. Such events may include, but are not limited to, generation of C5 cleavage products, activation of MAC, hemolysis, and hemolysis-related disease (e.g., PNH).

Equilibrium dissociation constant: As used herein, the term "equilibrium dissociation constant" or "$K_D$" refers to a value representing the tendency of two or more agents (e.g., two proteins) to reversibly separate. In some cases, $K_D$ indicates a concentration of a primary agent at which half of the total levels of a secondary agent are associated with the primary agent.

Half-life: As used herein, the term "half-life" or "$t_{1/2}$" refers to the time it takes for a given process or compound concentration to reach half of a final value. The "terminal half-life" or "terminal $t_{1/2}$" refers to the time needed for the plasma concentration of a factor to be reduced by half after the concentration of the factor has reached a pseudo-equilibrium.

Identity: As used herein, the term "identity," when referring to polypeptides or nucleic acids, refers to a comparative relationship between sequences. The term is used to describe the degree of sequence relatedness between polymeric sequences and may include the percentage of matching monomeric components with gap alignments (if any) addressed by a particular mathematical model or computer program (i.e., "algorithms"). Identity of related polypeptides can be readily calculated by known methods. Such methods include, but are not limited to, those described previously by others (Lesk, A. M., ed., Computational Molecular Biology, Oxford University Press, New York, 1988; Smith, D. W., ed., Biocomputing: Informatics and Genome Projects, Academic Press, New York, 1993; Griffin, A. M. et al., ed., Computer Analysis of Sequence Data, Part 1, Humana Press, New Jersey, 1994; von Heinje, G., Sequence Analysis in Molecular Biology, Academic Press, 1987; Gribskov, M. et al., ed., Sequence Analysis Primer, M. Stockton Press, New York, 1991; and Carillo et al., Applied Math, SIAM J, 1988, 48, 1073).

Inhibitor: As used herein, the term "inhibitor" refers to any agent that blocks or causes a reduction in the occurrence of a specific event; cellular signal; chemical pathway; enzymatic reaction; cellular process; interaction between two or more entities; biological event; disease; disorder; or condition.

Initial loading dose: As used herein, an "initial loading dose" refers to a first dose of a therapeutic agent that may differ from one or more subsequent doses. Initial loading doses may be used to achieve an initial concentration of a therapeutic agent or level of activity before subsequent doses are administered.

Intravenous: As used herein, the term "intravenous" refers to the area within a blood vessel. Intravenous administration typically refers to delivery of a compound into the blood through injection in a blood vessel (e.g., vein).

In vitro: As used herein, the term "in vitro" refers to events that occur in an artificial environment (e.g., in a test tube or reaction vessel, in cell culture, in a Petri dish, etc.), rather than within an organism (e.g., animal, plant, or microbe).

In vivo: As used herein, the term "in vivo" refers to events that occur within an organism (e.g., animal, plant, or microbe or cell or tissue thereof).

Lactam bridge: As used herein, the term "lactam bridge" refers to an amide bond that forms a bridge between chemical groups in a molecule. In some cases, lactam bridges are formed between amino acids in a polypeptide.

Linker: The term "linker" as used herein refers to a group of atoms (e.g., 10-1,000 atoms), molecule(s), or other compounds used to join two or more entities. Linkers may join such entities through covalent or non-covalent (e.g., ionic or hydrophobic) interactions. Linkers may include chains of two or more polyethylene glycol (PEG) units. In some cases, linkers may be cleavable.

Minute volume: As used herein, the term "minute volume" refers to the volume of air inhaled or exhaled from a subject's lungs per minute.

Non-proteinogenic: As used herein, the term "non-proteinogenic" refers to any non-natural proteins, such as those with non-natural components, such as non-natural amino acids.

Patient: As used herein, "patient" refers to a subject who may seek or be in need of treatment, requires treatment, is receiving treatment, will receive treatment, or a subject who is under the care of a trained professional for a particular disease or condition.

Pharmaceutical composition: As used herein, the term "pharmaceutical composition" refers to a composition with at least one active ingredient (e.g., a C5 inhibitor) in a form and amount that permits the active ingredient to be therapeutically effective.

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: The phrase "pharmaceutically acceptable excipient," as used herein, refers to any ingredient other than active agents (e.g., active agent zilucoplan and/or active metabolites thereof or variants thereof) present in a pharmaceutical composition and having the properties of being substantially nontoxic and non-inflammatory in a patient. In some embodiments, a pharmaceutically acceptable excipient is a vehicle capable of suspending or dissolving the active agent. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Plasma compartment: As used herein, the term "plasma compartment" refers to intravascular space occupied by blood plasma.

Salt: As used herein, the term "salt" refers to a compound made up of a cation with a bound anion. Such compounds may include sodium chloride (NaCl) or other classes of salts including, but not limited to acetates, chlorides, carbonates, cyanides, nitrites, nitrates, sulfates, and phosphates. The term "salt" may also be used to refer to salt forms of polypeptides described herein (e.g., zilucoplan salt). Such polypeptide salts may include zilucoplan sodium salt.

Sample: As used herein, the term "sample" refers to an aliquot or portion taken from a source and/or provided for analysis or processing. In some embodiments, a sample is from a biological source such as a tissue, cell or component part (e.g., a body fluid, including but not limited to blood, mucus, lymphatic fluid, synovial fluid, cerebrospinal fluid, saliva, amniotic fluid, amniotic cord blood, urine, vaginal fluid and semen). In some embodiments, a sample may be or include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, or organs. In some embodiments, a sample is or includes a medium, such as a nutrient broth or gel, which may contain cellular components, such as proteins. In some embodiments, a "primary" sample is an aliquot of the source. In some embodiments, a primary sample is subjected to one or more processing (e.g., separation, purification, etc.) steps to prepare a sample for analysis or other use.

Subcutaneous: As used herein, the term "subcutaneous" refers to the space underneath the skin. Subcutaneous administration is delivery of a compound beneath the skin.

Subject: As used herein, the term "subject" refers to any organism to which a compound or method in accordance with the disclosure may be administered or applied, e.g., for experimental, diagnostic, prophylactic, and/or therapeutic purposes. Typical subjects include animals (e.g., mammals such as mice, rats, rabbits, porcine subjects, non-human primates, and humans).

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Therapeutically effective amount: As used herein, the term "therapeutically effective amount" means an amount of an agent to be delivered (e.g., C5 inhibitor) that is sufficient, when administered to a subject suffering from or susceptible to a disease, disorder, and/or condition, to treat, improve symptoms of, diagnose, prevent, and/or delay the onset of the disease, disorder, and/or condition.

Tidal volume: As used herein, the term "tidal volume" refers to the normal lung volume of air displaced between breaths (in the absence of any extra effort).

$T_{max}$: As used herein, the term "$T_{max}$" refers to the time period for which maximum concentration of a compound in a subject or fluid is maintained.

Treating: As used herein, the term "treating" refers to partially or completely alleviating, ameliorating, improving, relieving, delaying onset of, inhibiting progression of, reducing severity of, and/or reducing incidence of one or more symptoms or features of a particular disease, disorder, and/or condition. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Treatment dose: As used herein, "treatment dose" refers to one or more doses of a therapeutic agent administered in the course of addressing or alleviating a therapeutic indication. Treatment doses may be adjusted to maintain a desired concentration or level of activity of a therapeutic agent in a body fluid or biological system.

Volume of distribution: As used herein, the term "volume of distribution" or "$V_{dist}$" refers to a fluid volume required to contain the total amount of a compound in the body at the same concentration as in the blood or plasma. The volume of distribution may reflect the extent to which a compound is present in the extravascular tissue. A large volume of distribution reflects the tendency of a compound to bind to tissue components compared with plasma protein components. In a clinical setting, $V_{dist}$ can be used to determine a loading dose of a compound to achieve a steady state concentration of that compound.

Equivalents and Scope

While various embodiments of the disclosure have been particularly shown and described, it will be understood by those skilled in the art that various changes in form and details may be made therein without departing from the spirit and scope of the disclosure as defined by the appended claims.

Those skilled in the art will recognize or be able to ascertain using no more than routine experimentation, many equivalents to the specific embodiments in accordance with the disclosure described herein. The scope of the present disclosure is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise.

In addition, it is to be understood that any particular embodiment of the present disclosure that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the disclosure (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

EXAMPLES

Example 1. Preparation of Zilucoplan Aqueous Solution

Polypeptides were synthesized using standard solid-phase Fmoc/tBu methods. The synthesis was performed on a Liberty automated microwave peptide synthesizer (CEM, Matthews NC) using standard protocols with Rink amide resin, although other automated synthesizers without microwave capability may also be used. All amino acids were obtained from commercial sources. The coupling reagent used was 2-(6-chloro-1-H-benzotriazole-1yl)-1,1,3,3,-tetramethylaminium hexafluorophosphate (HCTU) and the base was diisopropylethylamine (DIEA). Polypeptides were cleaved from resin with 95% TFA, 2.5% TIS and 2.5% water for 3 hours and isolated by precipitation with ether. The crude polypeptides were purified on a reverse phase preparative HPLC using a C18 column, with an acetonitrile/water 0.1% TFA gradient from 20%-50% over 30 min. Fractions containing pure polypeptides were collected and lyophilized and all polypeptides were analyzed by LC-MS.

Zilucoplan (SEQ ID NO: 1; CAS Number: 1841136-73-9), as described in International Publication Numbers WO2017105939 and WO2018106859, was prepared as a cyclic peptide containing 15 amino acids (4 of which are non-natural amino acids), an acetylated N-terminus, and a C-terminal carboxylic acid. The C-terminal lysine of the core peptide has a modified side chain, forming a N-ε-(PEG24-γ-glutamic acid-N-α-hexadecanoyl) lysine reside. This modified side chain includes a polyethylene glycol spacer (PEG24) attached to an L-γ glutamic acid residue that is derivatized with a palmitoyl group. The cyclization of zilucoplan is via a lactam bridge between the side-chains of L-Lys1 and L-Asp6. All of the amino acids in zilucoplan are L-amino acids. Zilucoplan has a molecular weight of 3562.23 g/mol and a chemical formula of $C_{172}H_{278}N_{24}O_{55}$.

Like eculizumab, zilucoplan blocks the proteolytic cleavage of C5 into C5a and C5b. Unlike eculizumab, zilucoplan can also bind to C5b and block C6 binding which prevents the subsequent assembly of the MAC.

Zilucoplan was prepared as an aqueous solution for injection containing 40 mg/mL of zilucoplan in a formulation of 50 mM sodium phosphate and 75.7 mM sodium chloride at a pH of 7.0. The resulting composition was used to prepare a medicinal product, in accordance with current Good Manufacturing Practices (cGMPs), the medicinal product including a 1 ml glass syringe with a 29 gauge, ½ inch staked needle placed within a needle safety self-administration device (ULTRASAFE PLUS™, Becton Dickenson, Franklin Lakes, NJ).

Example 2. Zilucoplan Administration and Storage

Zilucoplan is administered by subcutaneous (SC) or intravenous (IV) injection and the dose administered (dose volume) is adjusted based on subject weight on a mg/kg basis. This is achieved using a set of fixed doses aligned to a set of weight brackets. In total, human dosing supports a broad weight range of 43 to 109 kg. Subjects who present with a higher body weight (>109 kg) are accommodated on a case-by-case basis, in consultation with a medical monitor.

Zilucoplan is stored at 2° C. to 8° C. [36° F. to 46° F.]. Once dispensed to subjects, zilucoplan is stored at controlled room temperature (20° C. to 25° C. [68° F. to 77° F.]) for up to 30 days and is protected from sources of excessive temperature fluctuations such as high heat or exposure to light. Storage of zilucoplan outside of room temperature is preferably avoided. Zilucoplan may be stored for up to 30 days under these conditions.

Example 3. Zilucoplan Treatment of Immune-Mediated Necrotizing Myopathy (IMNM)

Overview

A study is carried out to confirm the potential of treating IMNM with zilucoplan. The study is a randomized, double-blind, placebo-controlled, multi-center study, followed by an open label, long-term extension. Study participants are selected from a broad patient population of individuals diagnosed with IMNM. Study participants are HMG-CoA reductase (HMGCR) and/or signal recognition particle (SRP) autoantibody positive and have clinical weakness (≤grade 4 out of 5) based on manual muscle testing in at least one proximal limb muscle group. Approximately 24 patients are randomized in a 1:1 ratio to receive daily subcutaneous (SC) doses of 0.3 mg/kg zilucoplan or placebo for eight weeks. Randomization is stratified based on antibody status (anti-HMGCR-positive versus anti-SRP positive).

Change in creatine kinase (CK) levels from baseline to week 8 is the primary endpoint. Secondary endpoints include baseline changes observed with Triple Timed Up and Go (3TUG) Test (ambulatory subjects only), Proximal Manual Muscle Testing (MMT), Physician Global Activity [Visual Analog Scale (VAS)], Patient Global Activity (VAS), Myositis Disease Activity Assessment Tool (MDAAT) Score, American College of Rheumatology/European League Against Rheumatism (ACR/EULAR) Response Criteria, FACIT-Fatigue Scale, and Health Assessment Questionnaire (HAQ). Some subjects are also assessed for mechanistic biomarkers and/or analyzed using pharmacogenomic analysis. Following completion of the trial, patients are given the option to enter in an open-label long-term extension study with zilucoplan.

Zilucoplan and the matching placebo are supplied as sterile, preservative-free, aqueous solutions prefilled into 1 mL glass syringes (BD ULTRASAFE PLUS™ self-administration device, BD, Franklin Lakes, NJ) with 29 gauge, ½ inch, staked needles placed within self-administration devices. Fill volumes are adjusted based on subject weight range to achieve correct mg/kg dose range. Subjects are instructed to self-administer SC doses daily. During the Treatment Period, subjects return to the clinic at Week 1, Week 2, Week 4, and Week 8 to evaluate safety, tolerability, and efficacy. Plasma concentrations of C5, zilucoplan, and any zilucoplan metabolites are assessed from samples taken during clinic visits. Samples are also tested for complement activation by hemolysis assay (using sheep red blood cells or other).

After the 8 week study period, subjects meeting certain selection criteria are given the option of receiving zilucoplan during an extension study. Visits during the first 8 weeks of the extension study are identical to the main portion of the study for all subjects.

Example 4. Zilucoplan Inhibits Autoantibody-Induced Complement Activity at the Neuromuscular Junction (NMJ)

Co-cultures of human myotubes and neuroblastoma cells were prepared and cultured with human sera as an in vitro NMJ model. Cells were cultured with or without 10 zilucoplan and anti-acetyl choline receptor (AChR) 637 antibodies of either IgG1 or IgG4 format. The IgG1 antibodies are known to facilitate complement-mediated C5b-9 deposition, while the IgG4 antibodies do not. Subsequent deposition of C5b-9 was observed by immunofluorescence using an anti-C5b-9 antibody (aE11, AbCam, Cambridge, UK). C5b-9 deposition was observed in cells cultured with anti-AChR 637 IgG1, but without zilucoplan. C5b-9 deposition was absent in cells cultured under the same conditions, but with 10 μM zilucoplan.

Example 5. Zilucoplan Permeability

Zilucoplan in-vitro permeability was assessed using a basement membrane model. In the model, diffusion of zilucoplan across an extracellular matrix (ECM) gel membrane (prepared as described in Arends, F. et al. 2016. IntechOpen, DOI: 10.5772/62519) was assessed and compared with diffusion of eculizumab. In the model, compounds were introduced to an upper reservoir, which was separated from a lower reservoir by the ECM gel membrane. The ECM gel membrane was prepared to include matrix components mimicking those found in the basal lamina of neuromuscular junctions. Permeability of the compounds across the membrane was assessed by detection in the lower reservoir. Greater than 20% of the zilucoplan introduced to the upper reservoir had diffused to the lower reservoir after 12 hours and more than 60% by 24 hours. In contrast, less than 20% of eculizumab diffused to the lower reservoir after 24 hours. The results demonstrate superior permeability of zilucoplan across the basement membrane as compared with eculizumab (about four times higher), suggesting preferential tissue penetration.

Enhanced permeability of zilucoplan was confirmed by quantitative whole body analysis (QWBA). For this study, zilucoplan C-terminal lysine was radiolabeled with $^{14}C$ and administered to rats. Animals were imaged to determine concentration of radiolabeled zilucoplan over time (24 hours) in multiple organs and tissues. Area under the concentration curve (AUC) for each organ or tissue analyzed was expressed as a percentage of plasma AUC to yield a biodistribution value, presented in Table 2 below. Inferred eculizumab biodistribution values, based on monoclonal antibody biodistribution studies published in Shah, D. K., et al. 2013. mAbs. 5:297-305, are provided for comparison.

TABLE 2

| Biodistribution comparison | | |
|---|---|---|
| Organ/tissue | Eculizumab biodistribution % | Zilucoplan biodistribution % |
| Lung | 14.9 | 37.5 |
| Heart | 10.2 | 22.9 |
| Muscle | 3.97 | 7.0 |
| Small Intestine | 5.22 | 10.9 |
| Large Intestine | 5.03 | 21.7 |
| Spleen | 12.8 | 15.5 |
| Liver | 12.1 | 27.1 |
| Bone | 7.27 | 15.3 |
| Stomach | 4.98 | 8.5 |
| Lymph nodes | 8.46 | 12.8 |
| Fat | 4.78 | 16.2 |
| Brain | 0.35 | 0.9 |
| Pancreas | 6.4 | 15.8 |
| Testes | 5.88 | 15.5 |
| Thymus | 6.62 | 7.8 |

These results support the use of zilucoplan to inhibit C5 activity in tissues where C5 inhibitor tissue-penetration is needed and wherein eculizumab tissue-penetration is insufficient.

Example 6. Zilucoplan Drug-Drug Interactions

Zilucoplan in vivo drug-drug interaction studies were carried out with potential comedications in non-human primates. The first investigated the effects of cyclosporine A on the pharmacokinetics of zilucoplan and vice versa. Cyclosporine A is a known inhibitor of organic anion transporting polypeptide (OATP) 1B1 and OATP1B3 and is a potential comedication in PNH. No effects on zilucoplan exposure were observed following cyclosporine A administration, and no effects on cyclosporin A exposure were observed following zilucoplan administration. These results support methods of treating complement-related indications (e.g., IMNM) in subjects by combined administration of zilucoplan and cyclosporin A.

The second in vivo drug-drug interaction study was performed with zilucoplan and an inhibitor of neonatal Fc receptor (FcRN) recycling, DX-2507, a functionally equivalent variant of DX-2504 with Cys to Ala mutations to improve manufacturing (described in Nixon, A. E. et al. 2015. Front Immunol. 6:176). By inhibiting FcRN, DX-2504 inhibits Fc-mediated recycling, thereby reducing the half-life of IgG antibodies. Administration of DX-2504 serves as a model for intravenous immunoglobulin (IVIg) treatment, which reduces the half-life of IgG antibodies by overwhelming the Fc recycling mechanism with large doses of immunoglobulin. Zilucoplan pharmacokinetics and pharmacodynamics did not change with concomitant dosing of anti-FcRN monoclonal antibody DX-2507 in Cynomolgus monkeys. In addition, no changes in zilucoplan levels were observed in a patient receiving concomitant therapeutic doses of IVIg. These results indicate no effects of FcRN inhibition on zilucoplan pharmacokinetics and support methods of treating complement-related indications (e.g., IMNM) in subjects by combined administration of zilucoplan and FcRN inhibitor (DX-2504, DX-2507, or IVIg).

Example 7. Zilucoplan Immune-Mediated Necrotizing Myopathy (IMNM) Treatment evaluation A multicenter, randomized, double-blind, placebo-controlled study is carried out to evaluate zilucoplan safety, tolerability, and efficacy in treating subjects with IMNM who are positive for anti-HMGCR (3-hydroxy-3-methylglutaryl-coenzyme A reductase) or anti-SRP (signal recognition particle). During the study of approximately 24 subjects, subjects are randomized in a 1:1 ratio to receive daily SC doses of 0.3 mg/kg zilucoplan, or matching placebo. Randomization is stratified based on screening antibody status (anti-HMGCR+versus anti-SRP+).

The Main Portion of the study includes a Screening Period of up to 4 weeks and an 8-week Treatment Period. During the Treatment Period, subjects return to the clinic at Week 1, Week 2, Week 4 and Week 8 to evaluate safety, tolerability, and efficacy. Additional assessments include biomarker testing, pharmacokinetics, pharmacodynamics, and optional pharmacogenomics. Safety assessments include physical examinations, vital signs, electrocardiogram (ECG), clinical laboratory tests, adverse event (AE) monitoring, and immunogenicity.

Zilucoplan and the matching placebo are supplied as sterile, preservative-free, aqueous solutions prefilled into 1 mL glass syringes with 29 gauge, ½-inch, staked needles placed within self-administration devices. Fill volumes are adjusted based on subject weight range to achieve correct mg/kg dose range. Subjects are instructed to self-administer SC doses daily.

Doses of zilucoplan are determined by target dose and weight, accomplished using fixed dose by weight brackets. These brackets are grouped by body weight category such that each subject received no less than the target minimum dose to avoid sub-therapeutic dosing. Table 3 summarizes the dose presentations for zilucoplan doses. Subjects with a higher body weight (>150 kg) are accommodated on a case-by-case basis. Matching placebo is provided in 1 presentation of 0.574 mL.

TABLE 3

| Zilucoplan dose presentations by weight brackets | | | |
|---|---|---|---|
| Minimum (Nominal) Target Dose (mg/kg) | Actual Dose (mg) | Weight Range (kg) | Dose Range (mg/kg) |
| 0.3 | 16.6 | ≥43 to <56 | 0.30 to 0.39 |
| 0.3 | 23.0 | ≥56 to <77 | 0.30 to 0.41 |
| 0.3 | 32.4 | ≥77 to 150 | 0.22 to 0.42 |

Screening

Screening is carried out to determine subject study eligibility. Screening includes CK level assessment. The patient population most appropriate for zilucoplan treatment is expected to have a CK level of >1000 U/L at screening. Other eligibility criteria assessed during screening include age between 18 and 75; clinical diagnosis of IMNM at time of screening; positive serology for anti-HMGCR or anti-SRP autoantibodies; clinical evidence of weakness (≤grade 4 out of 5) on manual muscle testing in at least one proximal limb muscle group; no change in corticosteroid dose for at least 30 days prior to baseline or anticipated to occur during the first 8-weeks treatment period; and no change in immunosuppressive therapy, including dose, for at least 30 days prior to baseline or anticipated to occur during the first 8-weeks Treatment Period. Female subjects of childbearing potential needed to have a negative serum pregnancy test at screening and a negative urine pregnancy test within 24 hours prior to the first dose of study drug; sexually active female subjects of childbearing potential (i.e., women who were not postmenopausal or who had not had a hysterectomy, bilateral oophorectomy, or bilateral tubal ligation) and all male subjects (who had not been surgically sterilized by vasectomy) agreed to use effective contraception during the study.

During screening, assessments are performed that included review of medical history and demographics, including collection of detailed history of IMNM diagnosis information, as well as local serology for anti-HMGCR or anti-SRP autoantibodies; efficacy assessment of triple timed-up-and-go (3TUG) (in ambulatory subjects only), proximal manual muscle testing (MMT), physician global visual analogue scale (VAS), patient global VAS, health assessment questionnaire (HAQ), myositis disease activity assessment tool (MDAAT) and functional assessment of chronic illness therapy (FACIT)-fatigue scale; height and weight measurement; assessment of vital signs [heart rate (HR), body temperature, and blood pressure in the sitting position]; 12-lead ECG; assessment of prior *Neisseria meningitidis* vaccination; collection of blood samples for laboratory testing [hematology, chemistry, creatine kinase (CK) and coagulation (if applicable)]; collection of urine samples for urinalysis; serum pregnancy testing for females of child-bearing potential; collection of blood sample for anti-drug antibody (ADA) testing and collection of blood samples for central testing of disease specific antibody testing (anti-HMGCR or anti-SRP autoantibodies).

Subjects meeting any of the following criteria are excluded from the study: (1) history of meningococcal disease; (2) current or recent systemic infection within 2 weeks prior to screening or infection requiring IV antibiotics within 4 weeks prior to screening; (3) pregnant, planning to become pregnant, or nursing female subjects; (4) recent surgery requiring general anesthesia within 2 weeks prior to screening or surgery expected to occur during the 8-week treatment period; (5) treatment with a complement inhibitor or an experimental drug within 30 days or 5 half-lives of the experimental drug (whichever is longer) prior to baseline; (6) statin use within 30 days prior to baseline or anticipated to occur during study; (7) treatment with rituximab within 90 days prior to baseline or anticipated to occur during study. In subjects who received rituximab more than 90 days but less than 6 months prior to baseline, prophylactic antibiotics (for e.g. Ciprofloxacin, erythromycin, penicillin V) are given upon initiation of study drug until 6 months after the last rituximab dose; (8) recent initiation of intravenous immunoglobulin (IVIg) (first cycle administered less than 90 days prior to baseline) or plasma exchange (PLEX) or treatment within 4 weeks prior to baseline or expected to occur during the 8-week treatment period; (9) active malignancy (except curatively resected squamous or basal cell carcinoma of the skin) requiring surgery, chemotherapy, or radiation within the prior 12 months (subjects with a history of malignancy who have undergone curative resection or otherwise not requiring treatment for at least 12 months prior to screening with no detectable recurrence are allowed); (10) history of any significant medical or psychiatric disorder or laboratory abnormality that renders subject unsuitable for participation in the study; and (11) participation in another concurrent clinical trial involving an experimental therapeutic intervention (participation in observational studies and/or registry studies is permitted).

Treatment Period

At day 1 visit, 0.3 mg/kg zilucoplan, or matching placebo administered SC are received by randomized subjects. Following in-clinic education and training, daily SC doses of blinded study drug, according to randomized treatment allocation, are self-injected by all subjects for the subsequent 8 weeks. Single-use pre-filled syringes in injection device is provided for use during the study. Subjects are expected to remain on stable doses of standard of care (SOC) therapy for IMNM throughout the study.

During the main portion of the study, the total duration of study participation for all subjects is up to approximately 12 weeks, including a Screening Period of up to 4 weeks and an 8-week Treatment Period. A study Extension Portion is made available for continued zilucoplan administration.

Subjects receive treatment with 0.3 mg/kg zilucoplan, or matching placebo, according to randomization, from Day 1 to Day 57 during the treatment period of the main portion of the study. Subjects who complete the week 8 (Day 57) visit (including those randomized to the placebo arm) have the option to continue treatment with zilucoplan in the extension portion of the study.

Assessments made during the main study include weight measurement; review and documentation of concomitant medications; symptom-directed physical examination; assessment of vital signs (e.g., heart rate, body temperature, and blood pressure in sitting position); 12-lead ECG; collection of blood samples for laboratory testing (hematology, chemistry, CK, coagulation, ADA testing and collection of blood samples for central testing of disease specific antibody testing (anti-HMGCR or anti-SRP autoantibodies), pharmacokinetic analysis, pharmacodynamic analysis, and biomarker analysis); collection of urine for urinalysis; urine pregnancy testing for females of childbearing potential; and efficacy assessment of triple timed-up-and-go (3TUG) (in ambulatory subjects only), proximal manual muscle testing (MMT), physician global visual analogue scale (VAS), patient global VAS, health assessment questionnaire (HAQ), myositis disease activity assessment tool (MDAAT) and functional assessment of chronic illness therapy (FACIT)-fatigue scale.

Sample Analysis

Hematology, chemistry and coagulation analytes that are assessed during the study are identified in Table 4. All laboratory samples are collected prior to the administration of drug on day 1 (baseline), day 8, day 15, day 29 and day 57. Coagulation tests are only performed in subjects receiving anticoagulant therapy.

TABLE 4

Chemistry, hematology and coagulation analytes

| Chemistry | Hematology |
|---|---|
| Alanine aminotransferase (ALT) | Hematocrit |
| Albumin | Hemoglobin |
| Alkaline phosphatase (ALP) | Mean corpuscular hemoglobin (MCH) |
| Amylase | Mean corpuscular hemoglobin concentration (MCHC) |
| Aspartate aminotransferase (AST) | Mean corpuscular volume (MCV) |
| Blood urea nitrogen (BUN) | Platelet count |
| Calcium | Red blood cell (RBC) count |
| Chloride | White blood cell (WBC) count and differential: |
| Creatinine | Basophils (% and absolute) |
| Gamma-glutamyl transferase (GGT) | Eosinophils (% and absolute) |
| Glucose | Lymphocytes (% and absolute) |
| Lactate dehydrogenase (LDH) | Monocytes (% and absolute) |
| Lipase | Neutrophils (% and absolute) |
| Potassium | Coagulation (if applicable) |
| Sodium | International normalized ratio (INR)/prothrombin time (PT) |

TABLE 4-continued

| Chemistry, hematology and coagulation analytes | |
|---|---|
| Chemistry | Hematology |
| Total bilirubin | Partial thromboplastin time (PTT) or activated partial |
| Total protein | thromboplastin time (aPTT) |
| | Other |
| | Aldolase |
| | C-reactive protein (CRP) |
| | Creatinine Kinase (CK) |

During the main portion of the study, blood samples for PK and PD analysis are collected from all subjects prior to administration of drug (within 1 hour of dosing) on day 1 (baseline), day 8, day 15, day 29 and day 57. Blood sample analytes assessed during the study include those listed in Table 4. Plasma concentration of zilucoplan and its metabolites, classical complement pathway activation (via hemolysis assay), and C5 levels are assessed.

Given the reliable relationship between CK levels, disease activity and treatment response in IMNM, and the faster response and greater higher sensitivity of CK to effective treatment interventions compared with clinical measures, CK is chosen as the primary endpoint for the study. The primary efficacy endpoint is percent change from baseline to week 8 in CK levels. CK levels are collected and measured from all subjects on day 1 (baseline), day 8, day 15, day 29 and day 57.

Secondary efficacy endpoints include week 8 change from baseline in 3TUG test (in ambulatory subjects only); proximal MMT; physician global activity VAS; patient global activity VAS; health assessment questionnaire; MDAAT score; American College of Rheumatology/European League Against Rheumatism (ACR/EULAR) response criteria and FACIT-fatigue scale.

Blood samples for biomarker testing are obtained prior to administration of drug (within 1 hour of dosing) on day 1 (baseline), day 8, day 15, day 29 and day 57. The analysis of biomarkers pertaining to the pathophysiology of IMNM [e.g., complement fixation, complement function, complement pathway proteins, autoantibody characterization (titer and immunoglobulin class), myocyte markers, and inflammatory markers] are used to provide further insight into the clinical efficacy and safety of zilucoplan in subjects with IMNM. Complement protein levels and complement activity is tested to evaluate response to zilucoplan and to understand subject characteristics related to variations in response to drug. Markers of inflammation are tested to assess correlation with complement function and clinical response to zilucoplan. A list of analytes is created through review of the literature, ongoing clinical studies, and ongoing exploratory work, and is finalized after completion of the study. The completion of these investigations is conditional based on the results of this or other clinical studies, and samples are selected for analysis on the basis of clinical outcome.

Example 8. Extension Portion

At the conclusion of the treatment period in the main portion of the study described in the previous Example, all subjects are given the option to receive zilucoplan in an extension portion of the study provided they met extension portion selection criteria. Subjects originally assigned to the placebo arm during the main portion of the study have the opportunity to receive zilucoplan. Assessments and visits during the first 8 weeks of the extension portion are identical to the main portion of the study for all subjects to ensure appropriate monitoring of subjects transitioning from placebo to active treatment and to maintain blinding of treatment assignment.

Selection criteria for inclusion in the extension portion includes: (1) completion of the main portion of the study; (2) negative serum pregnancy test at screening for female subjects of childbearing potential and a negative urine pregnancy test within 24 hours prior to the first dose of study drug; (3) agreement to use effective contraception during the study for sexually active female subjects of childbearing potential (i.e., women who are not postmenopausal or who have not had a hysterectomy, bilateral oophorectomy, or bilateral tubal ligation) and all male subjects (who have not been surgically sterilized by vasectomy); (4) use of any disallowed medications per the exclusion criteria from the main portion of the study or altered dosing of any other concomitant medication, unless medically indicated; (5) and no new medical conditions since entry into the main portion of the study.

Example 9. Pharmacogenomic Analysis

For subjects who decided to participate in pharmacogenomic studies, a blood sample is obtained at any study visit. Genomic studies [e.g., deoxyribonucleic acid (DNA) sequencing, DNA copy number analysis, and ribonucleic acid expression profiling] are performed and include exploration of whether specific genomic features correlate with response or resistance to study drug.

Example 10. Urinalysis

Urinalysis is performed on samples collected during screening to assess pH, specific gravity, protein (qualitative), glucose (qualitative), ketones (qualitative), bilirubin (qualitative), urobilinogen, occult blood, hemoglobin, and cells. A microscopic examination is performed where necessary to confirm measurement.

Example 11. Effect of Zilucoplan on Myopathy in Mice after Passive Transfer of Immunoglobin G (IgG) from Anti-HMGCR$^+$ IMNM Patients Plus Human Complement A study was carried out to evaluate the efficacy of zilucoplan in mice transferred with IgG from anti-HMGCR$^+$ IMNM patients. 8- to 12-week-old C5-deficient B10.D2/oSn mice were divided into three groups of 8 animals each. Intraperitoneal injections of 2 mg of IgG purified from an anti-HMGCR$^+$ patient or healthy donor were administered every other day for 8 days. To reduce anti-human xenogeneic immune responses, a single dose of 300 mg/kg of cyclophosphamide at day-1 was also administered.

Pooled human serum (Innovative Research, Novi, MI) with human complement components was depleted of IgG using Protein-G affinity chromatography. Experiments were performed at 4° C. to avoid complement degradation and serum preparations were stored at −80° C. until use. After IgG depletion, complement activity in serum preparations was confirmed by hemolysis assay. Mice were supplemented by daily intraperitoneal injections of 200 μL of the IgG-depleted (complement-preserved) serum. Mice receiving anti-HMGCR IgG also received daily subcutaneous administration of zilucoplan at a dose of 10 mpk (mg/kg). Zilucoplan injection was started at day 0, 30 minutes prior to the administration of the IgG-depleted serum, and then daily until day 8.

Figure 2:
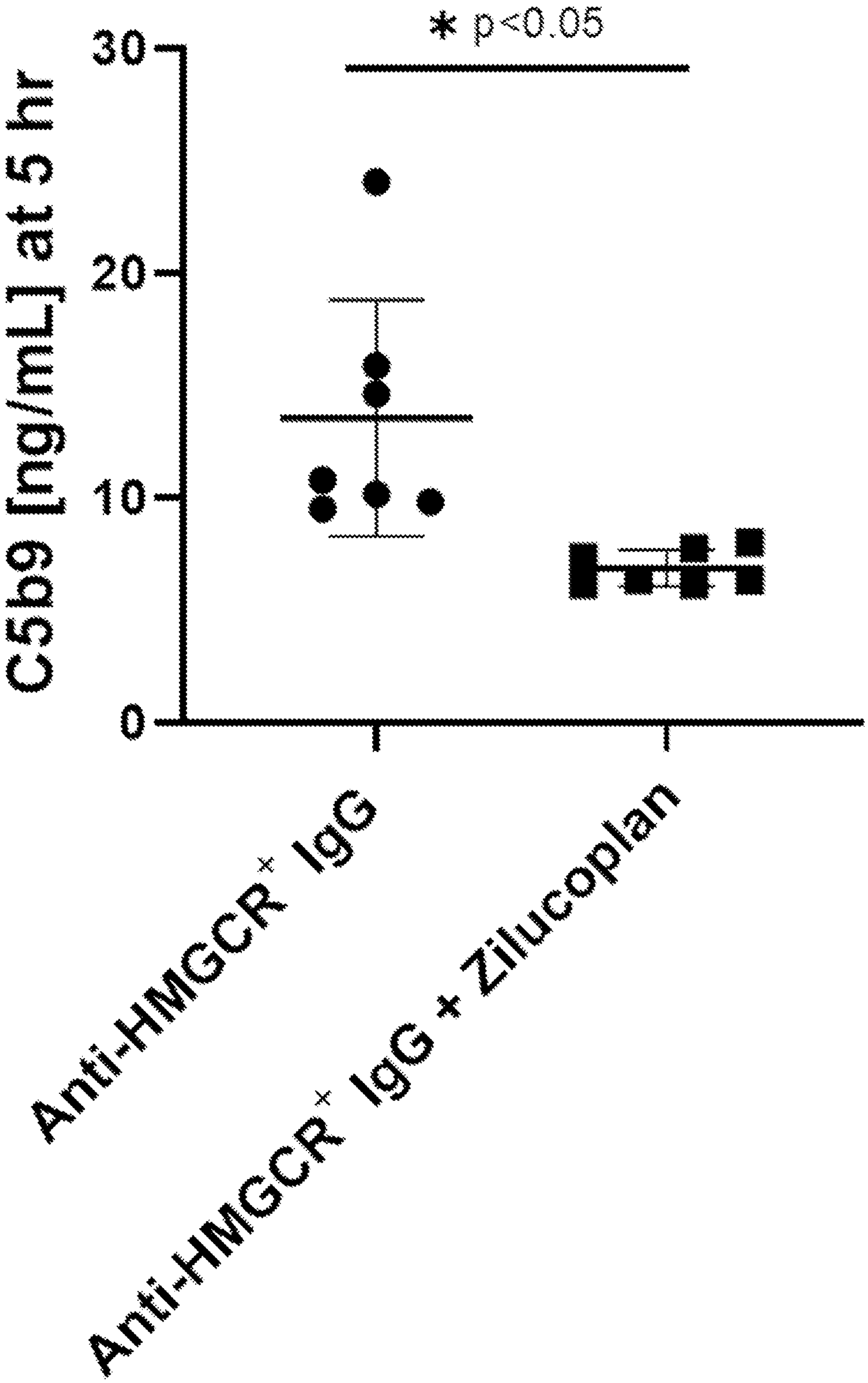
FIG. 2 is a graph showing concentration of human C5b-9 in serum samples derived from C5-deficient mice that were administered human anti-HMGCR IgG antibodies and NETS. Serum samples were obtained after five hours of treatment with or without zilucoplan.

To assess levels of human C5 cleavage in treated animals, mouse serum samples were obtained from pre-dosed animals and at time 0.5, 5, and 192 hours following first injection of the IgG-depleted serum. C5a and soluble C5b-9 (sC5b-9) levels were measured by multiplex ELISA assay (Quidel, #A900). Serum samples obtained 5 hours after IgG-depleted serum administration were diluted 1:5 with diluent buffer provided in the ELISA kit and assays were performed according to kit manufacturer's protocol. Human C5a (FIG. 1) and human sC5b-9 levels (FIG. 2) were significantly reduced in samples from zilucoplan-treated animals at the 5 hour time point.

Figure 3:
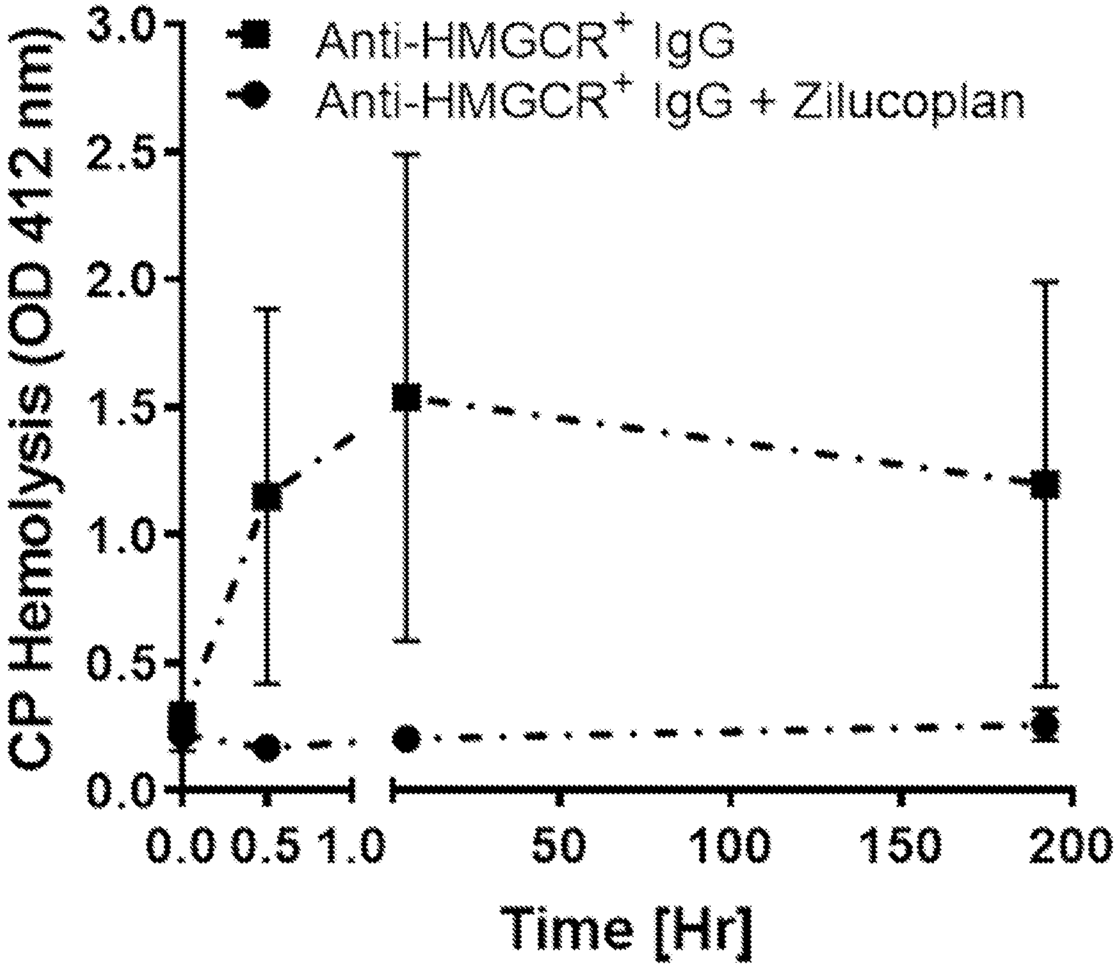
FIG. 3 is a graph showing classical pathway (CP) hemolysis levels (as interpreted from assay well optical density values) in serum samples obtained from C5-deficient mice after administration of human anti-HMGCR IgG antibodies and NHS and after treatment with or without zilucoplan.

The pharmacodynamic (PD) effect of zilucoplan on the classical pathway (CP) of hemolysis was assessed by CP hemolysis assay. Briefly, mouse serum samples were obtained from pre-dosed animals and at time 0.5, 5, and 192 hours following first injection of the IgG-depleted serum. Samples were supplemented with 2% human CS-depleted sera (Complement Technology, #A320) and incubated with GVB++ buffer (Complement Technology, #B100) and antibody-sensitized sheep erythrocytes (Complement Technology, #B201) in a 96-well tissue culture treated plate (USA Scientific, #CC76B2-7595) at 37° C. for 1 hour. The plate was then centrifuged at 1000×g for 3 minutes to pellet the remaining erythrocytes, and the supernatant was transferred to a second 96-well tissue culture treated plate. The optical density (OD) of the supernatant was measured at 412 nm to determine the extent of hemolysis in each well. As seen from FIG. 3, administration of zilucoplan completely inhibited hemolysis in corresponding serum.

Figure 4:
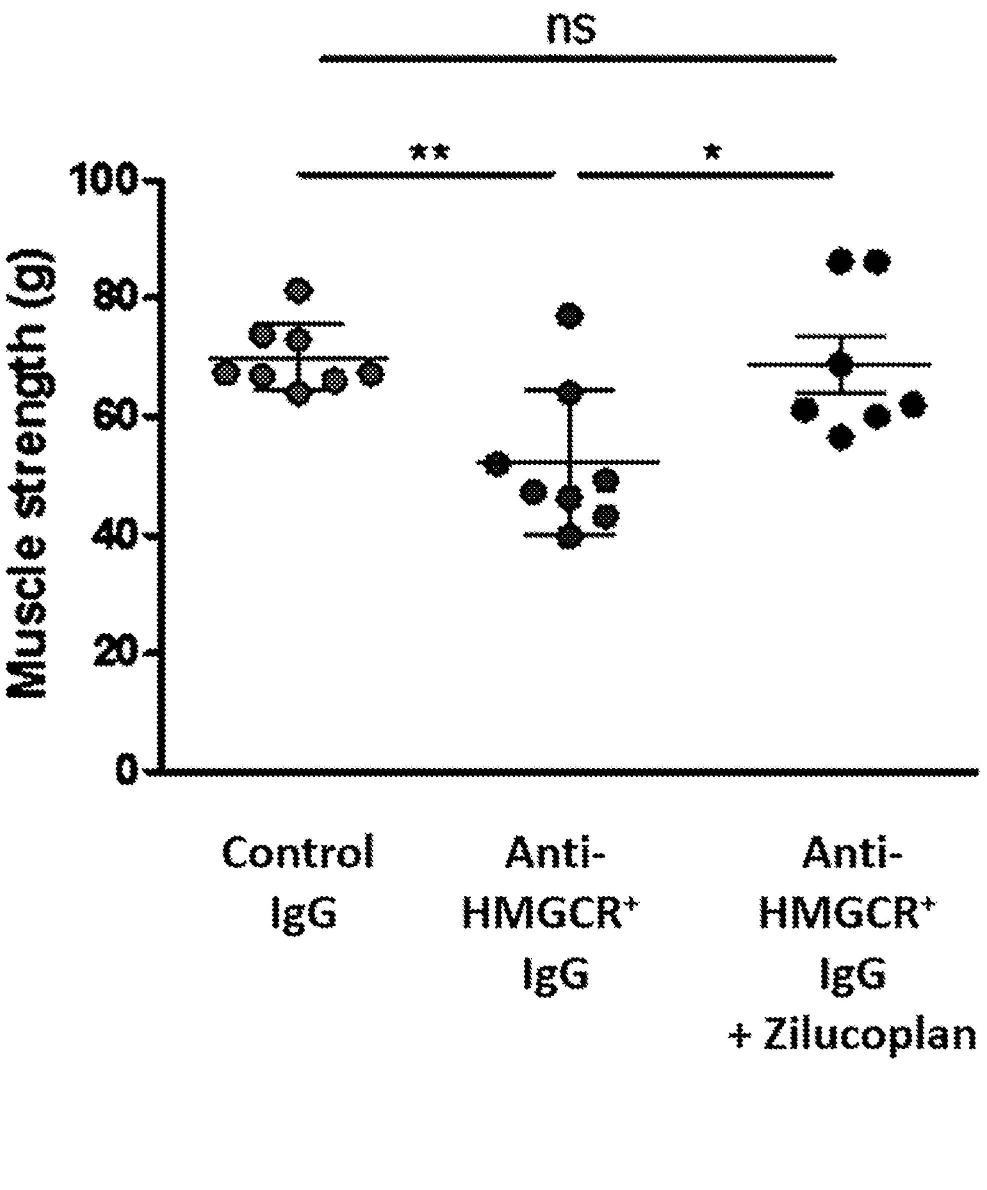
FIG. 4 is a graph showing maximal tetanic force values in grams produced by mouse gastrocnemius muscle contraction after sciatic nerve electrostimulation.

Muscle strength was evaluated in anesthetized animals on day 8 by directly measuring muscle contraction of one gastrocnemius muscle upon sciatic nerve electrostimulation. To obtain measurements, animals were anaesthetized by intraperitoneal injection of a mixture of xylazine and ketamine. In each animal, the Achilles tendon of the right gastrocnemius muscle was exposed and linked to a FT03 isometric force transducer (Grass Instrument, West Warwick, RI, USA) coupled to a LabView interface for recording and analysis (PowerLab system and Chart 4 software, AD Instruments, Paris, France). The knee joint was firmly immobilized. Maximal tetanic force produced by gastrocnemius muscle was evaluated upon electrostimulation of the sciatic nerve by bipolar electrode using a supramaximal (5V) square-wave pulse of 0.1 ms. After manual settings of optimal muscle length, the stimulation protocol was performed as follows: frequency was set at 100 Hz and train duration at 300 ms. Force values were recorded in grams. Passive transfer of IgG from anti-HMGCR antibody positive (anti-HMGCR$^+$ IgG) IMNM patients led to decreased muscle strength, an effect that was completely inhibited with zilucoplan administration (see FIG. 4).

Example 12. Tissue Analysis

After muscle strength measurements, mouse muscles (1 gastrocnemius, 1 tibialis anterior, 1 triceps per mouse) from the study described in Example 11 are snap frozen into isopentane, cooled in liquid nitrogen, and cut at 6 Cryosections are stained using haematoxylin and eosin and examined for necrotic myofibers. While the level of myofiber necrosis is low in this model, necrotic myofibers (defined as pale and/or hyalinized muscle fibers combined with loss of sarcolemmal integrity/coarse appearance) are searched for and counted manually.

C5b-9 deposits in cryosections are detected by immunofluorescence. Cryosections are incubated with an anti-human C5b-9 antibody, followed by a fluorochrome-labelled secondary antibody or similar biotinylated secondary antibody system. Cryosections are counterstained with Hoescht solution and examined for positive C5b-9 immunostaining.

What is claimed is:

1. A method of treating Immune-Mediated Necrotizing Myopathy (IMNM), the method comprising administering a C5 inhibitor to a subject having IMNM.

2. The method of claim 1, wherein the subject has an IMNM subtype that is anti-signal recognition particle (Anti-SRP) subtype.

3. The method of claim 1, wherein the subject has an IMNM subtype that is Anti-HMG-CoA reductase (Anti-HMGCR) subtype or antibody negative subtype.

4. The method of claim 1, wherein one or more IMNM-related symptoms are reduced or eliminated in the subject and the one or more IMNM-related symptoms comprise one or more of muscle weakness, chronic muscle inflammation, muscle atrophy and fatty replacement, elevated serum creatine kinase (CK), dysphagia, neck weakness, myalgia, muscle fiber necrosis, and interstitial lung disease.

5. The method of claim 1, wherein the C5 inhibitor is administered in combination with a therapeutic agent and/or therapeutic regimen that comprises one or more of rituximab, a steroid, an immunosuppressive therapy (IST), and an intravenous immunoglobulin therapy.

6. The method of claim 1, wherein the C5 inhibitor comprises a peptide, optionally wherein the peptide is a macrocyclic peptide.

7. The method of claim 1, wherein the C5 inhibitor is zilucoplan.

8. The method of claim 1, wherein CK levels of the subject are reduced after 8 weeks of complement inhibitor treatment.

9. The method of claim 1, wherein improvement in a secondary endpoint is observed after treatment with the C5 inhibitor, wherein the secondary endpoint comprises an improved score from an assessment comprising one or more of Triple Timed Up and Go (3TUG) Testing, Abbreviated Manual Muscle Testing in 8 Groups (MMT8), Physician Global Activity Visual Analogue Scale (VAS) assessment, and Patent Global Activity VAS assessment.

10. The method of claim 7, wherein zilucoplan is administered at a dose of from about 0.1 mg/kg to about 0.3 mg/kg.

11. The method of claim 7, wherein zilucoplan is administered daily.

12. The method of claim 7, wherein zilucoplan administration comprises self-administration.

13. The method of claim 7, wherein zilucoplan is administered by subcutaneous injection, optionally wherein the subcutaneous injection comprises the use of a prefilled syringe, the use of a self-administration device, and/or the use of a 29-gauge needle.

14. The method of claim 13, wherein the subcutaneous injection comprises the use of self-administration device, wherein the self-administration device comprises an auto injection device comprising a prefilled glass syringe comprising a fill volume of from about 0.2 ml to about 2 ml.

15. The method of claim 14, wherein zilucoplan is administered as a pharmaceutical composition comprising an aqueous solution.

16. The method of claim 7, wherein the subject is screened prior to zilucoplan administration, wherein the screening comprises:
- assessment of CK level;
- verification that subject age is between 18 and 75 years old;
- assessment of anti-HMGCR or anti-SRP antibody levels;
- manual muscle testing in at least one proximal limb muscle group;
- assessment of previous IMNM diagnosis;
- assessment of subject corticosteroid treatment history;
- assessment of subject immunosuppressive therapy treatment history; and/or
- a serum pregnancy test and/or a urine pregnancy test.

17. The method of claim 1, wherein the subject is evaluated or monitored for an IMNM characteristic, wherein the IMNM characteristic comprises an assessment made by one or more of CK level analysis, 3TUG test, Proximal MMT, Physician Global Activity VAS assessment, Patient Global Activity VAS assessment, HAQ, MDAAT score analysis, ACR/EULAR Response Criteria assessment, and FACIT-Fatigue scale assessment.

18. The method of claim 17, wherein treated subject CK levels are reduced at or before 8 weeks of treatment.

19. The method of claim 1, wherein the subject is evaluated for improvement in one or more of muscle strength, muscle function, and muscle tissue necrosis.

20. The method of claim 19, wherein the C5 inhibitor is zilucoplan and the neuromuscular inflammatory indication is IMNM.

21. The method of claim 1, the method comprising:
- administering zilucoplan to the subject; and
- evaluating subject muscle strength, wherein subject muscle strength is evaluated by measuring contraction of a subject muscle.

* * * * *

SEQUENCE LISTING

```
<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: SITE
<222> LOCATION: (1)..(6)
<223> OTHER INFORMATION: /note="Lactam bridge between residues"
<220> FEATURE:
<221> NAME/KEY: MOD_RES
<222> LOCATION: (7)..(7)
<223> OTHER INFORMATION: N-methyl-aspartic acid
<220> FEATURE:
<221> NAME/KEY: MOD_RES
<222> LOCATION: (8)..(8)
<223> OTHER INFORMATION: Tert-butylglycine
<220> FEATURE:
<221> NAME/KEY: MOD_RES
<222> LOCATION: (10)..(10)
<223> OTHER INFORMATION: 7-azatryptophan
<220> FEATURE:
<221> NAME/KEY: MOD_RES
```

-continued

```
<222> LOCATION: (14)..(14)
<223> OTHER INFORMATION: Cyclohexylglycine
<220> FEATURE:
<221> NAME/KEY: MOD_RES
<222> LOCATION: (15)..(15)
<223> OTHER INFORMATION: N-epsilon-(PEG24-gamma-glutamic acid-N-alpha-
      hexadecanoyl)Lys

<400> SEQUENCE: 1

Lys Val Glu Arg Phe Asp Xaa Xaa Tyr Xaa Glu Tyr Pro Xaa Lys
1               5                   10                  15
```